United States Patent [19]

Oswald et al.

[11] Patent Number: 4,595,753

[45] Date of Patent: Jun. 17, 1986

[54] HETEROCYCLE-SUBSTITUTED ALKYL DIARYL PHOSPHINE RHODIUM CARONYL HYDRIDE COMPLEX HYDROFORMYLATION CATALYST COMPOSITIONS

[75] Inventors: Alexis A. Oswald, Mountainside, N.J.; Torris G. Jermasen, Staten Island, N.Y.; Andrew A. Westner, Paramus; I-der Huang, West Paterson, both of N.J.

[73] Assignee: Exxon Research and Engineering Co., Florham Park, N.J.

[21] Appl. No.: 556,610

[22] Filed: Nov. 30, 1983

Related U.S. Application Data

[62] Division of Ser. No. 374,548, May 3, 1982, which is a division of Ser. No. 120,971, Feb. 12, 1980.

[51] Int. Cl.$^4$ .............................. C07F 9/58; C07F 9/65
[52] U.S. Cl. ...................................... 546/21; 548/400; 548/579; 548/101; 549/3
[58] Field of Search ...................... 546/2; 548/579, 400

[56] References Cited

U.S. PATENT DOCUMENTS

| | | |
|---|---|---|
| 3,239,566 | 3/1966 | Slaugh et al. |
| 3,644,446 | 2/1972 | Booth et al. .................... 260/429 R |
| 3,801,646 | 4/1974 | Booth . |
| 3,965,192 | 6/1976 | Booth .......................... 260/429 R X |
| 4,119,652 | 10/1978 | Knowles et al. ................ 260/429 R |
| 4,215,077 | 7/1980 | Matsumoto et al. ................ 568/454 |
| 4,283,562 | 8/1981 | Billing et al. ........................ 568/454 |
| 4,363,764 | 12/1982 | Billing et al. .................... 260/429 R |
| 4,376,870 | 3/1983 | Christopfel ........................... 568/15 |
| 4,400,548 | 8/1983 | Abatjoglon et al. ................ 568/454 |

OTHER PUBLICATIONS

Chem. Abstracts 94 156314g (1981).
Chem. Abstracts 82 16891v (1975).

*Primary Examiner*—Helen S. Sneed
*Attorney, Agent, or Firm*—R. J. North; E. Thomas Wheelock

[57] ABSTRACT

Compositions of matter are disclosed which are highly useful in hydroformylation processes. The compositions are non-charged, non-chelated bis- and tris-(alkyl diaryl phosphine) rhodium carbonyl hydrides. The substituents of the alkyl group include heteroorganic radicals containing silane, silicone, ether, ester, keto and hydroxy oxygen, phosphine oxide and phosphorus ester phosphorus, amine, amide, amine oxide and heterocyclic nitrogen groups.

These compositions are highly stable and selective catalysts for the hydroformylation of olefins under certain conditions. The disclosed catalyst systems contain a large excess of phosphine ligand and employ alpha-olefin plus synthesis gas reactant mixtures having a high $H_2$/CO ratio at relatively low pressures. They produce mostly aldehydes derived from terminal attack on the alpha-olefin reactant. In the case of low olefins, such as butene-1, the products can be advantageously removed in a continuous manner, as distillate components from a ligand reaction mixture kept at an elevated temperature and continuously fed by an appropriate mixture of the reactants.

11 Claims, 13 Drawing Figures

KEY STEPS IN THE MECHANISM OF PHOSPHINE-RHODIUM
COMPLEX CATALYZED HYDROFORMYLATION OF OLEFINS

HETEROCYCLE-SUBSTITUTED ALKYL DIARYL PHOSPHINE RHODIUM CARONYL HYDRIDE COMPLEX HYDROFORMYLATION CATALYST COMPOSITIONS

This division of application Ser. No. 374,548, filed 5/3/82, which is R. 60 divisional of 120,971 filed 2/12/80.

TECHNICAL FIELD

The present invention is related to selective alkyl diaryl phosphine transition metal complex olefin hydroformylation catalysts. More particularly, the subject of this invention is certain, new selective alkyl diaryl phosphine rhodium complex hydroformylation catalysts. As such, the invention is specifically related to substituted tris-(alkyl diphenyl phosphine) rhodium carbonyl hydride complexes.

A special aspect of the invention is concerned with the preparation, physicochemical and catalytic properties of the novel complexes, i.e., phosphine basicity, stereochemistry versus complex formation, thermal stability of complexes, correlations of catalyst selectivity and activity with hydroformylation reaction rates at different temperatures. The effects of excess phosphine ligand, excess hydrogen, carbon monoxide partial pressure on the catalytic properties and on catalyst selectivity to linear aldehydes are also related.

BACKGROUND ART

Transition metal complexes containing phosphine ligands have been widely studied as catalysts for hydroformylation and hydrogenation. General application of such complexes in reaction with carbon monoxide are discussed, e.g., in the monograph of Juergen Falbe, "Carbon Monoxide in Organic Synthesis, Springer Verlag, New York, 1970.

There were a number of all inclusive patent disclosures on the use of phosphine rhodium complexes as hydroformylation catalysts: German Offenlegungsschrift 2,758,473 by W. E. Smith (assigned to General Electric) disclosed them for allyl alcohol hydroformylation; U.S. Pat. No. 4,137,240 by M. L. Peterson (assigned to E. I. DuPont de Nemours and Co.) described them for 2-vinyl-4-methyl-1,3-dioxane batch hydroformylation; U.S. Pat. No. 3,965,192 by F. B. Booth (assigned to Union Oil Co. of California) disclosed them for the hydroformylation of monoolefins; U.S. Pat. No. 4,041,082 by T. Onoda and T. Masuyama (assigned to Mitsubishi Chemical Industries) defined such complexes broadly in a process for their reactivation; U.S. Pat. No. 3,821,311 by O. R. Hughes and M. E. D. Millman (assigned to Celanese Corp.) also disclosed the use of such complexes broadly when used with bases for combined hydroformylation, aldolization. Similarly, British Pat. No. 1,243,189 by M. J. Lawrenson and G. Foster (assigned to British Petroleum Co., Ltd.) provided an all inclusive definition of phosphines in such catalyst complexes also containing chelating diketones. Finally, U.S. Pat. No. 4,052,461 by H. B. Tinker and D. E. Morris (assigned to Monsanto Co.) disclosed rhodium containing cations which can include any tertiary phosphine.

Most of the prior art work was carried out with either triaryl phosphine or trialkyl phosphine complexes. The present study concentrated on an investigation of the complexes of some "mixed ligand structures," i.e., alkyl diphenyl phosphines. Prior to the present work, rhodium complexes of these ligands could not be used tp advantage.

The basic chemistry of hydroformylation and its catalysis by transition metal compounds, including phosphine-rhodium complexes is known and has been recently reviewed and summarized by R. L. Pruett in Vol. 17 of "Advances in Organo Metallic Chemistry" ed. S. G. Stone and R. West, *Academic Press*, New York, N.Y. 1979 in a chapter entitled Hydroformylation, Pruett concluded that, for a selective rhodium catalyzed hydroformylation of alpha-olefins to n-aldehydes, critical combinations of several reaction parameters were required. The author states that these parameters included low partial pressure of carbon monoxide, high concentration of excess phosphite or aryl phosphine ligands and low total gas pressure.

In U.S. Pat. Nos. 3,527,809 and 3,917,661; Pruett and Smith state that suitable ligands for rhodium catalysts for hydroformylation must be weakly basic, having a half neutralization potential ($\Delta$HMP) of at least 425 millivolts (preferably 500) above that of diphenyl guanidine. As such weakly basic ligands, Pruett and Smith mentioned among others phosphites and triaryl phosphines. They specifically indicate that stronger phosphines bases, such as diaryl alkyl phosphines, should be excluded as ligands for selective rhodium catalysis. Similar disclosures are also contained in Pruett and Smith's U.S. Pat. No. 4,148,830, where they additionally state that suitable ligands should be free of sterically hindered aromatic groups.

In German Offenlegungsschrift 2,802,922 (based on U.S. Ser. No. 762,335, filed on Jan. 25, 1977 in the names of D. G. Morrell and P. D. Sherman, Jr.), there is described a process including the addition of small amounts of diaryl alkyl phosphine ligands to a tris-triphenyl phosphine rhodium complex system. However, substantially all of the free ligand in the Morrell et al. system is a triaryl ligand, and it is specifically stated that the invention is not intended to include the use of diaryl alkyl phosphine ligands alone. Some of the diaryl alkyl phosphine ligands which are apparently disclosed in this German publication for use in that particular content include methyl diphenyl phosphine, ethyl diphenyl phosphine, propyl diphenyl phosphine, butyl diphenyl phosphine, ethyl-bis(p-methoxy phenyl) phosphine, ethyl-phenyl-p-biphenyl phosphine, methyl-phenyl-p(N,N-dimethylaminophenyl) phosphine, propyl-phenyl-p-(N,N dimethylaminophenyl) phosphine, and propyl-bis-(p-methoxy phenyl) phosphine.

Still other patents and publications also mention the use of certain other alkyl phosphines as ligands in rhodium catalyzed hydroformylation reactions. For example, ethyl ditolyl phosphine is mentioned as a possible ligand by Peterson in U.S. Pat. No. 4,137,240. Wilkinson, U.S. Pat. No. 4,108,905, discloses ethyl diphenyl phosphine as a ligand for a rhodium hydrido carbonyl complex, which he says may be used in the presence of molten triphenyl phosphine as reaction medium. British Pat. No. 2,014,138 discloses the use of, among others, alkyl diaryl phosphines, e.g., propyl diphenyl phosphine, in combination with certain diphosphino alkanes in rhodium hydrido carbonyl complex systems. Booth in U.S. Pat. No. 3,560,539 mentions as a ligand ethyl diphenyl phosphine, while Booth et al., U.S. Pat. No. 3,644,446, discloses as possible ligands ethyl diphenyl phosphine and methyl dixylyl phosphine. Slaugh et al., in U.S. Pat. No. 3,239,566 mentions diphenyl butyl phosphine, methyl diphenyl phosphine, ethyl diphenyl phosphine and diphenyl benzyl phosphine as possible ligands for rhodium or ruthenium catalysts. Chemistry Letters, (1972) pp. 483–488, refers to a rhodium complex bonded to (+)-diphenylneomenthyl phosphine.

Other Union Carbide researchers disclosed additional inventions mostly related to the commercial TPP-rhodium complex catalyzed process. German Offenlegungsschrift 2,715,685 by E. A. V. Brewster and R. L. Pruett described the continuous process in detail. Also, it showed the harmful effect of aldehydes having conjugated olefinic unsaturation. German Offenlegungsschrift 2,730,527 by R. W. Halstead and J. C. Chaty disclosed the addition of appropriate, minor amounts of oxygen to the reaction mixture of the continuous process to maintain activity.

Alkyl diaryl phosphine ligands were specifically disclosed as potential rhodium catalyst stabilizer ligands in a number of patents and journal articles on rhodium catalyzed hydroformylation, U.S. Pat. No. 4,108,905 by G. Wilkinson (assigned to Johnson Matthey & Co., Ltd.) disclosed ethyl diphenyl phosphine as a stabilizing ligand as a part of an all inclusive, but sparsely supported, disclosure on phosphine ligands. British Patent Application No. 2,014,138 (assigned to Kuraray Co., Ltd.) similarly disclosed bis-diarylphosphino alkanes, i.e., diaryl phosphine substituted alkyl diaryl phosphines, as stabilizing ligands. U.S. Pat. No. 4,151,209 by J. L. Paul, W. L. Pieper and L. W. Wade (assigned to Celanese Celanese Corp.) reported on the formation of propyl diphenyl phosphine ligand from the TPP-rhodium catalyst during propylene hydroformylation. U.S. Patent Nos. 3,560,539; 3,644,446 and 3,801,646 by F. B. Booth (assigned to Union Oil Co. of California) disclosed the derivation of undefined rhodium catalyst complexes by reduction, starting with a variety of phosphines including methyl diphenyl phosphine or propyl diphenyl phosphine. U.S. Pat. No. 3,239,566 by L. H. Slaugh and R. D. Mullineaux (assigned to Shell Oil Co.) disclosed methyl diphenyl phosphine, ethyl diphenyl phosphine and benzyl diphenyl phosphine as examples for an all inclusive definition of phosphine complexes of rhodium and ruthenium. Slaugh preferred the complexes of tributyl phosphine, started with rhodium chloride and emphasized the formation of alcohols as well as aldehydes in his process.

There are a number of patents which disclosed asymmetrical, optically active alkyl diaryl phosphines for the stereoselective hydroformylation of special olefins such as styrene, e.g., Canadian Pat. No. 1,027,141 by H. B. Tinker and A. J. Solodar (assigned to Monsanto Co.); British Pat. No. 1,402,832 by C. Botteghi, G. Consiglio and C. Salomon (assigned to P. Pino); U.S. Pat. No. 4,139,565 by J. D. Unruh and L. E. Wade (assigned to Celanese Corp.) and French Pat. No. 72.43479 by R. Stern, D. Commereuc, Y. Chavin and H. B. Kagan (assigned to the Institute Francais du Petrole, des Carburants et Lubrifiants). Although these ligands are structurally related to those of the present work, their properties and application is outside the scope of the present invention.

The most conclusive study regarding the effect on hydroformylation catalysis of an excess of a simple alkyl diphenyl phosphine, i.e., ethyl diphenyl phosphine, was published by A. R. Sanger in the Journal of Molecular Catalysis [3, pages 221–226, particularly page 222 (1977/1978)]. He reported that the addition of ethyl diphenyl phosphine to the TPP-rhodium catalyst resulted in less increase in catalyst activity at 20° C. than that of excess TPP. He found similar effects when chelating di-alpha, ω-diphenylphosphino-alkanes were added. Using more than molar amounts of 1,4-diphenylphosphino-butane resulted in decreased catalyst activity.

There is much less information on hydroformylation catalysis by the rhodium complexes of substituted aliphatic phosphines, particularly substituted alkyl diaryl phosphines. Catalyst complexes of such phosphines are usually within the all inclusive scope of several patent applications already discussed. However, very few specific disclosures were made. In effect, no direct disclosure of any tris-(substituted alkyl diphenyl phosphine) rhodium carbonyl hydride was found prior to this invention.

In the area of trihydrocarbylsilyl substituted diphenyl phosphine rhodium complexes containing halogen, there are several disclosures by G. Chandra (British Pat. Nos. 1,419,769; 1,420,928 and 1,421,136, assigned to Dow Corning Ltd.). Tris-(trimethylsilyl-methyl diphenyl phosphine) rhodium carbonyl chloride is specifically disclosed. Relatively non-selective hydroformylation catalysis by this and similar complexes was recently reported by M. O Farrell, C. H. Van Dyke, L. J. Boucher and S. J. Metlin [J. Organomet. Chem., 169 (2) 199 (1979)].

Carboxy substituted t-phosphine rhodium and cobalt complexes of rhodium were disclosed in an all inclusive unspecified manner as hydroformylation catalysts in British Pat. No. 1,350,822 by BASF A.G. 2-Carboxyethyl diphenyl phosphine was disclosed as an exemplary phosphine ligand.

Halogen, aryloxy, alkoxy, hydroxy, nitro and phenyl substituted phosphine rhodium complexes were included in an all inclusive definition of phosphine rhodium complex hydroformylation catalysts in British Pat. No. 1,298,331 by G. Wilkinson (assigned to Johnson, Matthey & Co., Ltd). However, not a singly substituted alkyl diaryl phosphine compound was named. Similarly, amino, halo and alkyl substituted rhodium complex hydroformylation catalysts were generically disclosed by F. B. Booth in U.S. Pat. No. 3,965,192 (assigned to Union Oil Co. of California) which was already referred to. Again, no example of substituted alkyl diaryl phosphine was given.

As far as alkyl diphenyl phosphines are concerned, many compounds are known. However, few aryl or nonhydrocarbyl substituted compounds were disclosed. A complete list of characterized compounds and their preparation, up to 1969, is given in Volume 1, Chapter 1, pages 154 to 162 by L. Maier, as a part of the series of monographs, entitled "Organic Phosphorus Compounds" by G. M. Kosolapoff and L. Maier, J. Wiley & Sons, Inc., New York, N.Y., 1972. However, none of the heteroorganic substituted compounds of the present invention is disclosed. Chapter 3 by G. Booth of the same book also lists characterized phosphine metal complexes. However, no rhodium carbonyl hydrides are found.

With regard to the synthesis of alkyl diphenyl phosphines in general, Kosolapoff and Maier lists a number of displacement reactions as being frequently used (see page 2). However, there is little information on diphenyl phosphine to olefin addition. No substituted alkyl diphenyl phosphine derived via addition is disclosed. As far as the hydrido carbonyl rhodium complexes of phosphines are concerned, the known, obviously applicable syntheses, are reviewed in Booth's chapter. They do not include the presently recommended methods.

In the area of the silylalkylphosphine intermediates of the present invention, there are several disclosures related to the present invention. British Pat. No. 925,721 by H. Niebergall (assigned to Koppers Co., Inc.) broadly disclosed the addition of secondary phosphines to unsaturated silanes to provide silylalkyl phosphines. British Pat. No. 1,179,242 by W. J. Owen and B. E. Cooper, assigned to Midland Silicones, Ltd., disclosed the preparation of similar compounds via displacement reactions of chlorophosphines and silylalkyl Grignard compounds or sodium phosphines and silylalkyl halides. The preparation of related compounds, i.e., alkoxysilylalkylphosphines was described via an alternative addition method reacting alkoxysilances and unsaturated phosphines, by F. Fekete in U.S. Pat. No. 3,067,227, assigned to Union Carbide Corp. Silylalkylphosphine intermediates useful in the preparation of the complexes of the present invention were disclosed by J. K. Jacques and W. J. Owen in British Pat. No. 1,182,763 assigned to Albright and Wilson (MFG) Ltd., by B. E. Cooper and W. J. Owen in a journal article on oxidation potentials [see J. Organometal. Chem., 29, 33–40 (1971)].

In the area of insoluble, anchored phosphine-transition metal complex catalysts reactive silyl substituted alkyl diphenyl phosphines were utilized as intermediates for anchoring. For reference, see U.S. Pat. No. 3,726,809 by K. G. Allum, S. McKenzie and R. C. Pitkethly and U.S. Pat. No. 3,907,852 by A. A. Oswald and L. L. Murrell. Such phosphine anchoring agents had at least one reactive substituent on the silicon. As such, they reacted with the surface hydroxyl group of silica via siloxane formation.

In contrast to the prior art, it was found in the present invention that tris-(alkyl diaryl phosphine) rhodium carbonyl hydride complexes are attractive selective hydroformylation catalysts in the absence of TPP-rhodium, dependent on several unexpected conditions. Compared to the widely studied triphenyl phosphine rhodium complexes, the optimum catalysis temperature of the present complexes is higher. Higher hydroformylation temperatures using the present catalysts are possible because catalyst stability and selectivity are better maintained.

One of the key unexpected factors in process of the present invention is that the present catalysts can be employed in a large excess without a drastic loss of catalyst activity. The other factor, also important for high selectivity, is the high ratio $H_2$ to CO. Unexpectedly, the excess of hydrogen does not result in the reduction of the aldehyde hydroformylation products to the corresponding alcohols. Coupled with the high $H_2/CO$ ratios, it is essential in the present process to employ relatively low pressures, effectively limiting the CO partial pressure. Finally, the continuous process of the present invention is distinguished by relatively low olefin conversions. These are important for both catalysts stability and selectivity.

Due to the above characteristics, the present alkyl diaryl phosphine complex catalysts are uniquely suited for an operation wherein the aldehyde product is separated from the catalyst by distillation. Such a specifically advantageous operation is carried out in a continuous fashion wherein the olefin and synthesis gas feed are continuously introduced into the reactor comprising the catalyst solution and a mixture of the aldehyde product and the feed is continuously withdrawn in the gas phase.

The preferred selective process of the present invention, particularly the combination of the above features, is unique. It is not only unexpected in view of the prior art but was described as a process which should be inoperative due to the type of phosphine ligands employed.

When compared to the tris-(triphenyl phosphine) rhodium carbonyl hydride (TPP-rhodium) plus triphenyl phosphine based commercial, continuous process, the present process exhibits surprising advantages. The alkyl diaryl phosphines of the present process do not undergo P-C bond scission. The only catalyst by-products are the corresponding phosphine oxides. The latter are not inhibitors. The secondary by-products derived from the aldehyde products such as aldehyde trimers do not seriously inhibit the present catalytic system either. The present catalysts stand out with regard to long term activity maintenance in a continuous process. In contrast to the known process, no introduction of oxygen and/or chelating compounds or use of hydroxylic solvent is required for activity maintenance. As a consequence of higher catalyst stability, the present process can be operated at higher temperatures. This, in turn, can lead to an improved product to feed ratio in the distillate of the continuous product flash-off process. Also, it extends applicability to higher olefins and olefin derivatives. In addition, it provides unexpected advantages when employed for combined hydroformylation-aldolization-hydrogenation processes.

The applicability of the present phosphine ligands unexpectedly but understandably depends on their steric requirements, too. Substituents on the alkyl moiety close to the phosphorus were found to inhibit phosphine complexation with rhodium compounds for the first time. In contrast, substituents outside the immediate proximity of phosphorus resulted in improved complex catalysts. Such substituted phosphines could be surprisingly advantageously produced via the addition of diaryl phosphines to vinyl compounds having activated double bonds.

The alkyl diaryl phosphines of the present invention were found to complex with rhodium more strongly than triaryl phosphines. This finding led to a novel method of producing the present catalysts via ligand displacement, e.g., by the reaction of alkyl diaryl phosphines with tris-(triphenyl phosphine) rhodium carbonyl hydride. According to another novel method, the present complexes are produced from acetylacetonato dicarbonyl rhodium either prior to use or in situ under the reaction conditions.

DISCLOSURE OF INVENTION

The present invention describes novel bis- and tris-(alkyl diaryl phosphine) rhodium carbonyl complexes and a novel hydroformylation process using said complexes.

The present complexes contain 2 or 3, preferably 3, coordinated alkyl diaryl phosphine moieties per rhodium, 1 to 3, preferably 1, carbon monoxide ligands per rhodium, and 1 or 0, preferably 1, hydride ligand per rhodium.

The preferred novel complexes are non-charged non-chelated bis- and tris-(alkyl diaryl phosphine) rhodium carbonyl hydrides of the formula

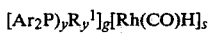

wherein Ar is aryl, preferably an independently selected $C_6$ to $C_{10}$ aromatic unsubstituted or substituted hydrocarbyl radical, more preferably phenyl, mono-, di- and tri-substituted phenyl, most preferably phenyl; $R^1$ is a $C_1$ to $C_{30}$, preferably $C_2$ to $C_{20}$, mono-, di-, tri- or tetravalent nonsubstituted or substituted saturated alkyl, including alkyl groups interrupted by noncharged heteroorganic groups such as those containing O, N, P, S, Si, with the proviso that if $R^1$ is a nonsubstituted monovalent alkyl, the minimum number of alkyl carbons is six; y is the valency of the alkyl group, g times y is 1 to 6, preferably 2 to 6, s is 1 to 3, preferably 2 or 3; said y and s being selected to satisfy the coordinative valences of rhodium in such a manner that there are 2 or 3, preferably 3, coordinated phosphine moieties per rhodium, all the aromatic and aliphatic groups and their substituents including nonhydrocarbon groups being chemically stable in hydroformylation systems.

While the value of g, y and h is dependent on the coordinative bonding of the rhodium, the tris-phosphine rhodium complex compositions are unexpectedly stable and as such preferred. In the case of monovalent alkyl, preferably substituted alkyl, diaryl phosphine rhodium complexes, the preferred compositions are accordingly of the formula

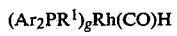

wherein $R^1$ is a monovalent alkyl as previously defined, preferably a substituted alkyl; g is 1 to 3, preferably 2 or 3, more preferably 3, and, of the formula

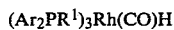

The alkyl diaryl phosphine complex catalyst compositions of the present invention include compounds containing positively charged rhodium. These complexes are preferably of the general formula

wherein the meaning of Ar and $R^1$ is the same as before and $X^-$ is an anion, preferably a non-coordinating anion, preferably selected from the group consisting of borate, aluminate, perchlorate, sulfonate, nitrate, fluorophosphate, fluorosilicate such as $Ph_2B^-$, $F_4B^-$, $ClO_4^-$, $Ph_3SO_3^-$, $NO_3^-$, $F_6P^-$, $F_6Si^{2-}$.

The preferred substituents of the aromatic groups are $C_1$ to $C_{30}$, preferably $C_1$ to $C_{12}$ alkyl, alkoxy, acyl, acyloxy, acrylamido, carbamido, carbohydrocarbyloxy, halogen, phenoxy, hydroxy, carboxy. These substituents are preferably bound to a phenyl group. Mono- and disubstituted phenyl groups are preferred.

Examples of the aromatic groups are phenyl, fluorophenyl, difluorophenyl, tolyl, xylyl, benzoyloxyphenyl, carboethoxyphenyl, acetylphenyl, ethoxyphenyl, phenoxyphenyl, biphenyl, naphthyl, hydroxyphenyl, carboxyphenyl, trifluoromethylphenyl, tetrahydronaphthyl, furyl, pyrryl, methoxyethylphenyl, acetamidophenyl, dimethylcarbamylphenyl.

The alkyl groups are primary and secondary alkyl groups, preferably primary alkyl groups. Next to the preferred primary α-carbons of the alkyl groups, the β-carbons are primary and secondary, preferably also primary. Accordingly, a preferred class of complexes is of the general formula

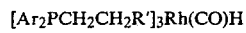

wherein R' is a $C_4$ to $C_{28}$, nonsubstituted or substituted alkyl of a preferably branched or cyclic character; a non-substituted or substituted $C_6$ to $C_{10}$ aryl, preferably phenyl; a nonhydrocarbyl group, preferably selected from organic radicals containing silicon, oxygen, nitrogen and phosphorus. The heteroatoms of the organic radicals are preferably of the trihydrocarbyl silane, hydroxy, ether, acyl, amine, amide, and phosphine oxide. The heteroatom is preferably directly bound to the β-methylene group.

The preferred substituents of the primary alkyl groups are the same. Some more preferred substituted alkyl diaryl phosphine complexes will be defined later.

Exemplary alkyl groups are methyl, n-hexyl, docosyl, triacontyl, fluoropropyl, perfluoroethyl-ethyl, isopropyl, primary isobutyl, cyclopentyl, t-butylethyl, cyclohexylethyl, phenylethyl, trimethylsilylethyl, hydroxy, methoxyethoxyethyl, acetylethyl, pyrrolidinonylethyl, tributylphosphonium substituted ethyl, tris-hydroxy substituted t-butylethyl, triphenylmethylethyl, hydroxypropyl, carbomethoxyethyl, phenoxyethyl, benzamidoethyl, benzoyloxyethyl, pyrrylethyl, furylethyl, thienylethyl. The nonhydrocarbyl, i.e., heteroorganic R' groups will be further defined.

The alkyl groups as defined by R' are mono- or polyvalent alkyl groups, their valence ranging from 1 to 4. The polyvalent groups may have a carbon skeleton or can be interrupted by appropriate heteroatoms such as oxygen, sulfur, nitrogen, silicon.

Exemplary polyvalent alkyl groups are tetramethylene, xylylene, oxy-bis-propyl, sulfone-bis-propyl, nitrilo-tripropyl, silicone-tetraethyl, cyclohexylene diethyl, keto-bis-ethyl.

A class of the alkyl groups is represented by aliphatic hydrocarbyl groups. Preferred subgroups of the latter are n-alkyl groups and hydrocarbyl substituted n-alkyl groups. When $R^1$ is one of these two subgroups, the preferred complexes are of the formula

and

wherein n is $C_6$ to $C_{30}$ and m is 1–22, preferably 2 to 22, more preferably 2 or 3 h is 2 or 3, R'' is a $C_3$ to $C_{27}$ branched alkyl, cycloalkyl, aryl, such as isopropyl, t-butyl, cyclohexyl, phenyl.

The choice of aryl and alkyl groups and their substituents is limited only by stereochemical and reactivity considerations. Sterically demanding groups inhibit the formation of the present tris-phosphine complexes. Groups which are reactive under the use conditions of the present complexes are apparently undesirable as catalysts.

A preferred broad class of bis- or tris-alkyl diaryl phosphine complexes is of the general formula

     I wherein Ar is an aryl group containing from 6 to 10 carbon atoms;

Q is a saturated divalent organic radical selected from an alkylene radical and an alkylene radical the carbon chain of which is interrupted with either oxygen or phenylene groups, wherein the alkylene radical contains from 2 to 30 carbon atoms;

E is a member selected from

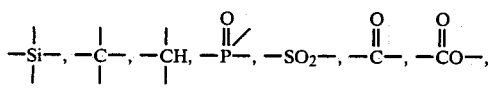

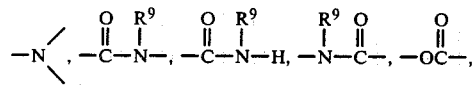

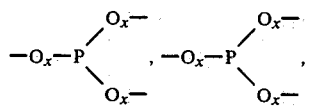

—O— and —S—, wherein $R^9$ is a member selected from H, an alkyl group containing 1 to 30 carbon atoms and an aryl group containing from 6 to 10 carbon atoms, and wherein x is an integer of 0 or 1 with the proviso that at least one x is 1;

y represents the number of bonds available from the group E for attachment to the groups Q and R;

R represents a member selected from an alkyl group containing from 1 to 28 carbon atoms and an aryl group containing from 6 to 10 carbon atoms and when E is —N, R also represents a member selected from

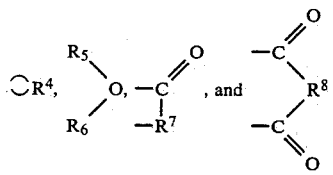

which together with the N atom forms a heterocyclic ring, wherein $R^4$, $R^5$, $R^6$, $R^7$ and $R^8$ are hydrocarbyl radicals such that said heterocyclic ring contains from 5 to 6 atoms;

b is an integer of from 1 to 4, provided that y-b is not less than zero,

X is an anion or organic ligand, excluding halogen, satisfying the coordination sites of the rhodium metal; $RhX_n$ is preferably $Rh(CO)H$ g times b is 1 to 6;

n is 2 to 6; and s is 1 to 3.

A preferred class of compounds of the invention are compounds of the formula

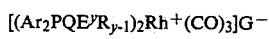

wherein Ar, Q, E, y and R are as defined above and $G^-$ is an anion, preferably a non-coordinating anion. Suitable $G^-$ anions include borates, aluminates, perchlorates, sulfonates, nitrates, fluorophosphates and fluorosilicates, such as $Ph_4B^-$, $F_4B^-$, $ClO_4^-$, $Ph_3SO_3^-$, $CF_3SO_3^-$, $NO_3^-$, $F_6P^-$ and $F_6Si^{-2}$.

A preferred class of alkyl diphenyl phosphine rhodium complexes is of the following formula

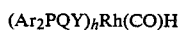

and

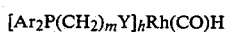

wherein Ar and h have the previously defined meaning, m is 1 to 30, preferably 2 to 22, more preferably 2 or 3, most preferably 2; Q is a $C_1$ to $C_{30}$, preferably $C_2$ to $C_{22}$, more preferably a $C_2$ to $C_3$, most preferably a $C_2$ unsubstituted or substituted, preferably unsubstituted, saturated straight chain divalent organic radical, more preferably a polymethylene radical which can be interrupted by either oxygen and phenylene; Y is a non-charged organic, preferably hetero-organic substituent, preferably with 3 to 30 carbon atoms, having a higher steric requirement than methylene and polymethylene such as trihydrocarbylsilyl, quaternary tetraalkyl phosphonium, heterocyclic tertiary nitrogen, phosphine oxide, sulfone, carbonyl, carboxylate or sterically demanding hydrocarbon groups, the latter being exemplified by phenyl, triphenylmethyl, t-butyl, trishydroxy substituted butyl and the like.

As far as novel compounds having phosphorus based heteroorganic substituents for Y are concerned, chelate forming amines, phosphines and phosphonium salts are excluded from this application. Y is preferably a $C_1$ to $C_{30}$, preferably $C_1$ to $C_{10}$, organic radical selected from the group consisting of substituted and unsubstituted secondary and tertiary alkyl, substituted and unsubstituted aryl, preferably phenyl and heteroorganic radicals. The heteroorganic radicals are defined as radicals having an atom, with an unsatisfied valency to be bound to Q, which is either a carbon having a hetero-atom substituent or is a heteroatom itself. The heteroatoms are preferably oxygen, sulfur, phosphorus, silicon and nitrogen, more preferably carbonyl, O, sulfone, S, phosphine or phosphine oxide, P, silane, Si, and amide, N. Heteroorganic radicals, especially silyl radicals, are most preferred.

If the Q is substituted, the substituents are the same as previously defined for Ar and R. Exemplary Q radicals are ethylene, butylene, docosamethylene, tricontamethylene, phenyl bis(ethyl), ethylene bis(oxyethyl), ethylene-bis oligo (oxyethyl), oxy ethyl propyl, oxy ethyl perfluoroethyl, oxy ethyl hydroxypropyl.

When Y is an alkyl radical, it is preferably saturated open chain and/or cyclic. The preferred substituent is hydroxy. Unsubstituted secondary and tertiary alkyl radicals are another preferred type.

In case Y is an aryl radical, it is preferably substituted or unsubstituted phenyl, most preferably phenyl.

Oxygen based heteroorganic radicals for Y are hydroxy, carbonyl, carboxylate, acyloxy, ether, more preferably hydroxy, ether carbonyl, acyloxy. Sulfur based heteroorganic radicals are thiyl and sulfonyl. Phosphorus based heteroorganic radicals are diarylphosphino, dihydrocarbylphosphate, dihydrocarbylphosphonate, dihydrocarbylphosphite. Nitrogen based heteroorganic radicals are amino and those of reduced basicity, i.e., amido, ureido, imido, amine oxide, bis-(hydroxyethyl) amine. Cyclic amido, such as N-2pyrrolidinonyl, is preferred.

Exemplary Y radicals are the following: trimethylsilyl, tripropylsilyl, triphenylsilyl, —diphenyl phosphine oxide, diisobutyl phosphine oxide, diphenyl phosphine, dihydroxypropyl phosphine, dipropyl phosphite, diphenyl phosphate, tributyl phosphonium benzene sulfonate, didecyldibutyl phosphonium tetraphenyl borate, benzyl dicyclohexyl phosphonium methane sulfonate—pyrryl, dimethylpyrryl, pyrrolidinonyl, morpholinyl, acetamido, benzamido, amido, carbamido, ureido, bis-hydroxyethylamino, —phenyl sulfone, fluorophenyl sulfone, ethyl sulfone, ethylthio, phenylthio—acetyl, benzoyl, carbomethoxy, benzoyloxy, carbobenzoxy, acetate, benzoate, phenylacetate, hydroxy, carbamate, phenoxy; i-propyl, phenoxyphenyl, diisobutyl, cyclopentyl, diisopropylamino, anilino, diphenylamino, furyl, mesityl, pentafluorophenyl, tetrahydronaphthyl tris(hydroxymethyl) methine.

In case Q is bound to a y+1 valent heteroorganic radical, E, the hydrocarbyl substituents of E are indicated by the symbol R''':

$(Ar_2PQER_{y'''})_hRh(CO)H$ and $(Ar_2P(CH_2)_mER_{y'''})Rh(CO)H$ wherein the meaning of Ar, Q h and m is the same as defined previously; E is the inorganic part of the heteroorganic radical, $ER_{y'''}$ is a noncharged, nonchelating heteroorganic radical selected from the group consisting of silane silicone, ether, ester, keto and hydroxy oxygen, phosphine and phosphorus ester phosphorus, amine, amide, amine oxide and heterocyclic nitrogen, sulfide and sulfone sulfur; and R''' is an independently selected $C_1$ to $C_{30}$, preferably $C_1$ to $C_{10}$, substituted or unsubstituted, preferably unsubstituted or monosubstituted, more preferably unsubstituted hydrocarbyl radical. R''' is preferably selected from the group of hydrocarbyl radicals consisting of $C_1$ to $C_6$ alkyl, $C_5$ and $C_6$ cycloalkyl, phenyl, $C_1$ to $C_6$ monosubstituted alkyl, monosubstituted phenyl. More preferably, R''' is $C_1$ to $C_6$ alkyl or phenyl. As such, the R''' groups include methyl, propyl, ω-trifluoropropyl, pentafluoropropyl, pentafluorophenylethyl, phenyl, cyclotetramethylene, tolyl, methylcyclopentyl, decyl, fluoropropyl, benzyl, cyclohexyl, fluoropentyl, methoxyethyl, tricosyl, hydroxyethyl, methoxyethoxyethyl. Further examples of R''' were given when listing examples of the Ar and R' hydrocarbyl groups.

A similar class of complexes possesses a positively charged rhodium moiety with the general formula $[(Ar_2PQY)_2Rh^+(CO)_3]X^-$ wherein all the symbols possess the previously defined meanings.

Another preferred class of compounds of the present invention include some of those compounds disclosed in our copending U.S. application Ser. No. 11,238 filed Feb. 12, 1979 now U.S. Pat. No. 4,298,541, of which the present application is a Continuation-In-Part. The particular trihydrocarbyl silyl substituted alkyl diaryl phosphine complexes thereof which are included within the scope of the present invention are those of the formula $[(Ar_2PQ)_bSiR_{4-b}]_g(RhX_n)_s$ wherein Ar, Q, b, R, g, X, n and s as defined above. Particularly preferred complexes within this class are complexes of the formulas $[(Ar_2P(CH_2)_m)_bSiR_{4-b}]_g[Rh(CO)H]_s$, $[(Ph_2PQ)_bSiR_{4-b}]_g[Rh(CO)H]_s$, $[Ph_2P(CH_2)_m)_bSiR_{4-b}]_g[Rh(CO)H]_s$, $((Ar_2P(CH_2)_m)_2Si(CH_3)_2]_3[Rh(CO)H]_2$ $(Ph_2PQSiR_3)_3Rh(CO)H$, $(Ph_2P(CH_2)_mSiR_3)_3Rh(CO)H$, $[(Ph_2P(CH_2)_m)_4Si]_3Rh(CO)H]_4$ $(Ar_2PQSiR_3)_2Rh^+(CO)_3G^-$, $[Ar_2P(CH_2)_mSiR_3]_2Rh^+(CO)_3G^-$, and $[Ar_2P(CH_2)_mSiR_3]_2Rh^+(CO)_3(BPh_4^-)$ wherein the symbols are as defined above. Particularly preferred compounds are $(Ph_2P(CH_2)_2Si(CH_3)_3)_3RH(CO)H$ $(Ph_2P(CH_2)_3Si(CH_3)_3)_3Rh(CO)H$ $(Ph_2P(CH_2)_2Si(C_3H_7)_3)_3Rh(CO)H$ $(Ph_2P(CH_2)_2SiPh_3)_3Rh(CO)H$ $((Ph_2PCH_2CH_2)_2Si(CH_3)_2)_3Rh(CO)H$ Still another preferred class of novel compounds within the scope of the present invention include those in which E represents a tertiary carbon group, i.e., catalysts of the formulae $[(Ar_2PQ)_bCR_{4-b}]_g \cdot (RhX_n)_s$ and $(Ar_2PQCR_3)_3Rh(CO)H$ wherein Ar, Q, R, X, b, g, n and s are as defined above. A particularly preferred class of such compounds include those of the formula $(Ph_2P(CH_2)_mCR_3)_3Rh(CO)H$ wherein m is an integer of from 1 to 30 and R is as defined above. Examples of such catalysts include $(Ph_2PCH_2C(CH_3)_3)_3Rh(CO)H$, $[Ph_2PCH_2CH_2C(CH_3)_3]_3Rh(CO)H$ and $(Ph_2PCH_2CH_2CH_2C(CH_3)_3)_3Rh(CO)H$.

A further preferred class of compounds within the scope of the present invention include keto substituted compounds of the formulas $[(Ar_2PQ)_bCR_{2-b}]_g \cdot (RhX_n)_s$ $(Ar_2PQCR)_3Rh(CO)H$ with C=O (keto)

and $(ArP(CH_2)_2CR)_3Rh(CO)H$ wherein Ar, Q, R, X, b, g, n and s are as defined above. Of such compounds particularly preferred are acyl compounds of the formula $$[Ph_2P(CH_2)_m\overset{O}{\underset{\|}{C}}R]_3Rh(CO)H$$

wherein m is an integer of from 1 to 30, especially from 2 to 14, and R is as defined above. Examples of such catalysts include $$(Ph_2PCH_2CH_2\overset{O}{\underset{\|}{C}}CH_3)_3Rh(CO)H,$$

$$(Ph_2PCH_2CH_2\overset{O}{\underset{\|}{C}}C_2H_5)_3Rh(CO)H$$

and $$[Ph_2PCH_2CH_2\overset{O}{\underset{\|}{C}}Ph]_3Rh(CO)H.$$

Catalysts having carbohydrocarbyloxy substituted phosphines are of the formulae $$[(Ar_2PQ)_b\overset{O}{\underset{\|}{C}}OR_{2-b}]_g\cdot(Rh(CO)H$$

$$(Ar_2PQ\overset{O}{\underset{\|}{C}}OR)_3Rh(CO)H$$

$$[Ar_2P(CH_2)_m\overset{O}{\underset{\|}{C}}O_2R]_3Rh(CO)H$$

$$[(Ar_2P(CH_2)_m\overset{O}{\underset{\|}{C}}OCH_2)_2)_3][Rh(CO)H]_2$$

and $$[Ph_2PCH_2CH_2\overset{O}{\underset{\|}{C}}O_2R]_3Rh(CO)H,$$

wherein Ar, Ph, Q, R, b, X, g, m, n and s are as defined above, represent another preferred class of compounds in accordance with the present invention. Particularly preferred are compounds of the formula $$(Ph_2P(CH_2)_m\overset{O}{\underset{\|}{C}}OR)_3Rh(CO)H$$

wherein m is an integer of from 2 to 22, especially from 4 to 14, and R is as defined above. Examples of compounds within this class include $$(Ph_2PCH_2CH_2\overset{O}{\underset{\|}{C}}OCH_3)_3RhH(CO)$$

and $$[(Ph_2PCH_2CH_2CO_2CH_2)_2]_3[Rh(CO)H]_2.$$

The corresponding acyloxy complexes are also included within the novel carboxylate substituted complexes of the present invention. These complexes are of the formula $$[(Ar_2PQ)_b\overset{O}{\underset{\|}{O}}CR_{2-b}]_g(RhX_n)_s$$

$$[Ar_2PQO\overset{O}{\underset{\|}{C}}R]_3Rh(CO)H$$

$$[Ar_2P(CH_2)_mO\overset{O}{\underset{\|}{C}}R]_3Rh(CO)H$$

$$[Ar_2PCH_2CH_2O\overset{O}{\underset{\|}{C}}Ph]_3Rh(CO)H$$

and $$[(Ar_2PCH_2CH_2O\overset{O}{\underset{\|}{C}}CH_2)_2]_3[Rh(CO)H]_2$$

wherein Ar, Q, R, X, b, g, n, m and s are as defined above. Exemplary of suitable compounds within this class is $$\{(Ph_2PCH_2CH_2\overset{O}{\underset{\|}{C}}CH_2)_2\}_3Rh(CO)H;$$

wherein Ph is phenyl.

Non-chelating trivalent nitrogen substituted complexes of the formula $$[(Ar_2PQ)_bNR_{3-b}]_g[RhX_n]_s$$

wherein Ar, Q, b, g, s, n, R and X are as defined above, represent another class of preferred compounds of the invention. These complexes include non-chelating open chain amino substituted alkyl diaryl phosphine complexes and nitrogen-containing heterocyclic ring substituted alkyl diaryl phosphine complexes. The latter include cyclic amides and imides. Preferred complexes within this class include amino substituted complexes of the formulas:

$$[(Ar_2PQ)_bNR_{3-b}]_g[Rh(CO)H]_s$$

$$[Ar_2PQN\quad R^4]_3Rh(CO)H$$

$$[Ar_2PQNR_2]_3Rh(CO)H$$

$$[Ar_2PQ-N\begin{matrix}R^5\\ \diagup\quad\diagdown\\ \diagdown\quad\diagup\\ R^6\end{matrix}O]_3Rh(CO)H$$

$$[Ph_2P(CH_2)_mN\overset{\overset{O}{\|}}{\boxed{\phantom{xx}}}]_3Rh(CO)H$$

$$[(AR_2PQ-N\begin{matrix}\diagup C_7\\ \\ \diagdown R^7\end{matrix}])_3Rh(CO)H$$

$$[Ar_2PQ-N\begin{matrix}\diagup C\diagdown^{\!\!\!O}\\ \\ \diagdown C\diagup R^8\\ \quad\diagdown_{\!\!\!O}\end{matrix}]_3Rh(CO)H$$

-continued

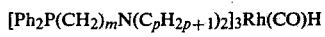

and

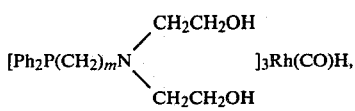

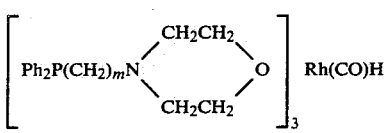

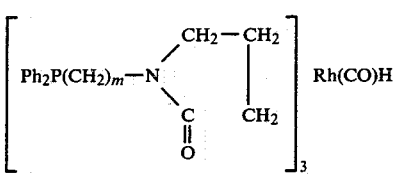

wherein Ar, Q, b, R, g, s, $R^4$, $R^5$, $R^6$, $R^7$, $R^8$ and Ph are as defined above and p is an integer of from 1 to 12.

Examples of such compounds include

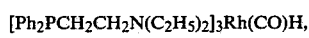

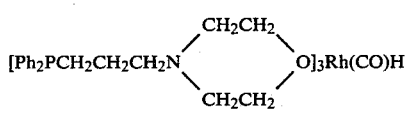

and

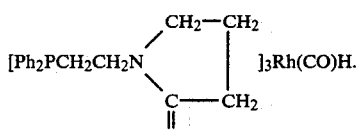

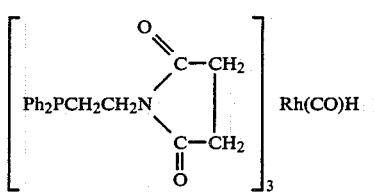

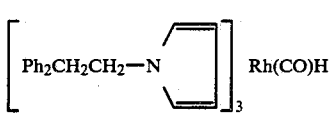

Another class of nitrogen-containing complexes of the invention are amide substituted open chain alkyl diaryl phosphine complexes of the formula

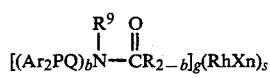

wherein Ar, Q, b, g, s, n, $R^9$, R and X are as defined above. Preferably, $R^9$ is H, an alkyl group containing 1 to 6 carbon atoms or phenyl. Preferred complexes within this class are of the formulas:

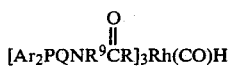

and $[Ph_2P(CH_2)_mNR^9\overset{O}{\overset{\|}{C}}R]_3Rh(CO)H$, wherein Ar, $R_9$, R, m and Ph are as defined above. Examples of such compounds are $(Ph_2PCH_2CH_2CONH_2)_3Rh(CO)H$ and $(Ph_2PCH_2CH_2CON(CH_3)_2)_3Rh(CO)H$.

The novel complexes of the invention also include carbamic acid derivatives of alkyl diaryl phosphine complexes of the formulae:

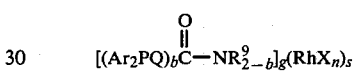

wherein Ar, Q, $R^9$, b, g, n, s and X are as defined above. Preferred complexes within this class include

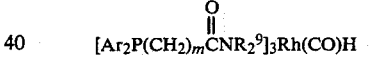

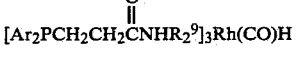

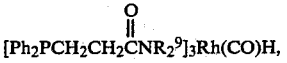

and $[Ph_2PCH_2CH_2\overset{O}{\overset{\|}{C}}NR_2^9]_3Rh(CO)H$, wherein the symbols have the above defined meanings. An example of such a compound is $(Ph_2PCH_2CH_2CN(CH_3)_2)_3Rh(CO)H$.

The novel compounds of the present invention also include trivalent phosphorus derivatives of the formula

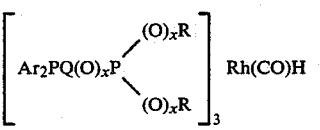

wherein Ar, Q, R, X, b, x, g, n and s are as defined above. Examples of such compounds include

[Ar₂PQOP(OR)₂]₃Rh(CO)H

[Ar₂P(CH₂)ₘOP(OR)₂]₃Rh(CO)H and ((Ar₂P(CH₂)ₘO)₃P)₃Rh(CO)H wherein Ar, Q, R and m are as defined above. A preferred complex is ((PH₂PCH₂CH₂CH₂O)₃P)₃Rh(CO)H.

The diaryl phosphine substituted derivative catalysts are non-chelating compounds of the formula

[Ar₂PQPAr₂]₃Rh(CO)H

[A₂P(CH₂)ₘPAr₂]₃Rh(CO)H

In the case of these compounds, m is 4 to 22, more preferably 6 to 14. Such compounds are

[Ph₂(CH₂)₄PPh₂]₃Rh(CO)H

[Ph₂(CH₂)₁₄PPh₂]₃Rh(CO)H

[Ph₂(CH₂)₆PPh₂]₃Rh(CO)H

Still another preferred class of compounds in accordance with the present invention include higher valent phosphorus derivatives of the formula $$\left[ (Ar_2PQ)_b(O)_x\!-\!\overset{\overset{O}{\|}}{\underset{\underset{(O)_x\!-\!R}{|}}{P}}\!\!\!\overset{(O)_x\!-\!R}{\diagup}\right]_g \cdot (RhX_n)_s$$

Preferred complexes within this class are $$(Ar_2PQPR_2)_3RhH(CO),$$

$$[Ar_2PQ\overset{O}{\overset{\|}{P}}(OR)_2]_3Rh(CO)H$$

$$[Ar_2P(CH_2)_m\overset{O}{\overset{\|}{P}}R_2]_3Rh(CO)H$$

$$\left\{(Ar_2P(CH_2)_m)_3\cdot\overset{O}{\overset{\|}{P}}\right\}_3 Rh(CO)H$$

$$[Ar_2P(CH_2)_m\overset{O}{\overset{\|}{P}}Ar_2]_3Rh(CO)H$$

$$[Ph_2P(CH_2)_m\overset{O}{\overset{\|}{P}}Ph_2]_3Rh(CO)H$$

and $$\left\{(Ar_2P(CH_2)_mO)_3\overset{O}{\overset{\|}{P}}\right\}_3 Rh(CO)H$$

wherein Ar, Q, R, X, b, x, g, n, Ph and s are as defined above. A preferred compound is of the formula $$[Ph_2P\text{\textrm{(}}CH_2\text{\textrm{)}}_{\overline{m}}\overset{O}{\overset{\|}{P}}R_2]_3Rh(CO)H$$

wherein m is an integer of from 1 to 30, especially from 2 to 14, and R is defined as above. One example of this type catalyst is $$(Ph_2PCH_2CH_2\overset{O}{\overset{\|}{P}}Ph_2)_3Rh(CO)H.$$

Still another group of novel compounds within the scope of the present invention are the sulfone derivatives of the formula

[(Ar₂PQ)ᵦSO₂R₂₋ᵦ]ᵧ(RhXₙ)ₛ wherein Ar, Q, R, b, g, n, s and X are as defined above. Preferred complexes within this class include complexes of the formulae

[Ar₂PQSO₂R]₃Rh(CO)H

[Ar₂P(CH₂)ₘSO₂R]₃Rh(CO)H ([Ar₂P(CH₂)ₘ]₂SO₂)₃[Rh(CO)H]₂ and

[Ar₂PCH₂CH₂SO₂R]₃Rh(CO)H wherein Ar, Q, R, X, b, g, n, m and s are as defined above. A specific example of a compound within this class is

[Ph₂CH₂CH₂SO₂C₂H₅]₃Rh(CO)H

Ether derivatives of alkyl diaryl phosphine complexes of the formula

[(Ar₂PQ)ᵦOR₂₋ᵦ]ᵧ(RhXₙ)ₛ wherein Ar, Q, R, g, b, n, s, and X are as defined above, form another class of the novel complexes of the invention. Preferred complexes within this class include complexes of the formulae:

[Ar₂PQOR]₃Rh(CO)H

[Ar₂P(CH₂)ₘOR]₃Rh(CO)H

[Ar₂P(CH₂CH₂O)₃CH₃]₃Rh(CO)H

[Ar₂PCH₂CH₂OCH₂CH₂OH]₃Rh(CO)H and ((Ar₂P(CH₂)ₘO)₃P)₃Rh(CO)H wherein Ar, Q, R and m are as defined above. Exemplary of suitable compounds within this class is

[Ph₂PCH₂CH₂OPh]₃Rh(CO)H.

Also included within the scope of the novel complexes in the invention are hydroxy derivatives of the formulas

[Ar$_2$PQOH]$_g$(RhX$_n$)$_s$ (Ar$_2$PQOH)$_3$Rh(CO)H

[Ar$_2$P(CH$_2$)$_m$OH]$_3$Rh(CO)H and

[Ar$_2$PCH$_2$CH(OH)CH$_2$OH]$_3$Rh(CO)H wherein Ar, Q, X, n, m, g and s are as defined above. Exemplary of a suitable compound within this class is

[Ph$_2$PCH$_2$CH$_2$CH$_2$OH]$_3$Rh(CO)H

Yet another class of novel compounds within the present invention are thioether derivatives of the formulae

[(Ar$_2$PQ)$_b$SR$_{2-b}$]$_g$Rh(CO)H

[Ar$_2$PQSR]$_3$Rh(CO)H and (Ar$_2$P(CH$_2$)mSR)$_3$Rh(CO)H wherein Ar, Q, R, X, b, g, n, m and s are as defined above. Exemplary of suitable compounds within this class is

[Ph$_2$PCH$_2$CH$_2$CH$_2$SPh]$_3$Rh(CO)H.

The diaryl alkyl phosphine ligands employed in the present invention are prepared by any number of standard techniques. One preferred synthesis technique involves the addition of diaryl alkyl phosphines to suitable unsaturated compounds:

bAr$_2$PH+[CH$_2$=CH—D]$_b$E$^y$R$_{y-b}$→[Ar$_2$PCH$_2$C-H$_2$—D]$_b$E$^y$R$_{y-b}$ or

[Ar$_2$PQ]$_b$E$^y$R$_{y-b}$ wherein CH$_2$=CHD— after the reaction represents the group Q as defined above. Thus, D can be a covalent bond or the remainder of the group Q other than —CH$_2$—CH$_2$—. Preferably —D— represents —CH$_2$—$_k$ wherein k ranges from 0 to 28, especially from 0 to 6 and most preferably from 0 to 1. Such additions are preferably carried out via a radical chain mechanism in a free radical manner. Chemical and/or radiation initiators can be used. It has been found that the selectivity of such reactions can be improved by using an excess of phosphine reactant, preferably from 5 to 100% excess over the stoichiometric amount required of the phosphine. A suitable chemical initiator for this process is a labile azo compound such as azo-bis-i-butyronitrile. The amount of the initiator can vary depending upon the chain length of the reaction and preferably is in the range of from about 0.1 to about 3%. The reaction temperature of a chemically initiated addition depends upon the temperature of initiating radical generation. This initiation normally occurs in the range of from 0° to 50° C.

For radiation initiation of the above-described addition reaction, ultraviolet light or gamma irradiation can be employed. The radiation intensity and duration are highly dependent upon the chain length, i.e., the G value. The preferred temperature of radiation initiation is between about —90° C. and +90° C.

The above-described radical addition of diaryl phosphines to certain substituted vinylic compounds is unexpectedly selective and fast. Such substituted vinylic compounds include vinyl silanes, vinyl ketones, N-vinyl amides, acrylates, and sulfones, as illustrated by the following formulas:

Ar$_2$PH+(CH$_2$=CH)$_b$SiR$_{4-b}$→(Ar$_2$PCH$_2$CH$_2$)$_b$SiR$_{4-b}$

Ar$_2$PH+CH$_2$=CHSiR$_3$→Ar$_2$PCH$_2$CH$_2$SiR$_3$

Ar$_2$PH+CH$_2$=CHNR$^9$COR→Ar$_2$PCH$_2$CH$_2$NR$^9$COR

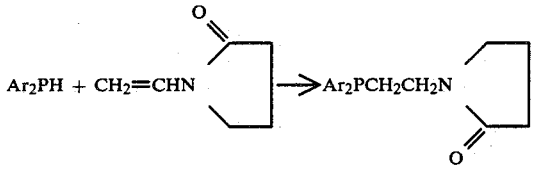

Ar$_2$PH+CH$_2$=CHCOR→Ar$_2$PCH$_2$CH$_2$COR

Ar$_2$PH+CH$_2$=CHCO$_2$R→Ar$_2$PCH$_2$CH$_2$CO$_2$R

Ar$_2$PH+CH$_2$=CHSO$_2$R→Ar$_2$PCH$_2$CH$_2$SO$_2$R

The high reactivity of these substituted vinylic compounds is contrasted with the sluggish behavior of some other substituted olefins having analogous structures, e.g., t-butyl ethylene.

It has also been observed that additions of phosphines to vinylic compounds wherein k=0 occur with ease in the presence of radiation particularly ultraviolet light. The reactivity of such vinyl compounds is in marked contrast to the rather sluggish behavior of olefins having analogous structures. In addition to such vinyl compounds, allyl compounds wherein k=1 are another preferred class of reactant.

Similar anti-Markovnikov additions can be carried out via anionic mechanism with base catalysis to certain conjugated vinylic compounds such as acrylates. Such anionic addition can be performed with either added base catalysis, e.g., a quaternary base addition, or without any base added in addition to the phosphine base.

Another technique which may be employed in the preparation of the alkyl diaryl phosphine ligands involved in the present invention is the addition of suitable hydrogen-containing compounds to unsaturated phosphines, preferably vinyl diaryl phosphines:

bAr$_2$P—D—CH=CH$_2$+H$_b$E$^y$R$_{y-b}$→[Ar$_2$P—D—CH$_2$—CH$_2$]$_b$E$^y$R$_{y-b}$ or

[Ar$_2$PQ]$_b$E$^y$R$_{y-b}$ wherein D is defined as above. Again, D preferably represents —CH$_2$—$_k$ wherein k is an integer of from 0 to 28. The preferred reactants are the vinylic and allylic materials, this time the phosphines. Thus, the heteroorganic substituted alkyl diaryl phosphines are derived by employing compounds such as secondary phosphine oxide, dihydrocarbyl hydrogen phosphites and thiols as the hydrogen-containing compound.

The above approach is exemplified by the free radical addition of secondary phosphine oxides, hydrogen phosphites and thiols:

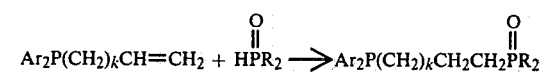

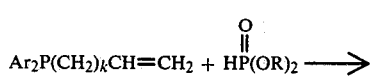

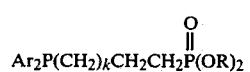

wherein Ar, k and R are as defined above. It is surprising that similar additions could not be carried out using silanes as adding agents. In general, the reaction conditions for the successful radical additions were those previously described for the diaryl phosphine olefin additions.

The method for preparing non-chelating bis-phosphines is described in the application of Alexis A. Oswald filed Jan. 23, 1980 entitled "Tetraalkyl Phosphonium Substituted Phosphine and Amine Metal Complexes and Processes for Use Thereof" now U.S. Pat. No. 4,302,401. That application also discloses methods for the synthesis of trialkyl phosphonium substituted alkyl diaryl phosphines and is incorporated herein by reference.

Other methods for alkyl diaryl phosphine ligand preparation employ displacement reactions. One type of reaction starts with diaryl phosphides, particularly alkali, metal phosphides, and suitable chloro-, bromo-, or iodo-alkyl compounds:

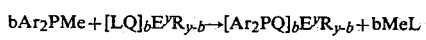

wherein Me is Na, K, Li and L is Cl, Br, I. Another technique starts with diaryl chloro or bromo phosphines and the corresponding Grignard derivatives of suitable alkyl compounds:

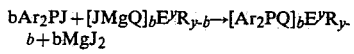

wherein J is chlorine or bromine and the other symbols are as defined above.

For the preparation of the present complexes, standard methods or organometallic chemistry are discussed in a comprehensive text, "Advanced Inorganic Chemistry," by F. A. Cotton and G. Wilkinson (Interscience Publishers, New York, 1972) and exemplified in the series on "Inorganic Syntheses" particularly Volume XV, edited by G. W. Parshall and published by McGraw-Hill Book Co., New York, 1974, and in U.S. Pat. No. 4,052,461 by H. B. Tinker and D. E. Morris, assigned to Monsanto Co.

For the preparation of the rhodium complexes, one of the specifically preferred direct methods of synthesis starts with rhodium chloride. This method can be employed, e.g., for the synthesis of tris-(alkyl diaryl phosphine) rhodium carbonyl hydride complexes according to the following general scheme:

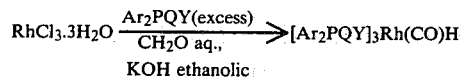

Other preferred direct methods of complex preparation include the reaction of transition metal carbonyls or oxides, such as those of rhodium with suitable diaryl alkyl phosphine ligand and CO/H$_2$. Similarly, organic salts of transition metals such as acetates can be reacted with the diaryl alkyl phosphine ligand.

According to one preferred method, the rhodium reactant is a rhodium salt, preferably rhodium trichloride or its hydrate. This method preferably employs a base, most preferably KOH or sodium borohydride, and a reducing carbonylating agent such as formaldehyde, hydrogen and CO to produce the carbonyl hydride complex via the tris-(alkyl diaryl phosphine) rhodium chloride and its carbonyl derivative intermediate compounds.

The complexes of the invention can also be prepared via an indirect method by reaction of the corresponding complexes of a triaryl phosphine, preferably triphenyl phosphine, with the desired diarylalkyl phosphine ligand, preferably in excess, e.g.:

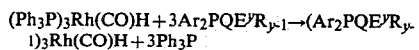

In general, the alkyl diaryl phosphine ligands are more basic than the corresponding triaryl phosphines. This basicity difference is a positive factor in the above ligand substitutions, providing completely or partially exchanged complexes, e.g.:

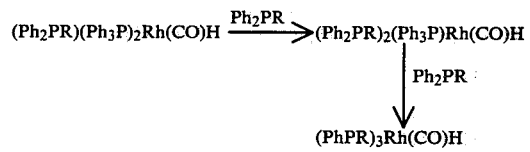

The formation of the tris(alkyl diaryl phosphine) rhodium carbonyl hydride complexes via ligand exchange can be followed by $^{31}$P nuclear magnetic resonance. $^{31}$P nmr can be also used for the identification and the quantitative determination of the starting alkyl diaryl phosphine reactants. As the ion exchange proceeds in an appropriate inert solvent, preferably aromatic hydrocarbon, $^{31}$P nmr shows the number and amounts of the different phosphine species. When an excess of the theoretically required alkyl diaryl phosphine reactant, preferably more than 100% excess, is used, the formation of the tris(alkyl diaryl phosphine) complex is essentially quantitative. The reaction temperature is between 10° and 100° C., usually ambient temperature.

Ligand exchange methods can be used for the preparation of the present complexes in situ, e.g., under hydroformylation conditions. For this purpose, the various rhodium carbonyls, and appropriate organic salts of rhodium carbonyl are particularly preferred. For example, dicarbonyl acetylacetonato (AcAc$^-$) dicarbonyl rhodium can be reacted with hydrogen and an excess amount of alkyl diaryl phosphine:

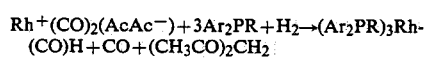

The synthesis and the physicochemical constants of most of the known phosphines is given in Volume 1 of a series of monograph, entitled "Organic Phosphorus Compounds," edited by G. M. Kosolapoff and L. Maier, published by J. Wiley and Sons, Inc., New York, N.Y., in 1972. Particularly, Chapter 1 on "Primary, Secondary and Tertiary Phosphines," by L. Maier, is relevant. Specifically, pages 33 to 105 and 135 to 224 provide the information on the certain tertiary phosphines used in the present invention. Chapter 3A, particularly pages 433 to 493, on "Phosphine Complexes with Metals" by G. Booth of the same volume also provides general information regarding phosphine rhodium complexes.

The novel complexes of the present invention have been found to be particularly useful in carbonylation reactions, particularly hydroformylation reactions, which involve the reaction of unsaturated organic compounds with CO, or CO and hydrogen mixtures. Carbonylation reactions are generally reactions of unsaturated organic compounds with carbon monoxide plus preferably a third reactant. Carbonylations are described in detail in the earlier referenced Falbe monograph. Main types of carbonylations catalyzed by the present complexes are the Roelen reaction (hydroformylation) of olefins with CO and $H_2$ and subsequent aldolization reactions: the Reppe reaction (metal carbonyl catalyzed carbonylation) mainly of olefins, acetylenes, alcohols and activated chlorides with CO alone or with CO plus either alcohol or amine or water; and ring closure reactions of functional unsaturated compounds such as unsaturated amides with CO. The unsaturated organic reactants are preferably olefinically unsaturated compounds, more preferably olefinic hydrocarbons.

The most preferred carbonylation is the improved, selective hydroformylation process of the present invention, however, the novel complexes of the invention can be employed as catalysts in other prior art methods to obtain good results.

The most preferred carbonylation is an improved, selective hydroformylation comprising reacting an olefin with a mixture of carbon monoxide and hydrogen in the presence of an alkyl diaryl phosphine halogen free rhodium complex as a catalyst to produce mainly an aldehyde, preferably via carbonylation at the less substituted vinylic carbon. Halogen free means that there is no reactive halogen, particularly chlorine, bonded to rhodium.

An improved method for hydroformylation was discovered comprising reacting an olefin with CO and $H_2$ in the presence of a tris- and bis-(alkyl diaryl phosphine) rhodium carbonyl complex catalyst free from halogen on the rhodium and excess free tertiary phosphine ligand wherein said improvement is effected by an appropriately high ratio of both $H_2/CO$ and ligand/Rh to produce a selective catalyst system of improved thermal stability and long term operational stability which leads to a ratio above four of n- and i-aldehyde primary products said products being the major primary products when the method employs a 1-n-olefin as starting reactant.

The preferred complex catalysts are nonchelating tris-(substituted alkyl diaryl phosphine) rhodium carbonyl hydride complex compounds of the formula:

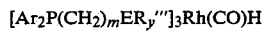

wherein the meaning of the symbols is as previously defined, except ER''' is a nonchelating heteroorganic radical, preferably being selected from the group consisting of silane silicone; ether, ester, keto and hydroxy oxygen; phosphine, phosphonium and phosphorus ester phosphorus; amine, amido, heterocyclic and ammonium nitrogen; sulfide and sulfone sulfur.

In hydroformylation reactions employing the novel complexes of the invention, organic nonhydrocarbon solvents, preferably of weak, nonsubstituting ligand character, are advantageously used. Preferred solvents of ligand character are triaryl phosphines, such as triphenyl phosphine, triaryl stibines, triaryl arsines. Other preferred organic solvents are ketones such as acetophenone, diphenyl ketone, polyethylene glycol and organic silicone compounds such as diphenyl dipropyl silane. More preferred ligand solvents are triaryl phosphines. Of course, the most preferred solvent is one used in the process of the present invention as described above containing an excess of an alkyl phosphine ligand, preferably the same alkyl diaryl ligand as complexed with the $(RhX_n)_s$ group. This last reaction system has been found to provide particularly advantageous results as explained in the following.

As far as other prior art carbonylation processes employing the present novel complexes are concerned such processes can be performed advantageously under the usual conditions such as those described in the earlier referenced Falbe monograph. Generally, the olefins described above can be employed in processes using the novel complexes of the invention. However, prior art processes employing the novel catalysts will normally have to be performed at higher temperature because although the novel complexes have greater stability and selectivity than triaryl phosphine complexes previously employed, the novel complexes generally provide relatively lower reaction rates. Typical total pressures, rhodium concentrations, ligand concentration and $H_2$ to CO partial pressure ratios for such prior art processes are Total pressure: 30 to 30,000 psi
Rh concentration: 10 to 10000 ppm
Ligand concentration: 100 to 200,000 ppm Moreover, in contrast to the process of the present invention, these prior art processes can employ an excess of any tertiary phosphine, including triphenyl phosphine. However, if the excess ligands include phosphines having structures other than that of the complexed diaryl alkyl phosphine, such ligand should not displace more than one of the three ligands of the novel tris-(diaryl alkyl phosphine) rhodium complex of the invention. The other complexing groups present in substituted alkyl diaryl phosphines should not effect such a multiple substitution either.

The novel complexes of the invention can also be employed in combined processes such as a combined hydroformylation/aldolization. For example, a process employing the normal prior art hydroformylation condition discussed above along with an aldol condensation catalyst and a novel complex of the invention would be one such process.

BEST MODE OF CARRYING OUT THE INVENTION

Figure 1:
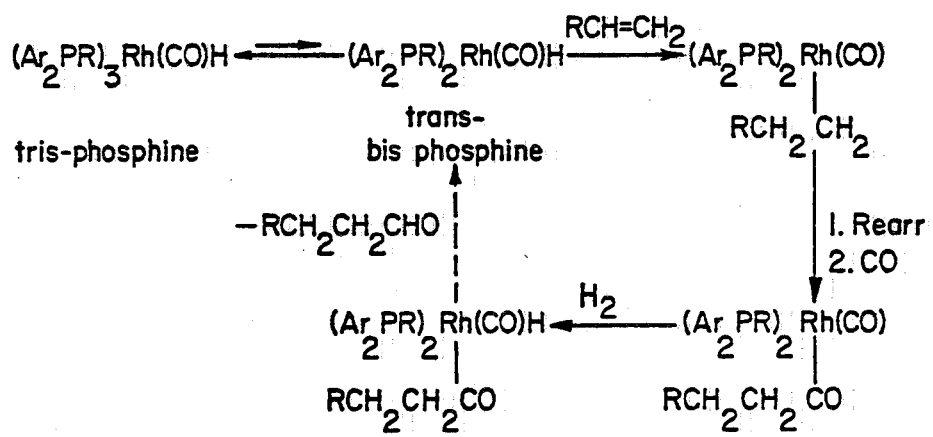
FIG. 1 shows the key steps in the mechanism of phosphine-rhodium complex catalyzed hydroformylation of olefins.

In accordance with another aspect of the present invention, it has also been discovered that diaryl alkyl phosphine complexed catalysts can be employed in a new hydroformylation process for the production of aldehydes from olefinic compounds and that highly advantageous results can be obtained thereby. Thus, the process of the present invention comprises reacting the olefinic compound with hydrogen and carbon monoxide in the presence of a reactive mixture comprising (1) a rhodium-containing catalyst having no reactive halogen and having at least one ligand complexed with said rhodium, wherein the complexed ligand comprises a complexed compound containing at least one diaryl phosphino alkyl group and wherein the number of such diaryl phosphino alkyl groups in complex association with said rhodium is at least two, and (2) a non-complexed ligand substantially all of which is a non-complexed compound containing at least one diaryl phosphino alkyl group, wherein the molar ratio of the non-complexed ligand to rhodium is greater than 100 and wherein the ratio of the partial pressures of hydrogen to carbon monoxide is at least 3:1.

The most preferred carbonylation is an improved, selective hydroformylation comprising reacting an olefin with a mixture of carbon monoxide and hydrogen in the presence of an alkyl diaryl phosphine halogen free rhodium complex as a catalyst to produce mainly an aldehyde, preferably via carbonylation at the less substituted vinylic carbon. Halogen free means that there is no reactive halogen, particularly chlorine, bonded to rhodium.

An improved method for hydroformylation was discovered comprising reacting an olefin with CO and $H_2$ in the presence of a tris- and bis-(alkyl diaryl phosphine) rhodium carbonyl complex catalyst free from halogen on the rhodium and excess free tertiary phosphine ligand wherein said improvement is effected by an appropriately high ratio of both $H_2/CO$ and ligand/Rh to produce an improved stability which leads to a ratio above four of n- and i-aldehyde primary products said products being the major primary products when the method employs a 1-n-olefin as starting reactant.

The preferred complex catalysts are nonchelating tris-(substituted alkyl diaryl phosphine) rhodium carbonyl hydride complex compounds of the formula

$$[Ar_2P(CH_2)_mER''']_3Rh(CO)H$$

wherein the meaning of the symbols is as previously defined, except ER''' is a nonchelating heteroorganic radical, preferably being selected from the group consisting of silane silicone; ether, ester, keto and hydroxy oxygen; phosphine, phosphonium and phosphorus ester phosphorus; amine, amido, heterocyclic and ammonium nitrogen; sulfide and sulfone sulfur.

As stated, such selective reactions were unexpectedly found to depend critically on the alkyl diaryl phosphine complex catalysts, the excess of phosphine ligand and the ratio of $H_2/CO$ synthesis gas reactant, i.e., the CO partial pressure. The selectivity also depends on the type of olefin employed. In an important embodiment of the new proces, the process is run on a continuous basis with the reaction being conducted at a temperature, olefin, $H_2$ and CO feed rates, a rhodium concentration and a rhodium to non-complexed ligand molar ratio effective to provide a rate of production of said aldehydes of at least about 0.1 g mole/l-hr, and wherein the ratio of the partial pressures of hydrogen to carbon monoxide is at least 3:1; and the aldehyde product is continuously removed as a vapor from the reaction mixture. Each of the above-described processes is hereinafter described as the process of the invention. In these processes, the CO partial pressure is preferably kept low, e.g., below 100 psi.

The process of the present invention has been found to provide a catalyst system having good thermal stability. Moreover, in the presence of a large excess of the diaryl alkyl phosphine ligand, the catalyst activity was surprisingly maintained while stability was increased. The process of the present invention was also found to provide unexpectedly good selectivity for producing n-aldehyde products from alpha-olefins.

In a preferred embodiment of the process of the present invention, the olefinic carbon compound is one containing an alpha-olefinic double bond. In this preferred process, the $H_2/CO$ ratio and the amount of the non-complexed compound containing at least one diaryl phosphino alkyl group are effective to provide an aldehyde product having a normal to iso isomer ratio of at least about 4:1. Again, it is preferable to maintain a low CO partial pressure.

In another embodiment of the process of the present invention, the reaction is preferably conducted at a temperature of at least about 90° C., a rhodium concentration of at least about 0.0001 molar and a non-complexed ligand to rhodium molar ratio of over 100. Also, the non-complexed ligand present in the reaction mixture preferably consists essentially of the non-complexed compound containing at least one diaryl phosphino alkyl group.

In yet another preferred embodiment of the process of the present invention, the L/Rh ratio, i.e., of the non-complexed compound containing at least one diaryl phosphino alkyl group to rhodium, is preferably above 120, more preferably above 240, and most preferably above 400. By raising the ligand to rhodium ratio when alpha-olefins are used in the process of the invention, higher normal to iso isomer ratios of the aldehyde product are obtained and accordingly, higher ligand to rhodium ratios are preferred in such cases. In a particularly preferred embodiment of the invention, the non-complexed ligand present during the reaction consists essentially of the non-complexed compound containing at least one diaryl phosphino alkyl group, and this ligand is present in a molar ratio, i.e., L/Rh of greater than 100.

Suitable complexed and non-complexed compounds containing at least one diaryl phosphino alkyl groups for use in the process of the invention include compounds of the following formula (which includes known diaryl alkyl phosphines as well as the novel substituted diaryl phosphino alkyl compounds which are exemplified by Formula I):

$$(Ar_2PQ)_b E^y R_{y-b}$$

wherein Ar is an aryl group containing from 6 to 10 carbon atoms;

Q is a divalent organic radical selected from an alkylene radical and an alkylene radical the carbon chain of which is interrupted with either oxygen or phenylene groups, wherein the alkylene radical contains from 2 to 30 carbon atoms;

E represents a member selected from a covalent bond,

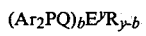

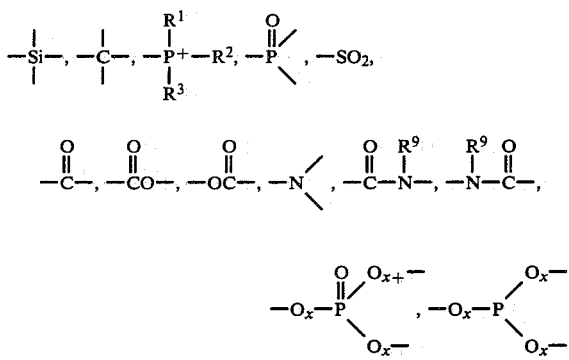

—O— and —S—, wherein $R^1$, $R^2$ and $R^3$ are each alkyl groups containing from 1 to 30 carbon atoms, wherein $R^9$ is a member selected from H, an alkyl group containing from 1 to 30 carbon atoms and an aryl group containing from 6 to 10 carbon atoms, and wherein X is an integer of 0 or 1 with the proviso that at least one x is 1;

y represents the valence bonds of the group E available for bonding to the groups Q and R (Thus, for a covalent bond, y is 2; for —Si—, y is 4; and for

y is 3.);

each R group independently represents a member selected from an alkyl group containing from 1 to 30 carbon atoms and an aryl group containing from 6 to 10 carbon atoms, and when E is —N<, R also represents a member selected from

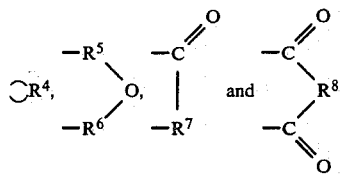

which member together with the N atom forms a heterocyclic ring, wherein $R^4$, $R^5$, $R^6$, $R^7$ and $R^8$ are hydrocarbyl radicals such that the heterocyclic ring contains from 5 to 6 atoms;

and b is an integer of from 1 to 4, provided that y-b is not less than zero. Preferably, the complexed and non-complexed compounds containing diaryl phosphino groups are of the formula

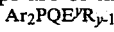

wherein Ar, Q, E, Y and R are as defined above.

Suitable complexed and non-complexed compounds containing diaryl phosphino alkyl groups which can be used in the process of the present invention include the known diaryl phosphino alkyl compounds discussed above in the section of the present specification entitled Background of the Invention, the tetraalkyl phosphonium substituted phosphine ligands disclosed in the U.S. Application entitled "Tetraalkyl Phosphonium Substituted Phospine and Amine Transition Metal Complexes and Processes For Use Thereof" filed on Jan. 23, 1980, now U.S. Pat. No. 4,302,401, in the name of Alexis A. Oswald, and the ligands of our novel catalysts discussed in detail above (i.e., of Formula I).

Non-chelating ligands of the formula

wherein Ar is aryl as defined above and m is an integer of from 4 to 14, represent yet another class of suitable complexed and non-complexed ligands.

The tetraalkyl phosphonium compounds as mentioned above represent still another class of ligands suitable for use in the process of the present invention. These phosphonium derivatives can be exemplified by the general formula

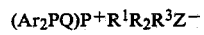

wherein Ar, Q, $R^1$, $R^2$ and $R^3$ are as defined above and $Z^-$ represents an anion. The $Z^-$ anion electrically neutralizes the ligand moiety; can be monovalent or polyvalent and is preferably a non-coordinating anion. Examples of suitable Z anions include halide, hydroxide, sulfate, sulfonate, phosphate, phosphonate, phosphite, tetraphenyl boride, fluorophosphate, carboxylate such as acetate, phenoxide and alkoxide. A particularly preferred subclass of such phosphonium ligands is of the formula $$Ph_2P-CH_2-{}_mP^+R^1R^2R^3Z$$

wherein m is an integer of from 1 to 30 and the other symbols are as defined above. These phosphonium ligands are also employed in complex association with rhodium as catalyst suitable for use in the process of the present invention.

Specific examples of such complexed and non-complexed compounds containing diaryl phosphino alkyl groups include ethyl diphenyl phosphine, propyl diphenyl phosphine, butyl diphenyl phosphine, $Ph_2PCH_2CH_2Ph$,

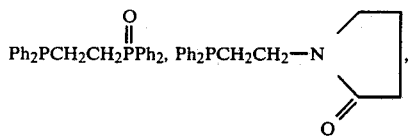

$Ph_2PCH_2CH_2COCH_3$, $Ph_2PCH_2CH_2CCCH_3$, $Ph_2PCH_2CH_2Si(CH_3)_3$, $Ph_2PCH_2CH_2C(CH_3)_3$, and $Ph_2PCH_2C(CH_3)_3$, wherein Ph here and through this specification and attached claims represents phenyl.

In yet another embodiment of the process of the present invention the rhodium-containing catalyst employed is of the general formula $$[(Ar_2PQ)_bE^yR_{b-y}]_g \cdot (RhX_n)_s$$

wherein Ar, Q, y, E, R and b are as defined above, X is an anion or organic ligand, excluding halogen, satisfying the coordination sites of the rhodium metal; g times b is 1 to 6; n is 2 to 6; and s is 1 to 3. Other preferred catalysts for use in the process of the present invention include rhodium-containing catalysts of the formulae:

$$[(Ar_2PQ)_bE^yR_{y-b}]_g \cdot [RhH(CO)]_s$$

and $$(Ar_2PQE^yR_{y-1})_3RhH(CO)$$

wherein Ar, Q, E, y, R, b, g and s are as defined above.

A preferred class of complexes suitable for use in the process of the present invention include complexes of the formula $$(Ar_2PQE^yR_{y-1})_3Rh(CO)H$$

and $$[(Ar_2PQ)_bE^yR_{y-b}]_g[Rh(CO)H]_s$$

wherein E represents a covalent bond or

R is an alkyl group, preferably a substituted or unsubstituted alkyl group containing 1 to 30 carbon atoms and more preferably a saturated open chain alkyl group; and Ar, Q, y and b are as defined above. Particularly suitable compounds within this class include compounds of the formula $$[Ar_2P{-}(CH_2{-})_mR]_3Rh(CO)H$$

wherein m is an integer of from 1 to 30, preferably from 2 to 22 and more preferably from 2 to 4; R is a straight-chain, branched or cyclic alkyl group or an aryl group such as isopropyl, tertiary butyl, cyclohexyl, or phenyl. A particularly suitable catalyst for use in the process of the present invention is $$(Ph_2PCH_2CH_2CH_3)_3Rh(CO)H.$$

Other examples of suitable catalysts for use in the present invention include $Rh(CO)H(Ph_2PCH_2CH_2Ph)_3$, $Rh(CO)H(Ph_2PCH_2CH_2PPh_2)_3$,

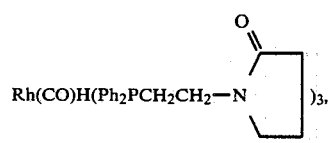

$Rh(CO)H(Ph_2PCH_2CH_2CCH_3)_3$, $Rh(CO)H(Ph_2PCH_2CH_2COCH_3)_3$, $Rh(CO)H(Ph_2PCH_2CH_2Si(CH_3)_3)_3$, $Rh(CO)H(Ph_2PCH_2CH_2C(CH_3)_3)_3$, and $Rh(CO)H(Ph_2PCH_2C(CH_3)_3)_3$.

The Ar, Q and R groups in the above-discussed ligands and complexes thereof can also be substituted with various substitutent groups. In general, the substitutents on the Ar, Q and R groups, and for that matter any substituent in the ligands and complexes used in the process of the present invention or in the novel complexes of the invention as set forth above in Formula I, are those which are chemically unreactive with the reactants used in and the products of the desired catalyzed reaction, e.g., a hydroformylation reaction. The same exemplary substituents can be used on any of the Ar, Q and/or R groups. Suitable substituents include halogen, carboxy, phenoxy, and hydroxy groups and also alkyl, alkoxy, acyl, acyloxy, acylamide, carbamido and carbohydrocarbyloxy groups containing from 1 to 30 carbon atoms, and preferably from 1 to 12 carbon atoms.

Suitable Ar groups for use in the complexed and non-complexed compounds or rhodium complexes thereof include aryl groups containing from 6 to 10 carbon atoms. The terminology "aryl group containing from 6 to 10 carbon atoms", as used in this specification and in the attached claims, is meant to include aromatic groups containing from 6 to 10 carbon atoms in the basic aromatic structure which structure can be substituted with any chemically unreactive substituent as discussed above. The aryl groups are also intended to include heterocyclic aromatic groups such as pyrryl, thienyl and furyl. The substituents on the aryl group, if any, are preferably bound to a phenyl group. Mono- and di-substituted phenyl groups are preferred. Thus, examples of suitable aromatic groups include phenyl, fluorophenyl, difluorophenyl, tolyl, xylyl, benzoyloxyphenyl, carboethoxyphenyl, acetylphenyl, ethoxyphenyl, phenoxyphenyl, biphenyl, naphthyl, hydroxyphenyl, carboxyphenyl, trifluoromethylphenyl, tetrahydronaphthyl, furyl, pyrryl, thienyl, methoxyethylphenyl, acetamidophenyl, and dimethylcarbamylphenyl.

Q in the above formulas represents a divalent organic radical selected from an alkyl group and an alkylene group the carbon chain of which is interrupted with ether oxygen or phenylene groups, wherein the alkylene group contains from 1 to 30 carbon atoms, preferably from 2 to 22 carbon atoms, and more preferably from 2 to 4 carbon atoms. The terminology "alkylene group", as used in this specification and in the attached claims, is meant to include an alkylene group containing 1 to 30 carbon atoms in the basic alkylene structure, which structure may again be substituted with any chemically unreactive substituent as discussed above. Examples of suitable Q organic radicals include ethylene, trimethylene, butylene, decamethylene, docosamethylene, tricontamethylene, phenyl bis(ethyl), ethylene bis-(oxyethyl), ethylene-bis oligo(oxyethyl), oxy ethyl propyl, oxy ethyl perfluoroethyl, oxy ethyl hydroxypropyl, xylylene and octadecamethylene. Preferably Q represents $-(CH_2)_m$ wherein m ranges from 1 to 30, preferably from 2 to 14, and most preferably from 2 to 4.

Suitable R groups for use in the above compounds include aryl groups containing from 6 to 10 carbon atoms and alkyl groups containing from 1 to 30 carbon atoms and when E is $-N<$, R can also represent a member selected from

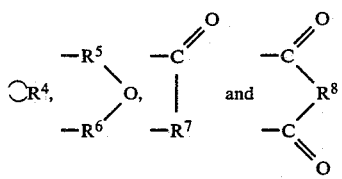

which member together with the N atom forms a heterocyclic ring, wherein $R^4$, $R^5$, $R^6$, $R^7$ and $R^8$ are hydrocarbyl radicals such that the heterocyclic ring contains from 5 to 6 atoms. These R groups may again be substituted with substituents that are chemically unreactive as discussed above. Suitable R aryl groups include any of those mentioned above in the definition of suitable Ar groups. By the terminology "alkyl group containing from 1 to 30 carbon atoms", we mean to include alkyl groups containing from 1 to 30 carbon atoms in the basic alkyl structure, which can be straight-chain, branched or cyclic and which can be substituted with any chemically unreactive substituent as discussed above. The alkyl groups are preferably primary or secondary alkyl groups, more preferably primary alkyl groups containing from 2 to 22 carbon atoms, and even more preferably from 6 to 14 carbon atoms. Exemplary alkyl groups include methyl, ethyl, propyl, n-butyl, iso-butyl, t-butyl, n-hexyl, cyclohexyl, methylcyclopentyl, isopropyl, decyl, fluoropropyl, docosyl, triacontyl, cyclopentyl, phenyl, methoxyethoxyethyl, acetylethyl, tris-hydroxy substituted t-butylethyl, triphenylmethylethyl, hydroxypropyl, carbomethoxyethyl, phenoxyethyl, benzamidoethyl, benzoyloxyethyl, pyrrylethyl, furylethyl and thienylethyl.

X in the above formulae represents an anion or organic ligand which satisfies the coordination sites of the rhodium metal, preferably a non-coordinating anion. Suitable X groups include $H^-$, $alkyl^-$, $aryl^-$, substituted $aryl^-$, $CR_3^-$, $C_2F_5^-$, $CN^-$, $N_3^-$, $COR^-$, $PR_4^-$, (where R is alkyl or aryl), carboxylate such as acetate, acetylacetonate, $SO_4^{2-}$, sulfonate, $NO_2^-$, $NO_3^-$, $O_2^-$, $CH_3O^-$, $CH_2=CHCH_2^-$, $CO$, $C_6H_5CN$, $CH_3CN$, $NO$, $NH_3$, pyridine, $(C_4H_9)_3P$, $(C_2H_5)_3N$, chelating olefins, diolefins and triolefins, tetrahydrofuran, $CH_3CN$, and triphenyl phosphine. Preferred organic ligands are readily displaceable such as carbonyl, olefins, tetrahydrofuran and acetonitrile. The most preferred X ligands are CO and H.

The preferred olefin reactants for use in the hydroformylation process of the present invention and other hydroformylation processes employing the novel complexes of the present invention are ethylene and its mono- and disubstituted derivatives. The formula of the preferred compounds is shown in the following representation of the hydroformylation reaction:

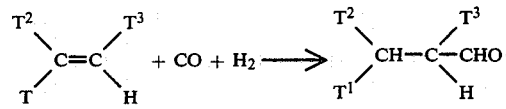

wherein $T^1$, $T^2$ and $T^3$ are independently selected from hydrogen and organic radicals containing from 1 to 1000 carbon atoms, preferably from 1 to 40 carbon atoms, more preferably from 1 to 12 carbon atoms, and most preferably from 4 to 6 carbon atoms, with the proviso that at least one of $T^1$, $T^2$ or $T^3$ be hydrogen. These radicals can be unsubstituted or substituted, but preferably they are unsubstituted.

As such, the preferred olefins include symmetrically disubstituted, i.e., internal, olefins of the formula

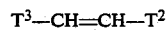

wherein the meanings of $T^3$ and $T^2$ in this case is the same as above except that they exclude H. Other, particularly preferred olefins are mono- and disubstituted unsymmetrical olefins of the formula

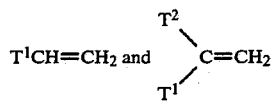

wherein the meaning of $T^1$ and $T^2$ in this case also excludes hydrogen. The monosubstutited olefins are particularly preferred. Such specifically preferred olefins are propylene, 1-butene, 1-pentene, 1-hexene, 1-heptene, 1-octene. The unsubstituted parent compound, ethylene, is also a specifically preferred reactant.

As far as the terminal versus internal attack of unsymmetrically substituted olefins is concerned, the disubstituted compound is a highly specific reagent in hydroformylation. It leads to mostly terminal or so-called n-aldehydes:

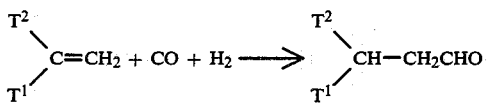

Specifically, preferred reagents of this type are isobutene, 2-methylbutene, 2-methylpentene, 2-ethylhexene.

In contrast to these disubstituted alpha-olefins, the selectivity of the hydroformylation of unsymmetrically monosubstituted olefins in the process of the present invention and other processes employing our novel complexes as set forth and fully explained further below depends on the excess phosphine concentration and CO partial pressure. The preferred course of the reaction is via terminal attack on the olefin to produce the corresponding n- rather than i-aldehydes:

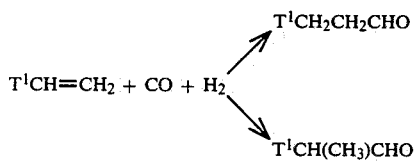

The size, i.e., steric demand of the $T^1$ substituent, also affects the selectivity. In the case of propylene, having the small methyl group for $T^1$, the selectivity to the n-product is relatively small. 1-Butene, with ethyl for $T^1$, is hydroformylated with surprisingly higher selectivity. 3-Methyl-1-butene, where $T^1$ equals i-propyl, reacts even much more selectively. Apparently, the bulkier and more branched $T^1$ groups hinder the attack on the internal, beta-vinylic carbon. The preferred monosubstituted olefins are n-1-olefins, wherein $T^1$ is n-alkyl. Particularly preferred reactants are 1-butene and propylene.

Exemplary olefinic reactants for use in the process of the present invention can be of open chain or cyclic structure. There can be a multiplicity of double bonds present in the higher molecular weight reactants. However, diolefin and polyolefin reactants of nonconjugated character are preferred. The saturated carbon atoms of these olefins can have non-hydrocarbon substituents such as hydroxy, carbonyl, carboxylate, ester, alkoxide, acetal and fluorine groups. Of course, these substituents must not react with the components or the products of the hydroformylation reaction systems. Suitable cyclic olefins or olefins having a multiplicity of double bonds include 1-hexadecene, 3-hexene, cyclohexene, 1,7-octadiene, 1,5-cyclododecadiene, methyl cyclopentene, 1-tricosene, 1,4-polybutadiene, methyl oleate, ethyl 10-undecanoate, 3-butenyl acetate, diallyl ether, allyl fluorobenzene, 6-hydroxyhexene, 1-hexenyl acetate, 7-heptenyl diethyl acetal, norbornene, dicyclopentadiene, methylene norbornene, trivinyl cyclohexane, allyl alcohol.

While we do not wish to be limited by any theory by which the process of the invention and our novel complexes work, it is believed that in solution and particularly under reaction conditions, both the tris- and bis-phosphine rhodium complexes are present. It was found via $^{31}P$ nmr studies that the widely accepted equilibration mechanism of tris- and bis-phosphine rhodium carbonylhydride complexes occurs according to the reaction formula:

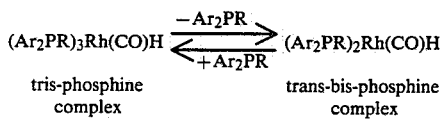

tris-phosphine complex     trans-bis-phosphine complex

Figure 3:
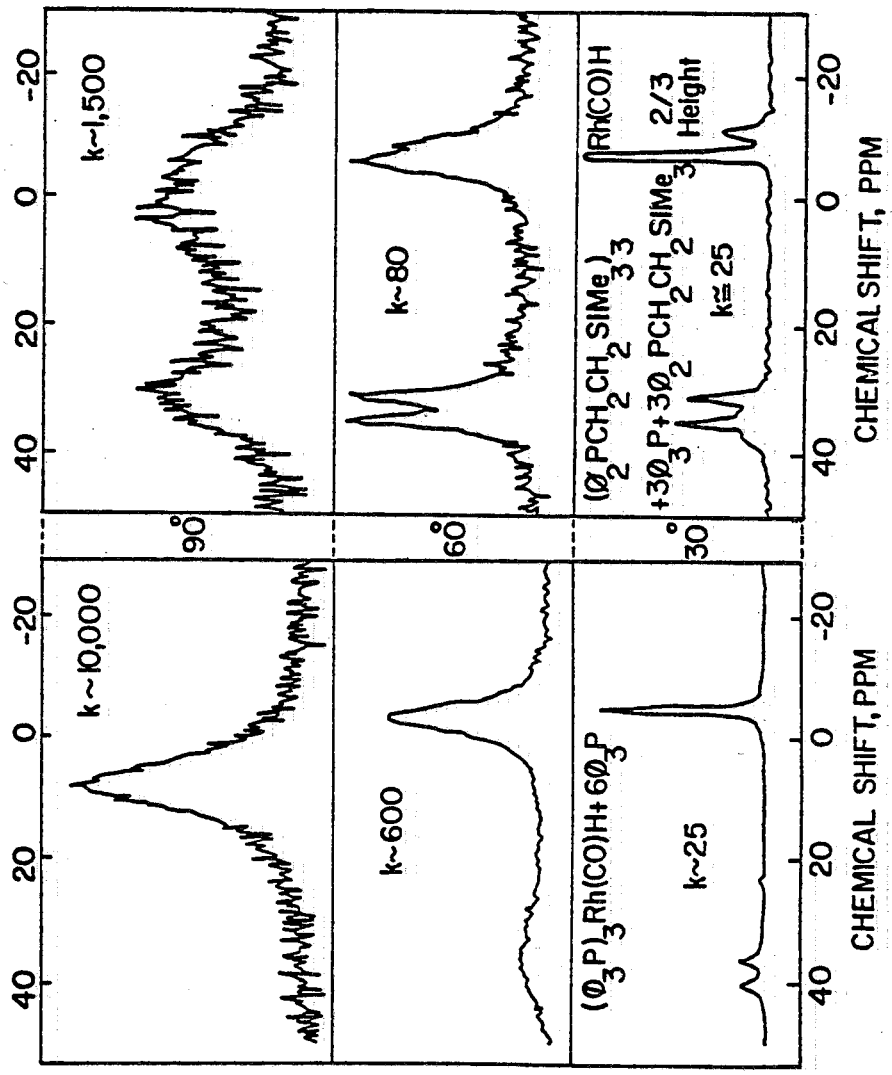
FIG. 3 illustrates a $^{31}$P NMR study of certain ligand exchange rates as a function of temperature.

The overall mechanism of hydroformylation catalysis of the present complexes is shown by FIG. 1. In FIG. 3, there is shown a side-by-side comparison of the $^{31}P$ nmr spectra at 30°, 60° and 90° C. for solutions containing, on the one hand, $(Ph_3P)_3Rh(CO)H$ and $Ph_3P$ (TPP) as excess ligand, and on the other hand, containing $(Ph_3P)_3Rh(CO)H$ and excess $Ph_2PCH_2CH_2Si(CH_3)_3$ ligand (SEP ligand) as starting materials.

Equilibration of the stable tris-phosphine complex to provide some of the highly reactive, coordinatively unsaturated trans-bis-phosphine is to occur in an active catalytic system. However, in the case of stable catalysts, most of the rhodium is present in the stable tris-phosphine complex form.

FIG. 3 also shows that the line shapes of the signals of the 30° C. spectra of both systems showed little signal broadening in both cases. This indicated comparably slow exchange rates of about 25 per second. In alternative terms, relatively long average exchange lifetimes, in the order of $2 \times 10^{-2}$ sec, were indicated for both complex systems tested. At 60° C., considerable line broadening occurred, indicating a much faster exchange. The exchange acceleration was greater in the case of the excess triphenyl phosphine ligand system (k=600 vs. 80), indicating an average lifetime of about $3 \times 10^{-3}$ sec for the excess triphenyl phosphine ligand system and of about $6 \times 10^{-3}$ sec for the excess trimethylsilylethyl diphenyl phosphine ligand system. At 90° C., only a single, broad signal could be observed for the excess triphenyl phosphine ligand system, while the excess trimethylsilylethyl diphenyl phosphine ligand system still exhibited separate, although extremely broad, chemical shift ranges for the complexed and free phosphorus species. Apparently, the exchange acceleration in the case of the excess triphenyl phosphine ligand system was tremendous at 90° C. with the average lifetime between exchanges being reduced by about two orders of magnitude to $5 \times 10^{-5}$ sec (k=10,000). In the case of the excess trimethylsilylethyl diphenyl phosphine ligand system, the average lifetime dropped by about one order to $5 \times 10^{-4}$ sec (k=1,500). It must be emphasized that the exchange rates and lifetimes may change somewhat when the lineshape is subjected to a rigorous computer analysis. The relative order of their values will remain unaltered, however.

It is interesting to note that there was no great change of equilibria with the increasing exchange rates. Apparently, both ligand elimination and addition increase similarly in this temperature range. The tris-phosphine rhodium species remained the dominant form of complexes. However, in the triphenyl phosphine complex system including free excess trimethylsilylethyl diphenyl phosphine ligand, the rhodium predominantly complexed with the SEP ligand.

The role of excess phosphine ligand is apparently to maintain the equilibria in favor of the tris-phosphine complex, i.e., to reduce both the concentration and average lifetime of the unstable and highly reactive bis-phosphine complex. The increased ligand exchange rate provides enough active bis-phosphine complex catalytic species for fast hydroformylation, without leading to non-catalytic side reactions, i.e., catalyst decomposition.

Our comparative $^{31}P$ nmr studies of the known TPP catalyst plus excess TPP ligand system showed that it has a mechanism similar to that of the SEP system of the invention; however, the thermal activation and catalyst destabilization of the TPP system occurs at lower temperatures than for the SEP system. In other words, the tris-(alkyl diaryl phosphine) rhodium carbonyl hydride plus excess alkyl diaryl phosphine-based systems of the present invention are surprisingly improved high temperature hydroformylation catalysis systems.

The results of $^{31}P$ nmr studies of tris-phosphine rhodium complex formation where also correlated with catalyst activity. It was found that those alkyl diphenyl phosphines which do not form trio-phosphine complexes for steric reasons are not suitable ligands for the present selective catalysts. Also, it was found that substitution of the alpha-carbon and multiple substitution of the beta-carbon of the Q alkylene group and o,o'-substitutions of the Ar aryl groups of the ligands used in the process of the present invention generally interfere with the complexation, i.e., the desired catalyst formation.

Common five and six membered chelate type complexes of alkylene bis-phosphines, e.g.,

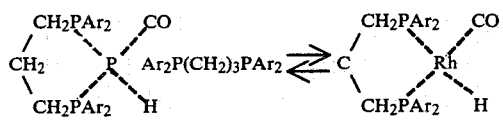

are not acceptable selective catalyst ligands either according to the concept of the process of the present invention, because they form bis-phosphine complexes of cis- rather than trans-configuration.

In the process of the present invention, substantially all of the excess phosphine ligand is an alkyl diaryl phosphine, preferably a phosphine ligand identical with that of the complex. Preferably, from about 1 to 90% by weight of the excess phosphine ligand is a diaryl alkyl phosphine and more preferably from about 5 to 50% by weight is a diaryl alkyl phosphine. In another preferred embodiment, the excess phosphine ligand consists essentially of an alkyl diaryl phosphine. By the terminology "consists essentially of" as used in this specification and in the claims attached hereto, we mean that only small amounts of non-diaryl alkyl phosphine ligand are present which will not affect the stability and selectivity of the catalyst system, e.g., such amount as might be present by forming the rhodium complex in situ starting with tris-(triphenyl phosphine) carbonyl hydrido rhodium complex and, as the sole excess ligand, a diaryl alkyl phosphine such as SEP or diphenyl propyl phosphine.

The rhodium complex catalysts are obviously very expensive due to the high cost of rhodium. As such, in the process of the present invention and in other processes employing the novel rhodium complexes of the invention, the rhodium complex concentration is to be carefully selected to be most effective on a rhodium basis. Of course, a catalytically effective amount of the rhodium will be present.

The preferred concentration of the rhodium complex as used in the process of the present invention and in other processes employing the novel rhodium complexes of the invention is in the range of $1 \times 10^{-6}$ to $1 \times 10^{-1}$ mole of rhodium per mole of olefin reactant. More preferred concentrations are in the range of $1 \times 10^{-5}$ to $1 \times 10^{-1}$ mole of rhodium per mole of olefin and the most preferred range is $1 \times 10^{-4}$ to $1 \times 10^{-2}$ mole of rhodium per mole of olefin. Thus, the preferred rhodium concentration is normally in the range of from 10 to 1000 ppm. However, the preferred catalyst concentrations are directly affected by the concentration of free ligand present, especially the excess diaryl alkyl phosphine ligand. Since the excess phosphine reduces the concentration of the active bis-phosphine complexes, a larger excess reduces the effectiveness of the total rhodium complex present. The higher the ligand concentration, the higher the rhodium level required for a certain reaction rate. Nevertheless, a high phosphine concentration is employed in the process of the invention to achieve the desired catalyst stability and selectivity.

In the process of the invention, the minimum weight percent amount of excess ligand in the reaction medium is preferably about 1 wt.%, more preferably 5 wt.%. However, in general, the phosphine concentration is limited to 50 wt.% of the reaction mixture. At an appropriate rhodium concentration, the reaction can be carried out using the excess diaryl alkyl phosphine as the solvent. Sufficient excess diaryl alkyl phosphine concentration is used in the preferred process to carry out the reaction at the desired temperature under the desired conditions with the desired selectivity and activity maintenance. The rhodium complex concentration can then be adjusted to achieve the desired reaction rate.

Due to the interdependence of the alkyl diaryl phosphine rhodium complex and the excess phosphine ligand in the process of the invention, the mole ratio of diaryl alkyl phosphine ligand to mole equivalent rhodium complex, L/Rh, is preferably in the range of from about 40 to about 3000. The L/Rh ratio is preferably above 120, more preferably about 240, most preferably above 400. In general, higher ratios are selected when the desired operation is a continuous rather than a batchwise operation.

The selectivity of the process of the present invention is also dependent on the molar ratio of gaseous CO and $H_2$ reactants. This $H_2/CO$ ratio should be greater than 3:1 preferably in the range of 200:1 to 3:1 and more preferably, from 100:1 to 5.5:1 and most preferably from 20:1 to 10:1.

The present process of the invention is also operated at surprisingly low pressures, but can be operated at pressures of from 1 to 10,000 psi. The preferred pressures are between about 1 and 1000 psi, i.e., about 1 and 68 atm. It is more preferred to operate between about 25 and 500 psi, i.e., about 2 and 34 atm.

Some of the above pressure limitations are due to the sensitivity of the present rhodium complex catalyst to the partial pressure of CO. The total partial pressure of CO is preferably less than about 200 psi (approximately 8 atm.), more preferably less than about 100 psi, and most preferably less than about 50 psi. If the CO partial pressure is too high, the catalyst complex is deactivated due to the formation of carbonyl derivatives.

In the process of the present invention, the partial pressure of hydrogen has no critical upper limit from the viewpoint of hydroformylation. Nevertheless, the preferred partial pressure of hydrogen is between about 50 and 500 psi, i.e., 4 and 34 atm. Above a certain partial pressure of hydrogen, the relative rates of competing hydrogenation and isomerization reactions suddenly increase, which is to be avoided in the process of the present invention. However, if such hydrogenation and isomerization reactions are desired, the novel complexes of the invention are surprisingly active hydrogenation and isomerization catalysts. In the latter case, the rhodium complex of the invention becomes a multifunctional catalyst when the $H_2/CO$ ratio is too high and/or the CO concentration is insufficient.

When working with a terminal olefin, the selectivity to paraffin and internal olefin was sometimes significantly increased for the above reasons. For example, the reaction of 1-butene led not only to n- and i-valeraldehydes, but also to significant amounts of n-butane and cis- and trans-2-butenes. This effect of high hydrogen partial pressures becomes particularly critical under non-equilibrium conditions where the system is starved of CO. In such a case, practically only the n-aldehyde plus by-products are formed. In a preferred mode of operation, the optimum combination of reaction parameters is maintained by assuring equilibrium conditions by appropriate reactant introduction and mixing.

In the upper temperature range of the process of the invention, a significant part of the total pressure can be maintained by either a volatile reactive or unreactive olefin or a saturated, aliphatic or aromatic hydrocarbon or by an inert gas. This preferred mode of operation allows a limitation of synthesis gas pressure, while assuring a higher solubility of the gaseous reactants in the liquid reaction mixture.

The operation of the process of the invention can be optimized in a surprisingly broad temperature range. The range of temperature is preferably between 50° and 200° C., more preferably, between 90° and 175° C., and most preferably, between 120° and 150° C. Compared to prior art catalyst systems employing triphenyl phosphine, the maintenance of the catalyst activity and selectivity at the higher temperatures in the process of the present invention is particularly unique. High rates of selective hydroformylation of alpha-n-olefins can be realized and maintained to high conversion at 145° C. when using the present process conditions.

The process of the invention can be carried out either in the liquid or in the gaseous state. The catalyst can be employed as such either dissolved in the liquid reaction medium or deposited on a suitable solid such as silica or alumina. The preferred process employs a liquid, more preferably homogeneous liquid, reaction phase with the catalyst system dissolved, i.e., homogeneous catalyst.

The preferred homogeneous catalysis process of the invention is affected by the solvents used although a large variety of organic solvents is employable. In general, the more polar solvents of higher dielectric constant are increasingly preferred as long as they possess sufficient solvent power for the olefin reactant and do not interfere with the stability of the desired catalyst complex species. As such, aromatic hydrocarbons are suitable solvents, although organic nonhydrocarbon solvents are preferably used. More preferably, the latter are of a weak non-substituting ligand character. As such, oxygenated solvents are most preferred.

Preferred solvents include those of ligand character, e.g., diaryl alkyl phosphine, or organic solvents, e.g., ketones such as acetophenone, diphenyl ketone; polyethylene glycol; organic silicone compounds such as diphenyl dipropyl silane; esters such as 2-ethylhexyl acetate, dipropyl adipate, ethylene glycol diacetate; 1,4-butane diol; dimethyl formamide; N-methyl pyrrolidinone 4-hydroxybutyl 2-ethylhexanoate. One of the most preferred solvents is an excess of the alkyl diaryl phosphine ligand.

In general, the preferred solvents for the process of the invention, particularly ligands, stabilize the catalyst system and increase its selectivity, particularly as to the ratio of linear versus branched products. The aldehyde product of the invention is generally an excellent solvent. Accordingly, the addition of a separate solvent is not required.

In contrast to the disclosure on the triphenyl phosphine type rhodium complex catalyst system of the previously discussed U.S. Pat. No. 4,148,820 by Pruett and Smith, the alkyl diaryl phosphine rhodium complex catalyst systems used in the process of the present invention and the novel rhodium complexes of the invention are compatible with, i.e., soluble in, a large variety of organic solvents. These solvents include the aldehyde trimer condensation products which, according to Pruett and Smith, are the only suitable solvents for the triphenyl phosphine type based rhodium catalyst system.

Due to the improved stability provided by the process of the present invention employing alkyl diaryl phosphine rhodium complex catalysts, a continuous mode of operation is often advantageous. When using a homogeneous liquid catalyst system, such an operation can be of a continuous plug flow type, including a step for catalyst recovery and then recirculation. The process of the present invention may also involve a quasi-continuous use of the catalyst employing the cyclic operation of a unit for hydroformylation and then for product flash-off. Catalyst concentration or other methods of catalyst recovery may involve complete or partial recycle. However, a preferred method of operation for the process of the present invention involves continuous product flashoff.

In the continuous product flashoff process of the present invention, the aldehyde product of the hydroformylation is continuously removed as a component of a vapor mixture, while the CO, $H_2$ and olefin reactants are continuously introduced. This process preferably includes the recirculation of most of the unreacted reactants in the gaseous state and the condensation and thereby removal of most of the aldehyde and aldehyde derivative products. Additional olefin, CO and $H_2$ are added as required to maintain aldehyde production and optimum process parameters. The space velocity of the gas stream is appropriately adjusted and additional gas purge is used as required to maintain production and catalyst activity. Since the rhodium complex is not volatile, no catalyst losses occur. If the diaryl alkyl phosphine ligand is volatile, additional phosphine is added occasionally to maintain its concentration in the reaction mixture.

During the continuous product flashoff operation, relatively non-volatile aldehyde oligomers are formed and concentrated in the liquid reaction mixture. The oligomeric hydroxy substituted carboxylic ester condensation and redox disproportionation products formed during propylene hydroformylation were disclosed in the previously discussed U.S. Pat. No. 4,148,820 of Pruett and Smith. In the present work, it was found that analogous derivatives, mainly trimers, are formed during 1-butene hydroformylation. The general structure of the isomeric trimers is the following:

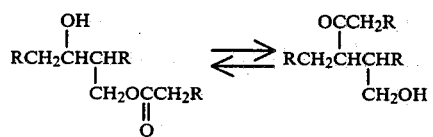

wherein R is $C_2$ to $C_5$, preferably $C_3$, alkyl.

The above aldehyde trimer is generally the main derivative and at equilibrium conditions of a preferred continuous flashoff process of the present invention, it can automatically become the main solvent component. When this occurs during 1-butene hydroformylation in accordance with the process of the present invention, selectivity and production rate can be maintained and the concentration of the trimer can be limited to an equilibrium value.

In the continuous product flashoff operation of the process of the present invention, carbonylations, especially the hydroformylation of olefins, are advantageously carried out at a low olefin conversion, preferably at a 20 to 80% olefin conversion. Aldehyde production rates are preferably between 0.1 and 5 g mole/liter/hour, more preferably between 0.5 and 2 g mole/liter/hour. Operating in this manner with optimized reactant ratios, particularly high linear to branched aldehyde product ratios are obtained from alpha-n-olefins.

The continuous process of the present invention can be also employed for the selective or complete conversion of different types of olefins. For example, a mixture of 1- and 2-butenes can be hydroformylated to produce mainly n-valeraldehyde and 2-butene. Similarly, a mixture of 1-butene, 2-butene and i-butene can be converted selectively to varying degrees.

Using the process of the present invention, the catalysts have improved thermal stability and thus the application of continuous for batch flashoff processes can be extended to higher olefins leading to aldehyde products which are not sufficiently volatile at the normal lower temperatures used in previous continuous operations. The preferred olefins for continuous product flashoff are of the $C_2$ and $C_6$ range and alpha-n-olefin type. 1-Butene and propylene are particularly preferred.

Using the present catalysts of improved thermal stability, the application of continuous or batch flashoff processes can be extended to higher olefins leading to nonvolatile products. The preferred olefins for continuous product flashoff are of the $C_2$ to $C_6$ range and n-1-olefin type. 1-Butene is a particularly preferred reactant.

In an improved method for continuous hydroformylation, 1-butene is reacted with CO and $H_2$ in the presence of a tris-(2-trimethylsilylethyl diphenyl phosphine) rhodium carbonyl hydride complex and excess 2-trimethylsilylethyl diphenyl phosphine ligand based catalyst system wherein the reactants are continuously introduced into a liquid reaction mixture comprising dissolved catalyst and ligand and preferably major amounts of n-valerladehyde trimer, and wherein the aldehyde products are continuously removed in the vapor phase, and wherein some of the reactants are recirculated. The improvement is effected by having the carbon monoxide partial pressure between about 4 and 100 psi, preferably between about 80 and 70 psi; the hydrogen partial pressure, preferably between about 5 and 500 psi; and the total gas pressure between 25 and 500 psi; preferably between 55 and 500 psi; a rhodium complex concentration between $1\times10^{-2}$ and $1\times10^{-4}$ mole/liter and phosphine ligand concentration between 5 and 50 wt. percent, in a temperature range between 80° and 175° C., preferably 110° and 145° C. The above concentrations and temperatures are selected to provide appropriately high $H_2/CO$ and Rh/L ratios to constitute an effective catalyst system in the present continuous operation. Such a system produces 0.5 to 2 g mole/liter/hour aldehyde and loses less than 1%, preferably less than 0.3%, of its activity per day while a n/i-aldehyde product ratio in excess of 9, preferably in excess of 15, is maintained.

The process of the present invention employing alkyl diaryl phosphine rhodium complexes can also be advantageously combined with other processes because of the thermal stability and selectivity of the catalysis obtained by such processes. The hydroformylation could be advantageously carried out either when coupled with aldol condensation alone or when coupled with aldol condensation and hydrogenation. Such combined processes are highly selective to the corresponding aldehydes. For example, in the case of the terminal olefins, such as alpha-olefin reactants, the following main aldehyde forming reactions take place when the present alkyl diaryl phosphine rhodium complex hydroformylation and hydrogenation catalyst is combined with a base catalyst for aldolization such as KOH:

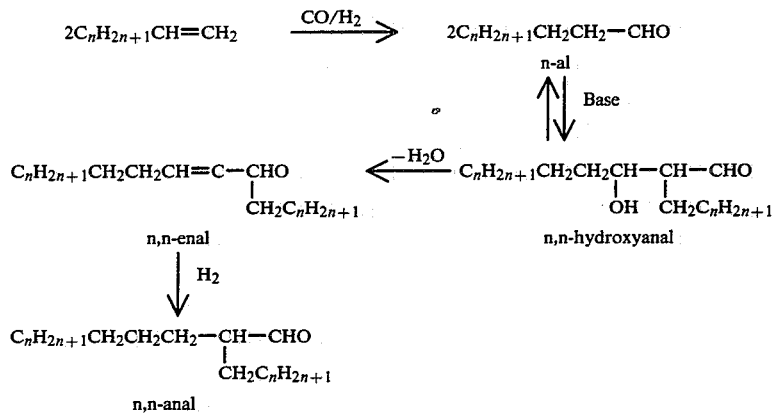

wherein the simple n-aldehyde product of hydroformylation is n-al, the thermally unstable primary product of aldolization is n,n-hydroxyanol, the unsaturated aldehyde resulting from dehydration is n,n-enal, and the selectively hydrogenated final saturated aldehyde is n,n-anal, wherein the n,n-prefixes indicate that both segments of the aldol compounds are derived from the terminal, i.e., normal, product of the hydroformylation. For known, applicable aldolization catalysts, reference is made to Volume 16, Chapter 1 of the monograph Organic Reactions, edited by A. C. Cope et al., published by J. Wiley and Sons, Inc., New York, N.Y. 1968.

It has been found in accordance with the invention that a combined hydroformylation/aldolization using alkyl diaryl phosphine ligands, in a large excess over the rhodium complex catalyst and a high ratio of the H$_2$/CO reactant gas resulted in a catalyst system of higher thermal stability and provided a high normal to iso isomer ratio in the production of dimer aldehyde product from alpha-olefins. It has been found that the presence of a diaryl alkyl phosphine rhodium catalyst results in greater effectiveness for the aldolization step than with base alone being present. This is especially important for water insoluble C$_6$ and higher aldehyde aldolization with small amounts of base, preferably alkali hydroxide.

A combined process also converts some of the i-aldehyde products in a so-called cross-aldolization reaction with the n-aldehyde:

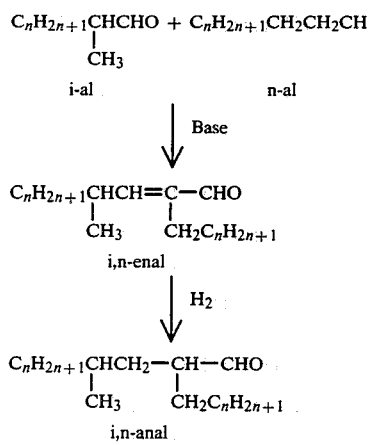

The rate of the above cross-aldolization process is slower than that of the simple aldolization. However, the relative rate of cross-aldolization increases with increasing temperature and decreasing n/i aldehyde ratios. The latter can be achieved by the addition of extra i-aldehyde to the reaction mixture.

Since high aldolization rates can be readily achieved in a combined process, the reaction parameters can be readily adjusted to provide either the unsaturated or saturated aldehydes as the major products. Short reaction times, and low olefin conversion, preferably below 50%, plus high base concentration, favor the unsaturated aldehyde. However, mostly the saturated aldol condensation product is desired. This is, of course, the favored high conversion product. It is important to note that no alcohol by-products are formed even at high olefin conversions of 80% and higher.

The preferred concentration of the strong inorganic base, i.e., alkali hydroxide, aldolization catalyst is surprisingly low, between about 0.01 and 1%, preferably between 0.5 and 0.5%.

Solvent selection is important in a preferred homogeneous, liquid phase, combined process. The preferred solvent will dissolve all the widely different components of the reaction system. Solvency for the nonpolar olefin reactant and polar caustic catalyst and water by-product require a compromise. Alcohols, particularly hydrocarbyloxyethyl alcohols are preferred. The latter are preferably of the formula J(OCH$_2$CH$_2$)$_j$OH wherein J=C$_1$ to C$_4$ alkyl, preferably primary alkyl, most preferably methyl; C$_6$ to C$_{10}$ substituted or unsubstituted phenyl, preferably phenyl; and j is an integer of from 1 to 8, preferably from 3 to 8. Such preferred solvents include methoxytriglycol, CH$_3$(OCH$_2$CH$_2$)$_3$OH, and phenoxyethanol, PhOCH$_2$CH$_2$OH. In general, the weight proportion of the relatively nonpolar hydrocarbyl segment J to that of the highly polar oligo(-oxyethyl) alcohol segment determines the relative solvent power for the nonpolar versus polar components of the reaction mixture. As such, this type of a solvent can be readily optimized for any special application of the present process. The relatively high overall polarity of this solvent assures both homogeneous reaction and a high n/i ratio of the primary products of the combined process.

With exception of the use of the base and the use of a polar, non-hydrocarbon solvent, the conditions of the present combined process are generally the same as those of a simple hydroformylation.

The following examples are presented for the purpose of illustrating, but not limiting, the present invention.

EXAMPLES

Preparation of Alkyl Diaryl Phosphine Ligands

With the exception of the available, simple alkyl diphenyl phosphine and alkylene bis-diphenyl phosphine laboratory chemicals, the ligand components of the present rhodium complexes were prepared during the present work.

The generally employed method for ligand preparation was the free radical chain addition of diphenyl phosphine to a vinylic compound in an anti-Markovnikov manner.

Ph$_2$PH + CH$_2$=CHR → Ph$_2$PCH$_2$CH$_2$R

As a rule, such additions were initiated by broad spectrum ultraviolet light at 15° C. The rate of addition depended strongly on the type of the olefinic compound employed. In general, compounds having vinylic substitution were highly reactive, while allylic derivatives were sluggish to react. The reaction times were accordingly varied. The selectivity of the additions could be improved by using more than the equivalent amount, generally 10% excess, of the phosphine adding agent. In the case of vinylic derivatives, this reduced the oligomerization of the unsaturated component. With allylic reactants, the phosphine excess suppressed the allylic reversal reactions of the radical intermediate.

If either the olefinic reactant or adduct product was immiscible with or insoluble in the diphenyl phosphine adding agent at 15° C., either the temperature was raised or a solvent was added or both were done to produce and maintain a homogeneous liquid reaction mixture. During the reaction, the conversion of reactants to products (and by-products) was followed by gas liquid chromatography (glc) and/or proton magnetic resonance spectroscopy (pmr). Usually the glc peak intensities were used to make quantitative estimates of the compositions. For identification of the product structures nmr was mainly used.

When the desired conversion was reached, the reaction mixture was usually fractionally distilled in high vacuo to obtain the pure adduct product. Most of the pure adducts were clear, colorless, mobile liquids at room temperature. In case of high melting products, recrystallization of the crude product was used as an alternate means of purification.

The expected structures of the isolated products were confirmed by pmr. Elemental analyses were also performed to check the product compositions.

The pure phosphines were studied to determine their basicity, directly by potentiometric titration and indirectly by $^{31}P$ nmr. The results of direct basicity determination will be given below, together with the other analytical characteristics of the free phosphine ligands. The $^{31}P$ nmr chemical shift values for the free ligands will be listed as comparative values when discussing the $^{31}P$ nmr of their rhodium complexes.

The phosphine basicity determinations via potentiometric titrations were performed according to the method of C. A. Streuli. For reference see Analytical Chemistry, Vol. 31, pages 1652 to 1654 in 1959 and Vol. 32, pages 985 to 987 in 1960. Half neutralization potentials (HNP's) of the phosphines were determined using perchloric acid as a titrant and pure nitromethane, free from weakly basic impurities, as a solvent. The values obtained were subtracted from the HNP of a stronger organic base, diphenyl guanidine, which served as a daily standard reference. The resulting ΔHNP values of the phosphines are indirectly related to their basicity. In case of phosphines which were also studied by Streuli, somewhat different HNP values were obtained in the present work. Since ion exchange resin purified nitromethane was used in the present work, the reported values should be more correct than Streulis'.

In the following, the preparation of different types of alkyl diaryl phosphine ligands will be described in the order of their subsequent use for forming rhodium complex catalysts. At first the trihydrocarbylsilyl substituted alkyl diphenyl phosphines will be discussed. They will be followed by simple alkyl diphenyl phosphines and alkylene bis-phosphines. Finally, the preparation of alkyl diphenyl phosphines having different types of substitution will be described. The successful use of a variety of ligands then exemplifies the broad scope of the invention.

Trihydrocarbylsilylethyl Diphenyl Phosphines (Examples 1-6)

Six trihydrocarbylsilylethyl diphenyl silanes were prepared by adding diphenyl phosphine to the corresponding vinylic or allylic silane. The preparation, physical properties and analytical composition of the compound is summarized in Examples 1-6 below. The table also shows the basicity characteristics of the products as characterized by their ΔHNP values. It is noted that all the trihydrocarbylsilyalkyl diphenyl phosphines are much stronger bases than triphenyl phosphine ($Ph_3P$:ΔHNP=510).

Accounts of the individual experiments are given in the following.

Example 1

Example 1

Preparation of Trimethylsilylethyl Diphenyl Phosphine

A magnetically stirred mixture of 46.5 g (0.25 mole) diphenyl phosphine and 25 g (0.25 mole) of vinyl trimethyl silane in a closed cylindrical quartz tube was irradiated from about 3 cm distance with two 75 Watt Hanau tube immersion lamps, with a wide spectrum of ultraviolet irradiation, in a 15° C. water bath for 26 hours. A proton magnetic resonance spectrum of a sample of the resulting mixture exhibited no significant peaks in the vinyl region indicating a substantially complete addition.

The reaction mixture was distilled in vacuo to obtain 61 g (81%) of the desired trimethylsilylethyl diphenyl phosphine adduct, as a clear colorless liquid, having a boiling range of 109°-110° C. at 0.1 mm.

Anal. Calcd. for $C_{17}H_{23}PS$: C, 71.29; H, 8.09; P, 108.81. Found: C, 71.98; H, 8.12; P, 10.59. The ΔHNP (relative half neutralization potential compared to that of diphenyl guanidine) was 385.

The selectivity to provide the desired adduct was increased when the diphenyl phosphine reactant was employed in a 10 mole % excess.

Example 2

Preparation of Tripropylsilylethyl Diphenyl Phosphine

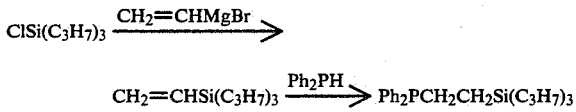

To prepare the vinyl tripropyl silane reactant, chloro-tri-n-propyl silane was reacted with vinyl magnesium bromide in refluxing tetrahydrofuran. After removing the THF solvent by distillation, the residual product was taken up in ether, was washed with ice water and then with 5% aqueous sodium hydrogen carbonate. The ether solution was then dried over anhydrous sodium sulfate and distilled to obtain vinyl tripropyl silane, bp. 75°-77° C. at 11 mm.

The vinyl tripropyl silane was then reacted with diphenyl phosphine with u.v. initiation for 86 hours in a manner described in Example 1. The conversion was about 95%. The mixture was fractionally distilled to yield approximately 63% of the theoretical yield of the product as a clear, colorless, mobile liquid. The product distilled at 155°-156° C. at 0.10 mm.

Anal. Calcd. for $C_{23}H_{35}PSi$: C, 74,54; H, 9.52; P, 8.36 Found: C, 74.35; H, 923; P, 8.37. The ΔHNP of this compound was 385.

Example 3

Preparation of Triphenylsilylethyl Diphenyl Phosphine

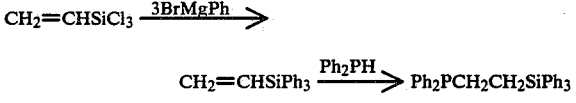

To obtain the vinyl triphenyl silane intermediate, vinyl trichloro silane was reacted with phenyl magnesium bromide in an ether-THF solvent mixture. The resulting product was worked up in a manner described in the previous example. The product was a low melting solid which could be distilled in vacuo using a hot condenser. At room temperature, the distillate solidified to yield a white crystalline compound, mp 60°-65° C. Pmr confirmed the expected vinyl triphenyl silane structure.

Anal. Calcd. for $C_{20}H_{18}Si$: C 83.86; H, 6.33. Found: C, 83.92; H, 6.34. The ΔHNP of this compound was 385.

The vinyl triphenyl silane was reacted with 10% excess of diphenyl phosphine. To maintain a homogeneous reaction mixture, a temperature of 80° C. and cyclohexane solvent ere employed. After the usual u.v. initiated addition, the reaction mixture was allowed to cool to room temperature. This resulted in the crystallization of the triphenylsilyethyl diphenyl phosphine adduct. To obtain it in a pure form, the adduct was filtered and recrystallized from a four to one mixture of cyclohexane and toluene. A white crystalline product having a melting point of 128°–131° C. was obtained.

Anal. Calcd. for $C_{32}H_{24}Si$: C, 81.32; H, 6.19; P, 6.55. Found: C, 80.97; H, 6.18; P, 6.71. The ΔHNP of this compound was 413.

Example 4

Preparation of Bis-(Diphenylphosphinoethyl)Dimethyl Silane

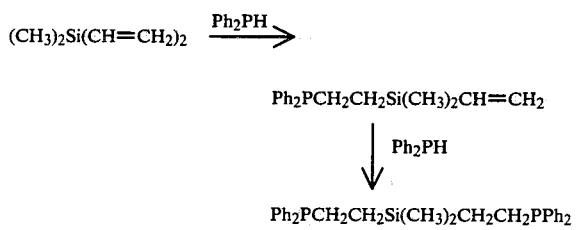

A mixture of 9.0 g (0.8 mole) dimethyl divinyl silane and 32.7 g (0.176) diphenyl phosphine (10% excess over equivalent amounts) was reacted for 22 hours in the manner described in Example 1. The reaction mixture was fractionated in vacuo to obtain minor amounts of the clear, colorless, slightly viscous liquid monoadduct, and major amounts of the clear, colorless, highly viscous liquid diadduct, i.e. the desired bis-(diphenylphosphinoethyl)dimethyl silane. The distillation yield of desired product was 84%. The bis-diphenylphosphinoethyl)dimethyl silane product had a boiling point of 238°–239° at 0.20 mm.

Anal. Calcd. for $C_{30}H_{34}P_2Si$: C, 74.35; H, 7.07; P, 12.78. Found: C 73.65; H, 6.90; P, 12.59. The ΔHNP of this compound was 434.

Example 5

Preparation of Trimethylsilylpropyl Diphenyl Phosphine

Ph$_2$PH+CH$_2$=CHCH$_2$Si(CH$_3$)$_3$→Ph$_2$PCH$_2$Ch$_2$C-H$_2$Si(CH$_3$)$_3$

A mixture of 22.8 g (0.2 mole) allyl trimethyl silane and 37.2 g (0.2 mole) diphenyl phosphine was reacted for 158 hours in the manner described in Example 1. A subsequent fractional distillation, yielded the desired pure adduct as a clear, colorless liquid. The distillation yield was 50%. The product had a boiling point of 150° C. at 0.10 mm.

Anal. Calcd. for $C_{18}H_{25}PSi$: C, 71.96; H, 8.38; P, 10.31. Found: C, 72.27; H, 8.29; P, 10.25. The ΔHNP for this product was 408.

Example 6

Preparation of Trimethylsilylmethyl Diphenyl Phosphine

Ph$_2$PLi+ClCH$_2$Si(CH$_3$)$_3$→Ph$_2$PCH$_2$Si(CH$_3$)$_3$

The known but unavailable trimethylsilylmethyl diphenyl phosphine was derived via reacting chloromethyl trimethyl silane with lithium diphenyl phosphide in an ether-hexane mixture. After removing the lithium chloride by-product by filtration, the product was isolated as a clear, colorless liquid by fractional distillation in vacuo. The distillation yield ws 86% and the product had a boiling point of 129°–130° C. at 0.2 mm.

Anal. Calcd. for $C_{16}H_{21}PSi$: C, 70.55; H, 7.77; P, 11.37. Found: C, 70.01; H, 7.64; P, 11.36. the ΔHNP for the product was found to be 404.

Alkyl Diaryl Phosphines (Examples 7–15)

For a study of the influence of the alkyl structure in alkyl diphenyl phosphine ligands, a number of commercially available compounds were obtained (Table 1, Example Nos. 7 to 11). The known but unavailable neopentyl diphenyl phosphine and 3,3-dimethylbutyl diphenyl phosphine (Table 1, Example Nos. 12 and 13, respectively) were synthesized by reacting the corresponding alkyl chlorides with lithium diphenyl phosphide.

Table 2 lists the relative half neutralization potentials of the various alkyl diphenyl phosphines. It is noted that as a group they are much more basic than triphenyl phosphine. The branching of the alkyl group, particularly in the proximity of the phosphorus, further increases the basicity.

TABLE 1

Alkyl Diphenyl Phosphine Ligands and Their Basicity

| Example No. | Structure | Indirect Basicity Δ HNP |
|---|---|---|
| 7$^a$ | Ph$_2$PCH$_2$CH$_3$ | 363 |
| 8$^b$ | Ph$_2$PCH$_2$CH$_2$CH$_3$ | 424 |
| 9$^a$ | Ph$_2$PCH$_2$CH$_2$CH$_2$CH$_3$ | 404 |
| 10$^b$ | Ph$_2$PCH$_2$CH$_2$CH$_2$CH$_2$CH$_2$CH$_3$ | 392 |
| 11$^b$ | Ph$_2$PCHCH$_2$CH$_3$<br>            \|<br>           CH$_3$ | 355 |
| 12$^a$ | Ph$_2$PC(CH$_3$)$_3$ | 341 |
| 13$^c$ | Ph$_2$PCH$_2$C(CH$_3$)$_3$ | 378 |
| 14$^c$ | Ph$_2$PCH$_2$CH$_2$C(CH$_3$)$_3$ | 412 |
| 15$^a$ | Ph$_2$P—⟨ h ⟩ | 372 |
| Standard | Ph$_3$P | 510 |

$^a$Purchased from Strem Chemicals Inc., Newburyport, Mass.
$^b$Purchased from Organometallics Inc., East Hampstead, N.H.
$^c$Prepared by reacting lithium diphenyl phosphide with the corresponding alkyl chloride.

Example 13

Preparation of Neopentyl Dimethyl Phosphine

Ph$_2$PLi+ClCH$_2$C(CH$_3$)$_3$→Ph$_2$PCH$_2$C(CH$_3$)$_3$

The known but unavailable 2,2-dimethylpropyl diphenyl phosphine was derived via reacting 2,2-dimethylpropyl chloride with lithium diphenyl phosphide in a refluxing tetrahydrofuran-hexane solvent mixture. After filtering off the lithium chloride by-product, the 2,2-dimethylpropyl, (i.e., neopentyl)diphenyl phosphine was obtained by the fractional distillation of the filtrate between 109° and 110° C. at 0.1 mm.

Example 14

Preparation of 3,3-Dimethylbutyl Diphenyl Phosphine $$Ph_2PH + CH_2=CHC(CH_3)_3 \rightarrow Ph_2PCH_2CH_2C(CH_3)_3$$

Diphenyl phosphine and t-butylethylene, i.e. 3,3-dimethyl butene, were reacted in the manner of Example 1. However, some phase separation occurred, and consequently, the reaction was slow. The expected adduct was separated from the reactants by fractional distillation. It was obtained as a colorless, clear liquid, boiling between 125°–127° C. at 0.2 mm.

As a known compound, t-butylethyl, (i.e., 3,3-dimethylbutyl)diphenyl phosphine was also synthesized via the known displacement approach: the reaction of lithium diphenyl phosphide with 3,3-dimethylbutyl chloride provided the compound in good yield.

Alkylene Bis-(Diphenyl Phosphines)

(Examples 16–22)

As a class of compounds alkylene bis-diphenyl phosphines are known. In the present work, available compounds were used. The bis-phosphines as such were studied only to determine their basicity. The results are shown in Table 2. According to the results at the transition from chelating to non-chelating phosphines (n=3 to n=4) different phosphine species are present as indicated by the pairs of ΔHNP values.

TABLE 2

Alkylene Bis-(Diphenyl Phosphine) Ligands and Their Basicity $Ph_2P(CH_2)_mPPh_2$

| Example | Polymethylene Bridge, m | Indirect Basicity ΔHNP |
|---|---|---|
| 16 | 1 | 453 |
| 17 | 2 | 431 |
| 18 | 3 | 395, 548 |
| 19 | 4 | 315, 378 |
| 20 | 5 | — |
| 21 | 6 | 423 |
| 22 | 14 | — |

Variously Substituted Alkyl Diphenyl Phosphines (Examples 23–47)

All the ligands which will be subsequently described were prepared by the addition of diphenyl phosphine to differently substituted vinylic compounds. Most of the adducts are novel, and none of them were previously prepared by the present method.

Example 23

Preparation of Phenylethyl Diphenyl Phosphine $$Ph_2PH + CH_2=CHPh \rightarrow Ph_2PCH_2CH_2Ph$$

2-Phenylethyl diphenyl phosphine, a known but unavailable compound, was prepared in the present work via a new method, i.e., the addition of diphenyl phosphine to styrene. A mixture of the unsaturated compound (20.8 g, 0.20 mole) and the phosphine (39.1 g, 0.21 mole, 5% excess) was irradiated for 5 hours in the usual manner. The desired adduct, 2-phenylethyl diphenyl phosphine, was obtained as a pure colorless, clear liquid distillate by distillation in vacuo. The distillation yield was 87% and the product had a boiling point of 171°–173° C. at 1 mm. (Table 3).

Example 24

Preparation of Pyrrolidinonylethyl Diphenyl Phosphine

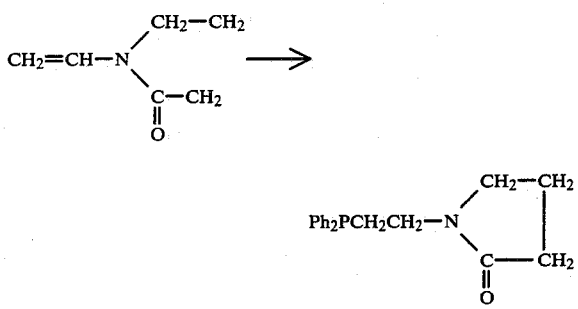

A mixture of 37.2 (0.2 mole) diphenyl phosphine and 22.2 g (0.2 mole) N-vinyl-2-pyrrolidinone was reacted with U.V. initiation for 48 hours. GLC analyses of the reation mixture indicated that after 5, 24 and 48 hours the conversions to the desired adduct were 63, 93 and 99% respectively. The crude product was purified by distillation to obtain pure N-2-pyrrolidinonylethyl diphenyl phosphine as a hazy, colorless, viscous liquid (Table 3).

TABLE 3

Preparation, Physical Properties and Composition of Various Substituted Alkyl Diphenyl Phosphine Ligands

| Example No. | Example No. E- | Structure of Ligand | Unsaturated Reactant Used | Ligand Bp. °C./mm (Mp. °C.) | Distd Yield ~% |
|---|---|---|---|---|---|
| 23 | 4275-VI | $Ph_2PCH_2CH_2Ph$ | $CH_2=CHPh$ | 171–173/0.1 | 87 |
| 24 | 5382-IX | $Ph_2PCH_2CH_2N\begin{smallmatrix}CH_2-CH_2\\ \mid \\ CO-CH_2\end{smallmatrix}$ | $CH_2=CH-N\begin{smallmatrix}CH_2-CH_2\\ \mid \\ CO-CH_2\end{smallmatrix}$ | 181–178/0.1 | 83 |
| 25 | 5433-IX | $Ph_2PCH_2CH_2CH_2N(C_2H_5)_2$ | $CH_2=CHCHN(C_2H_5)_2$ | 137–138/0.1 | — |
| 26 | 5431-VIII | $Ph_2PCH_2CH_2SO_2C_2H_5$ | $CH_2=CHSO_2C_2H_5$ | b | 69 |
| 27 | 5421-III | $Ph_2PCH_2CH_2POPh_2$ | $CH_2=CHPOPh_2$ | (182–184[a]) | 41[a] |
| 28 | 5391-XII | $Ph_2PCH_2CH_2COCH_3$ | $CH_2=CHCOCH_3$ | 148–150/0.09–0.08 | 56 |

TABLE 3-continued
Preparation, Physical Properties and Composition of Various Substituted Alkyl Diphenyl Phosphine Ligands

| | | | | | |
|---|---|---|---|---|---|
| 29 | 5384-X | $Ph_2PCH_2CH_2CO_2CH_3$ | $CH_2$=$CHCO_2CH_3$ | 162–160/ 0.30–0.32 | 60 |

| Example No. | Example No. E- | Elemental Composition | | | | | | Inverse Basicity Δ HNP |
|---|---|---|---|---|---|---|---|---|
| | | Calcd. | | | Found | | | |
| | | C | H | P | C | H | P | |
| 23 | 4275-VI | 82.74 | 6.60 | 10.66 | 82.30 | 6.67 | 10.77 | 416 |
| 24 | 5382-IX | 72.71 | 6.89 | 10.42 | 72.31 | 6.71 | 10.50 | 450 |
| 25 | 5433-IX | 76.22 | 8.75 | 4.68 | 76.55 | 8.76 | | |
| 26 | 5431-VIII | 62.73 | 6.25 | 10.11 | 62.49 | 6.17 | | 543 |
| 27 | 5421-III | 75.36 | 5.84 | 14.99 | 74.85 | 5.84 | 14.52 | 430 |
| 28 | 5391-XII | 74.99 | 6.69 | 12.08 | 74.53 | 6.58 | 11.82 | 425 |
| 29 | 5384-X | 70.58 | 6.29 | 11.38 | 70.81 | 6.31 | 11.25 | 455 |

*a*Recrystallized from methanol
*b*Recrystallized from 1-propanol which was also used as the solvent for the reaction.

Example 25

Preparation of Diethylaminopropyl Diphenyl Phosphine

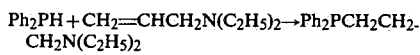

$Ph_2PH + CH_2$=$CHCH_2N(C_2H_5)_2 \rightarrow Ph_2PCH_2CH_2CH_2N(C_2H_5)_2$

A mixture of 17 g (0.15 mole) allyl diethyl amine and 30.7 g (0.165 mole, 10% excess) of diphenyl phosphine is reacted in the usual manner with u.v. irradiation for 17 hours. A subsequent analysis of the reaction mixture indicated that about one third of the reactants was converted. The only product formed was the desired adduct, 2-diethylaminopropyl diphenylphosphine. It was isolated as a clear colorless liquid (Table 3).

Example 26

Preparation of Ethylsulfonylethyl Diphenyl Phosphine

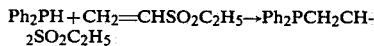

$Ph_2PH + CH_2$=$CHSO_2C_2H_5 \rightarrow Ph_2PCH_2CH_2SO_2C_2H_5$

A mixture of 64 g (0.34 mole) of diphenyl phosphine and 40.2 g (0.33 mole) of highly reactive, freshly distilled vinyl ethyl sulfone monomer was irradiated in the usual manner. To suppress polymer forming side reactions the temperature of the reaction mixture was kept below 5° C. by an ice-water bath and the u.v. irradiation was limited to 105 minutes. The adduct formed crystallized from the liquid mixture by the end of the reaction period. Consequently, the reaction mixture was filtered with suction to recover the crude, crystalline product, i.e. 2-ethylsulfonylethyl diphenyl phosphine. The crude, dried product (94 g, 94) was recrystallized from 670 ml methanol to yield 69 g (69%) of the compound (of unpleasant odor) as a white crystalline solid (Table 3).

Example 27

Preparation of Diphenylphosphinoethyl Diphenyl Phosphine Oxide

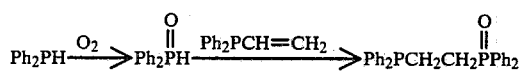

2-Diphenylphosphinoethyl diphenyl phosphine oxide, a known, but unavailable compound, was prepared via a new approach. In the first step, diphenyl phosphine was quantitatively air oxidized at 60° C. in isopropanol solution. The resulting diphenyl phosphine oxide was then added to vinyl diphenyl oxide in the manner of Example 1, with u.v. initiation.

A 26.5 wt% by wt isopropanol solution of 33.9 g (0.16 mole) of the phosphine oxide adding agent and 34.1 g (0.16 mole) of the vinyl phosphine reagent were mixed. The resulting homogeneous liquid mixture was irradiated with stirring at 30° C. for 66 hours. By the end of the reaction period, the adduct formed crystallized from the mixture. Subsequently, the crude product was dissolved in refluxing isopropanol after adding an additional 124 g of the solvent. A glc analysis of the hot solution showed that the desired addition was complete and no side reaction occurred. Consequently, the solution was allowed to cool. This resulted in the crystallization of the product. The latter was separated by filtration with suction and washing with cold isopropanol. Subsequent drying in vacuo provided 66 g (41%) of the pure compound as a white crystalline solid (Table 3).

Example 28

Preparation of Acetylethyl Diphenyl Phosphine

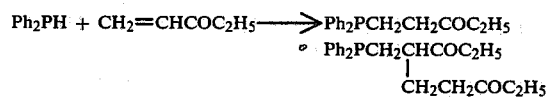

To 37.2 g (0.2 mole) stirred, nitrogen blanketed diphenyl phosphine, 15.2 g (0.22 mole) of the highly reactive vinyl ethyl ketone reactant was added dropwise. During the addition an exothermic reaction took place. As a consequence, the temperature of the reaction mixture rose to 50° C. A subsequent GLC analysis indicated that the vinyl reactant was mostly converted. Major amounts of the desired adduct and minor amounts of the diadduct were formed. The adduct, i.e. 2-acetylethyl diphenyl phosphine, was obtained by fractional distillation of the reaction mixture. At room temperature, it solidified to a light yellow substance (Table 3).

Example 29

Preparation of Carbomethoxyethyl Diphenyl Phosphine

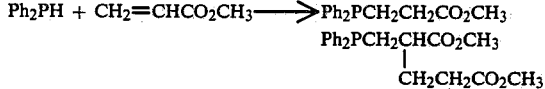

A mixture of 8.6 g (0.1 mole) methyl acrylate and 19.5 g (0.105 mole, 5% excess) of diphenyl phosphine was reacted at 15° C. in the routine manner of Example 1. U.V. irradiation resulted in a rapid reaction. After 1 hour, there was no acrylate left unconverted. The expected mono- and diadducts were formed in a weight ratio of about 95° to 5. (A sample of the reaction misture which was not irradiated also showed a complete conversion after 22 hours but not after 1 hour.) On distillation of the reaction mixture in vacuo, the monoadduct, i.e. 2-carbomethoxyethyl diphenyl phosphine, was obtained as an almost colorless, liquid distillate having a slight yellow tint (Table 3).

Example 30

Preparation of Hydroxypropyl Diphenyl Phosphine $$Ph_2PH + CH_2=CHCH_2OH \rightarrow Ph_2PCH_2CH_2CH_2OH$$

A mixture of 11.5 g (0.062 mole) diphenyl phosphine and 3.6 g (0.062 mole) of allyl alcohol was reacted with irradiation initiation at 15° C. for 110 hours in the usual manner. Subsequent glc and nmr analyses indicated complete conversion to the desired adduct, i.e. 3-hydroxypropyl diphenyl phosphine. Distillation in vacuo provided 10.5 g (72%) of the pure compound, between 162°–164° C. at 0.15 mm, as a clear colorless liquid.

Anal. Calcd. for $C_{15}H_{17}OP$: C, 73.76; H, 7.01; P, 12.68. Found: C, 73.52; H, 6.89; P, 12.82.

Example 31

Preparation of Bis-(Diphenylphosphinopropyl) Ether $$2Ph_2PH + (CH_2=CHCH_2)_2O \rightarrow (Ph_2PCH_2CH_2CH_2)_2O$$

A mixture of 7.3 g (0.75 mole) diallyl ether and 30.7 g (0.165 mole, 10% excess over the mole equivalent amount) was irradiated at 15° C. for 3 days to effect the desired addition. Glc showed that the conversion of diphenyl phosphine was about 66%. The major product, about 50% of the mixture was the desired diadduct, bis-(3-diphenylphosphinopropyl) ether. The pure diadduct was obtained by distillation in vacuo.

Example 32

Preparation of Methylthiopropyl Diphenyl Phosphine $$Ph_2PH + CH_2=CHCH_2SCH_3 \rightarrow Ph_2PCH_2CH_2CH_2SCH_3$$

A mixture of 10.6 g (0.12 mole) of allyl methyl ether and 24.6 g (0.132 mole, 10% excess) diphenyl phosphine was reacted at 15° C. with u.v. initiation for 28 hours. Glc indicated an essentially complete but nonselective conversion of the reactants. The selectivity to the desired adduct, 3-methylthiopropyl diphenyl phosphine, was about 50%. On distillation in vacuo 13 g (40%) of the compound was obtained as a clear, colorless liquid, bp. 150°–152° C. at 0.2 mm.

Anal. Calcd. for $C_{14}H_{19}PS$: C, 70.04; H, 6.98; P, 11.29; S, 11.69. Found: C, 69.78; H, 6.82; P, 11.35; S, 11.93.

Examples 33–47

Miscellaneous Substituted Alkyl Diaryl Phosphines

Using the methods described in the previous examples, diphenyl phosphine can be added to a number of vinylic and allylic compounds to yield the corresponding anti-Markovnikov adducts, i.e. substituted alkyl diphenyl phosphines, as shown by the following tabulation.

| Example No. | Unsaturated Reagent for Diphenyl Phosphine | Substituted Alkyl Diphenyl Phosphine |
|---|---|---|
| 33 | Vinyl naphthalene | Naphthyl ethyl diphenyl phosphine |
| 34 | Allyl amine | Aminopropyl diphenyl phosphine |
| 35 | Allyl morpholine | Morpholinopropyl diphenyl phosphine |
| 36 | Acrylamide | Carbamylethyl diphenyl phosphine |
| 37 | Vinyl carbazole | Carbazylethyl diphenyl phosphine |
| 38 | Vinyl pyridine | Pyridylethyl diphenyl phosphine |
| 39 | Vinyl phthalimide | Phthalimidoethyl diphenyl phosphine |
| 40 | Vinyl diethyl phosphonate | Diethyoxyphosphonylethyl diphenyl phosphine |
| 41 | Allyl ethyl ether | Ethoxypropyl diphenyl phosphine |
| 42 | Vinyl isopropyl ether | i-Propoxyethyl diphenyl phosphine |
| 43 | Vinyl furan | Furylethyl diphenyl phosphine |
| 44 | Allyl acetate | Acetoxypropyl diphenyl phosphine |
| 45 | Vinyl benzoate | Benzoyloxyethyl diphenyl phosphine |
| 46 | Allyl phenyl sulfide | Phenylthiopropyl diphenyl phosphine |
| 47 | Divinyl sulfone | Bis-(diphenylphosphinoethyl) sulfone |

Similar additions are carried out using di-4-tolyl phosphine and difluorophenyl phosphine and the above unsaturated reactants to yield the corresponding ring substituted products.

Preparation and Properties of Tris-(Alkyl Diaryl Phosphine) Rhodium Carbonyl Hydride Complexes

Preparation from Rhodium Chloride

Example 48

Preparation of Tris-(Trimethylsilylethyl Diphenyl Phosphine) Rhodium Carbonyl Hydride $$3(Ph_2PCH_2CH_2Si(CH_3)_3) + RhCl_3 \cdot 3H_2O \rightarrow [Ph_2PCH_2CH_2Si(CH_3)_3]_3Rh(CO)H$$

To a vigorously stirred, refluxing, nitrogenated solution of 11.44 g (40 mmole) of (trimethylsilylethyl) diphenyl phosphine of Example 1 in 400 ml of ethanol, a hot solution of 1.04 g (0.4 mmole) of rhodium trichloride trihydrate in 80 ml ethanol was added at once. After a delay of 15 seconds, 40 ml warm aqueous (37%) formaldehyde solution and, immediately thereafter, 80 ml hot ethanolic solution of 3.2 g of potassium hydroxide were added. The resulting clear orange liquid reaction mixture was refluxed for 10 minutes. During the heating, the color changed to deep orange.

The mixture was cooled to −25° C. to crystallize the complex product. Crystallization started at −10° C. and was completed on standing for about 2 hours at −25° C. The crystalline complex was separated by filtration through a precooled Buechner funnel with suction and washing successively with 20 ml cold portions of ethanol, water, ethanol and n-hexane. The complex was then dried in the presence of anhydrous calcium chloride at 9.1 mm over the weekend. As a result, 2.2 g (2.2 mmole, 55%) of dry tris-(trimethylsilylethyl diphenyl phosphine) rhodium carbonyl hydride complex was obtained as a fine crystalline orange-yellow powder. In a sealed capillary tube, the complex melted between 126°–129° C. to a clear dark red liquid. In an open capillary, complete melting occurred at 121° C. There was no sign of decomposition on heating up to 140° in either case.

The infrared spectrum of the complex in Nujol showed a strong carbonyl band of 1985 cm$^{-1}$ and a band of medium intensity at 1900 cm$^{-1}$.

Analyses Calcd. for $C_{52}H_{70}OP_3RhS$: C, 63.01; H, 7.12; P, 9.38; Found: C, 62.89; H, 7.06; P, 9.59.

Preparation from Tris-(Triphenyl Phosphine) Rhodium Carbonyl Hydride Via Ligand Displacement

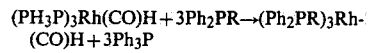

The tris-(alkyl diaryl phosphine) rhodium carbonyl hydride complexes were prepared be reacting the readily available tris-(triphenyl phosphine) rhodium carbonyl hydride (from Engelhard Minerals and Chemicals Corporation, Newark, N.J.) with the corresponding alkyl diaryl phosphines. Generally, the reactions were performed in a mixture of toluene and deuterated benzene as a solvent under a nitrogen blanket. The deuterated benzene component was used as a primary nmr standard.

At first, a solution of about 5% of the alkyl diaryl phosphine reactant was prepared. To samples of the solution, TPP rhodium carbonyl hydride was added in equivalent and half equivalent amounts. The resulting mixtures were magnetically stirred until homogeneous liquids were obtained. Additional amounts of the toluene solvent were used if needed. The homogeneous reaction mixture was then studied by $^{31}P$ nmr spectroscopy. Chemical shifts were measured by assigning a shift of 0 PPM to the frequency at which 1M $H_3PO_4$ would resonate.

The $^{31}P$ nmr experiments were carried out using a JEOL FX 900 multi-nuclear nmr spectrometer. When required the experimental conditions were adjusted, i.e. the $^1H$-$^{31}P$ decoupling was removed and longer delays between pulses were employed, to determine the relative populations of free and rhodium bound alkyl diphenyl phosphine and TPP.

Figure 2:
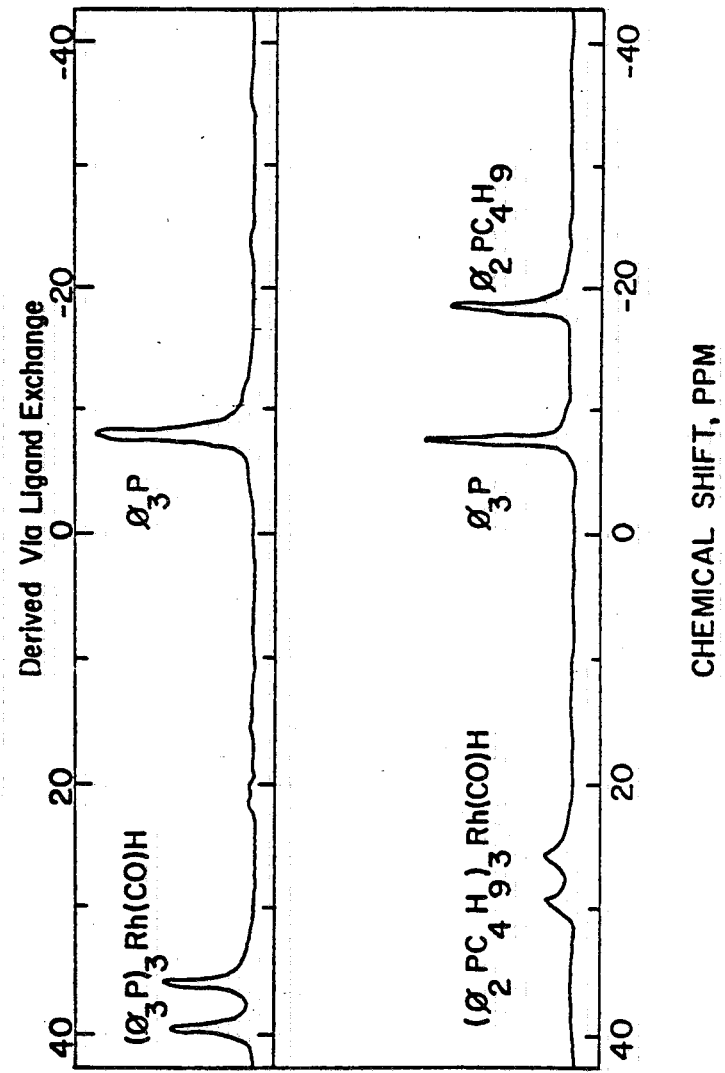
FIG. 2 illustrates a comparative $^{31}P$ NMR spectra of certain rhodium complexes.

The $^{31}P$ nmr experiments are illustrated in FIG. 2 which shows the spectrum of a six to one mixture of n-butyl diphenyl phosphine and tris-TPP rhodium carbonyl hydride, in comparison with a spectrum of a three to one mixture of TPP and tris-TPP rhodium carbonyl hydride.

In the presence of excess butyl diphenylphosphine, the only significant doublet peak of complexed phosphorus is that derived from butyl diphenyl phosphine. This complex was derived by ligand exchange as indicated by the singlet of displaced free TPP. Although the doublet of the butyl diphenyl phosphine complex has a chemical shift value different from that of TPP, the coupling constants are about the same for both complexes. The coupling constant and chemical shift difference between bound and free ligand indicate that both ligands form tris-(phosphine) rhodium carbonyl hydrides.

Similar ligand exchange experiments were carried out with other alkyl diphenyl phosphines to form their tris-(phosphine) rhodium carbonyl hydride complexes to determine the characteristic nmr parameters of such complexes.

The nmr parameters of the trihydrocarbylsilylalkyl diphenyl phosphine complexes are shown by Table 4. The most characteristic parameter is the chemical shift value of the rhodium complexed ligand. For comparison, the chemical shift values of the free ligands are also tabulated. Complexation of rhodium of the phosphine apparently produced a similar downfield charge of the shift values. Finaly, it is also noted in reference to the table, that even the limited exposure of the rhodium complexed phosphines to air resulted in some oxidation to the corresponding phosphine oxides. The latter exhibited sharp singlets slightly upfield from the complexed phosphine.

The data of Table 4 shows that with the exception of the last compound all the phosphines ligands form similar well characterizable complexes at room temperature. The line shapes of the signals showed little but varying broadening, i.e., ligand exchange. In the case of the tris-(trimethylsilylethyl diphenyl phosphine), tris-SEP, rhodium carbonyl hydride complex (Example 48), there was moderately slow ligand exchange between free and complexed phosphines. The exchange mechanism is illustrated for the SEP complex by the following (for details of the hydroformylation mechanism refer to FIG. 1):

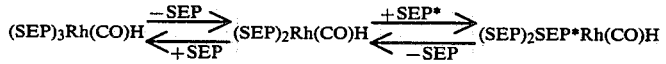

The line shapes of signals for the SEP complex and the known TPP complex are compared by FIG. 3 at various temperatures. At first, the 30° C. spectra will be discussed. These spectra indicate that at 30° C., there is a similar, ligand exchange rate between the new SEP and the known TPP complex.

TABLE 4

| | | | Chemical Shift σ, ppm | | Coupling Constant $^J$P-Rh | Chemical Shift σ, ppm | Chemical Shift Difference Δσ, ppm |
|---|---|---|---|---|---|---|---|
| Example No. of Complex | Example No. of Ligand | Chemical Structure of Complex | Free Ligand | Complexed Ligand | Complexed Ligand | Phosphine Oxide | Complex Ligand |
| — | — | $(Ph_3P)_3[Rh(CO)H]$ Reference) | −7.5 | +38.3 | 155 | | 45.8 |
| 48 | 1 | $[Ph_2PCH_2CH_2Si(CH_3)_3]_3[Rh(CO)H]$ | −12.1 | +34.6 | 150 | +27.0 | 46.9 |
| 49 | 2 | $[Ph_2PCH_2CH_2Si(C_3H_7)_3]_3[Rh(COH]$ | −11.2 | +34.8 | 151 | +29.9 | 45.0 |

TABLE 4-continued
³¹P NUCLEAR MAGNETIC RESONANCE PARAMETER OF FREE AND RHODIUM-COMPLEXED TRIHYDROCARBYLSILYLALKYL DIPHENYL PHOSPHINES

| Example No. of Complex | Example No. of Ligand | Chemical Structure of Complex | Chemical Shift σ, ppm Free Ligand | Chemical Shift σ, ppm Complexed Ligand | Coupling Constant $J_{P-Rh}$ Complexed Ligand | Chemical Shift σ, ppm Phosphine Oxide | Chemical Shift Difference Δσ, ppm Complex Ligand |
|---|---|---|---|---|---|---|---|
| 50 | 3 | $(Ph_2PCH_2CH_2SiPh_3)_3[Rh(CO)H]$ | −10.6 | +35.5 | 151 | +21.1 | 46.1 |
| 51 | 4 | $[(Ph_2PCH_2CH_2)_2Si(CH_3)_2]_3[Rh(CO)H]$ | −12.2 | | | | |
| 52 | 5 | $[Ph_2PCH_2CH_2CH_2Si(CH_2)_3]_3[Rh(CO)H]$ | −19.7 | +26.6 | 154 | +24.6 | 46.3 |
| 53 | 6 | $[Ph_2PCH_2Si(CH_3)_3]_3[Rh(CO)H]$ | −24.4 | +17.0 | 133$^a$ | +23.9 | 41.4 |

$^a$The $^{31}P - ^{103}Rh$ coupling was not resolved at room temperature but was clearly resolved at 60° C.

The tris-SEP complex and two other trimethylsilylalkyl diphenyl phosphine complexes (Examples 51 and 52) showed a very similar ligand exchange behavior at 30° C. The tripropylsilylethyl diphenyl phosphine complex (Example 49) exhibited a definitely slower exchange rate. The exchange rate of the triphenylsilylethyl diphenyl phosphine complex (Example 50) was even much slower than that. It appeared that substituted alkyl diphenyl phosphine ligands of increasing bulkiness had decreasing ligand exchange rates. In both cases though, the TPP ligand exchanged less rapidly than the alkyl diphenyl phosphine.

Finally, it is noted that when even a moderately bulky alkyl substituent was close to the phosphorus, i.e., in the case of trimethylsilymethyl diphenyl phosphine, the complexation of phosphorus to the rhodium was inhibited (Example 54). In that case, there was no distinct complex formation with the sterically hindered ligand at 30° C. At −60° C., a stable complex was formed. However, this complex was decomposed when its solution was heated under hydroformylation process conditions.

As far as ligand exchange rates at higher temperatures are concerned, the results shown by FIG. 3 are typical. FIG. 3 shows the comparison of two systems: tris-triphenyl phosphine rhodium carbonyl hydride plus triphenyl phosphine and tris-trimethylsilylethyl diphenyl phosphine rhodium carbonyl hydride plus triphenyl phosphine. The latter system is the result of equilibrating the TPP complex with trimethylsilylethyl diphenyl phosphine (SEP):

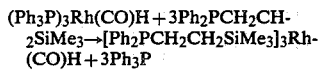

$(Ph_3P)_3Rh(CO)H + 3Ph_2PCH_2CH_2SiMe_3 \rightarrow [Ph_2PCH_2CH_2SiMe_3]_3Rh(CO)H + 3Ph_3P$ SEP being a substituted alkyl diphenyl phosphine, was found to be a stronger complexing agent that TPP. The spectra of both systems were taken under comparative conditions at 30°, 60° and 90°.

The line shapes of the signals of the 30° C. showed little signal broadening in both cases. This indicated comparably slow exchange rates of about 25 per second. In alternative terms, relatively long average exchange lifetimes, in the order of 2×10⁻² sec, were indicated for both tris-phosphine complexes. At 60°, considerable line broadening occurred, indicating a much faster exchange. The exchange acceleration was greater in the case of the TPP system (k=600 vs. 80). The average lifetime was about 3×10⁻³ sec for the TPP system and 6×10⁻³ sec for the SEP system. At 90°, only a single, borad signal could be observed for the TPP system while the SEP system still exhibited separate, although extremely broad, chemical shift ranges for the complexed and free phosphorus species.

Apparently, the exchange acceleration in the case of the TPP system was tremendous. The average lifetime between exchanges was reduced about two orders of magnitude to 5×10⁻⁵ sec (k≈10,000). In the case of the SEP system, the average lifetime dropped by about one order to 5×10⁻⁴ sec (k≈1,500). It must be emphasized that the exchange rates and lifetimes reported here may change somewhat when the lineshape is subjected to a rigorous computer analysis. The relative order of their values will remain unaltered, however.

It is interesting to note that there was no great change of equilibria with the increasing exchange rates. Apparently, both ligand elimination and addition increase similarly in this temperature range. The tris-phosphine rhodium species remained the dominant form of complexes. In the SEP complex plus free TPP system, the rhodium remained predominantly complexed to the SEP.

The role of excess phosphine ligand is apparently to maintain the equilibria in favor of the tris-phosphine complex, i.e. to reduce both the concentration and average lifetime of the unstable and highly reactive bis-phosphine complex. The increased ligand exchange rate provides enough active bis-phosphine complex catalytic species for fast hydroformylation, without leading to noncatalytic side reactions, i.e. catalyst decomposition.

In summary, the above and similar ligand exchange rate studies indicate that, in the presence of excess ligand, the alkyl diaryl phosphine rhodium complexes are catalytically activated at higher temperatures than the known triaryl phosphine rhodium complexes.

The results of a similar systematic ³¹P study of various alkyl diphenyl phosphines is summarized in Table 5. The Table shows the ³¹P nmr parameters of free and rhodium complexed alkyl diphenyl phosphines in solution at 35°. An overview of Table 5 indicates that five of the seven phosphine ligands examined formed tris-phosphine rhodium carbonyl hydride complexes. Steric crowding apparently inhibited complex formation. Comments on the detailed data of the table are made in the following.

As it was already discussed in conjunction with FIG. 2, n-butyl diphenyl phosphine exhibits a ligand exchange behavior similar to that of the SEP ligand (Example 54). However, it was slightly less effective in completely displacing TPP. In the latter respect, the bulkier n-hexyl diphenyl phosphine was a more effective ligand (Example 55).

In comparison to n-butyl diphenyl phosphine, secondary butyl diphenyl phosphine is quite ineffective in replacing the TPP ligand (Example 56). Cooling to −60° was necessary to observe a clearly resolved doublet signal for the complexed secondary butyl compound. Alternatively, a complex of this ligand could be obtained at room temperature starting with (PH$_3$As)$_3$Rh(CO)H (TPA complex) in place of the TPP complex.

plexed ligands of this type are summarized in Table 6. The first three bis-phosphines of the table are chelate forming compounds (Examples 61–63). These were studied for comparison only. The next four compounds,

TABLE 5
$^{31}$P NUCLEAR MAGNETIC RESONANCE PARAMETER OF FREE AND RHODIUM COMPLEXED ALKYL DIPHENYL PHOSPHINES

| Example No. of Complex | Example No. of Ligand | Chemical Structure of Complex | Chemical Shift σ, ppm Free Ligand | Chemical Shift σ, ppm Complexed Ligand | Coupling Constant $J_{P-Ph}$ Complexed Ligand | Chemical Shift Difference Δσ, ppm Complex Ligand |
|---|---|---|---|---|---|---|
| 54 | 9 | (φ$_2$PCH$_2$CH$_2$CH$_2$CH$_3$)$_3$Rh(CO)H | −18.6 | +27.4 | 149 | 46.0 |
| 55 | 10 | (φ$_2$PCH$_2$CH$_2$CH$_2$CH$_2$CH$_2$CH$_3$)$_3$Rh(CO)H | | | | |
| 56 | 11 | (φ$_2$PCHCH$_2$CH$_3$)$_3$Rh(CO)H<br>\|<br>CH$_3$ | −4.8 | +40.0 | 154$^a$ | 45.0 |
| 57 | 12 | (φ$_2$PC(CH$_3$)$_3$]$_3$Rh(CO)H | −25.1 | | | |
| 59 | 14 | [φ$_2$PCH$_2$CH$_2$C(CH$_3$)$_3$]$_3$Rh(CO)H | −16.8 | +27.5 | 152 | 44.3 |
| 60 | 15 | [φ$_2$P—⟨h⟩]$_3$Rh(CO)H | −5.9 | +42.0 | 152$^a$ | −48 |

$^a$The $^{31}$P—$^{103}$Rh coupling was not resolved at room temperature but was clearly resolved at 60° C.

Tertiary butyl and neopentyl diphenyl phosphine (Examples 57 and 58) did not form tris-phosphine complexes under standard experimental conditions. Surprisingly, the t-butyl compound had a destabilizing effect on the TPP complex reactant. As a result the mixture rapidly turned black, apparently due to rhodium precipitation.

3,3-Dimethylbutyl diphenyl phosphine exhibited a complex forming and equilibration tendencies similar to those of its silicon analog, SEP.

Finally, it is noted that cyclohexyl diphenyl phosphine only partially replaced TPP from its complex and exhibited a very high rate of ligand exchange (Example 60). Overall this ligand and the secondary butyl diphenyl phosphine had a comparable complexing behavior. In both cases, steric crowding was a severely limiting factor.

The third type of ligands studied by $^{31}$P nmr in a similar manner were alkylene bis-(diphenyl phosphines). The parameters obtained for the free and comi.e. polymethylene bis-phosphines did form the open chain tris-phosphine catalys complexes of the present invention (Examples 64–67). Overall, the stability of the complex solutions increased in the order of their listing as indicated by their color stability. Comments on some of the details are made in the following.

The reaction mixture of methylene bis-diphenyl phosphine and the TPP complex was highly unstable (Example 61). Some of the TPP was displaced but no single new complex predominated. The mixture rapidly turned dark.

The complex formed by the reaction of dimethylene bis-diphenyl phosphine exhibited a single doublet for the complexed phosphorus (Example 62). Based on the unusual chemical shift value of this doublet and the instability of this mixture, the complex appeared to have a chelating bis-phosphine moiety. The formation of this complex was apparently complete, the ligand exchange is slow.

TABLE 6
$^{31}$P Nuclear Magnetic Resonance Parameter of Free and Rhodium Complexed Alkylene Bis-(Diphenyl Phosphines)

| Example No. of Complex | Example No. of Ligand | Chemical Structure Complex of (RH(CO)H) | Chemical Shift O, ppm Free Ligand | Chemical Shift O, ppm Complexed Ligand | Coupling Constant P—Rh Complexed Ligand | Chemical Shift Difference ΔO, ppm Complex-Ligand |
|---|---|---|---|---|---|---|
| 61 | 16 | (Ph$_2$PCH$_2$PPh$_2$) | −24.0 | | | |
| 62 | 17 | CH$_2$—PPh$_2$    Ph$_2$P—CH$_2$<br>     \\       /<br>       Rh<br>     / \| \\<br>CH$_2$—PPh$_2$  H  Ph$_2$P—CH$_2$ | −14.0 | +54.3 | 143 | 69.1 |
| 63 | 18 | {CH$_2$⟨CH$_2$—PPh$_2$/CH$_2$—PPh$_2$⟩Rh⟨CO/Ph$_2$PCH$_2$/H⟩ CH$_2$}$_2$ | −19.7 | | | |
| 64 | 19 | (Ph$_2$P(CH$_2$)$_4$PPh$_2$)$_3$Rh(CO)H | −18.4 | +29.8 | 140 | 48.2 |
| 65 | 20 | (Ph$_2$P(CH$_2$)$_5$PPh$_2$)$_3$Rh(CO)H | −18.5 | +27.7 | 153 | 46.2 |

TABLE 6-continued

31P Nuclear Magnetic Resonance Parameter of Free and Rhodium Complexed Alkylene Bis-(Diphenyl Phosphines)

| Example No. of Complex | Example No. of Ligand | Chemical Structure Complex of (RH(CO)H) | Chemical Shift O, ppm | | Coupling Constant P—Rh | Chemical Shift Difference ΔO, ppm |
|---|---|---|---|---|---|---|
| | | | Free Ligand | Complexed Ligand | Complexed Ligand | Complex-Ligand |
| 66 | 21 | $(Ph_2P(CH_2)_6PPh_2)_3Rh(CO)H$ | −18.3 | +26.9 | 153 | 45.2 |
| 67 | 22 | $(Ph_2P(CH_2)_{14}PPh_2)_3Rh(CO)H$ | −18.6 | +27.5 | 152 | 46.1 |

The complex derived from the trimethylene bis-phosphine was of further increased stability and reduced ligand exchange (Example 63). Based on the complicated set of doublet signals, the presence of chelating bis-phosphine complexes such as the compound shown in the table is suggested.

propyl diphenyl phosphines, were similar to SEP both with regard to the completeness of the expected complex formation and ligand exchange (Examples 24, 25). It should be noted that the 2-pyrrolidinonylethyl substitution led to unusual chemical shift values for both the free and complexed phosphine ligand.

TABLE 7

31P NUCLEAR MAGNETIC RESONANCE PARAMETERS OF VARIOUSLY SUBSTITUTED ALKYL DIPHENYL PHOSPHINES AND THEIR RHODIUM COMPLEXES

| Example No. of Complex | Example No. of Ligand | Chemical Structure of Complex | Chemical Shift σ, ppm | | Coupling Constant $J_{P-Rh}$ Complexed Ligand | Chemical Shift Difference Δσ, ppm Complex − Ligand | Experimental No. E | |
|---|---|---|---|---|---|---|---|---|
| | | | Free Ligand | Complexed Ligand | | | Ligand | Complex |
| 68 | 23 | $(Ph_2PCH_2CH_2Ph)_3Rh(CO)H$ | −16.6 | +27.6 | 153 | 44.2 | 4275-VIA | 4275-VIB |
| 69 | 24 | $[Ph_2PCH_2CH_2N\langle{CH_2-CH_2 \atop C(=O)-CH_2}\rangle]_3Rh(CO)H$ | −23.0 | +21.6 | 151 | 44.6 | 5382-VIIIA | 5382-IXB |
| 70 | 25 | $[Ph_2PCH_2CH_2CH_2N(C_2H_5)_2]Rh(CO)H$ | −17.8 | +27.4 | 151 | 45.2 | 5433-VIIIA | 5433-VIIIB |
| 71 | 26 | $[Ph_2PCH_2CH_2SO_2C_2H_5)_3Rh(CO)H$ | −18.6 | +27.3 | 151 | 45.9 | 5431-VIIIA | 5431-VIII |
| 72 | 27 | $(Ph_2PCH_2CH_2POPh_2)_3Rh(CO)H$ | −13.7 | +30.5 | 190 | | 5421-IIIA | 5421-IIIC |
| 73 | 28 | $(Ph_2PCH_2CH_2COCH_3)_3Rh(CO)H$ | +17.1 | +28.1 | 149 | 45.2 | 5391-XIIA | 5391-XIIB |
| 74 | 29 | $(Ph_2PCH_2CH_2CO_2CH_3)_3Rh(CO)H$ | −17.7 | +27.9 | 151 | 45.6 | 5384-XA | 5384-XB |
| 75 | 30 | $(Ph_2PCH_2CH_2CH_2OH)_3Rh(CO)H$ | −16.9 | +27.8 | 154 | 44.7 | 4291-VA | 4291-VB |
| 76 | 31 | $[(Rh_2PCH_2CH_2CH_2)_2O]_3Rh(CO)H$ | −17.5 | +27.8 | 151 | 45.3 | 4295-XIIA | 4295-XIIB |
| 77 | 32 | $(Ph_2PCH_2CH_2CH_2SCH_3)_3Rh(CO)H$ | −17.7 | +27.1 | 151 | 44.8 | 4296-VIIIA | 4296-VIIIB |

The complexing behavior and the nmr parameters of the non-chelating polymethylene bis-diphenyl phosphines (Examples 64–67) were, in general, very similar to that of the simple n-alkyl diphenyl phosphines. More particularly, the ligand exchange rates observed were very similar to those previously found for the SEP ligand. In the presence of excess ligand, mostly one phosphine moiety of the bis-phosphine was coordinated. The phosphine group at the other end was mostly free as indicated by the formulas of the table.

The 31P nmr parameters of the rhodium complexes of ten variously substituted alkyl diphenyl phosphines (Examples 68–78) were also determined. With the exception of the diphenyl phosphine oxide substituted ligand (Example 72), all the complexes exhibited similar phosphorus to rhodium coupling constants. This indicated their tris-phosphine complex character. In general these ligands exhibited the type of behavior discussed previously in the case of trihydrocarbylsilyl substituted alkyl diphenyl phosphines. Some specific observations are made in the following.

The 2-phenylethyl diphenyl phosphine formed the usual tris-phosphine complex but was less effective than SEP in displacing TPP (Example 68). The next two ligands, i.e. the 2-pyrrolidinonyl and 3-diethylamino- The β-sulfone and β-phosphinoxide substituted ligands both completely displaced TPP like SEP did (Examples 71 and 72). However, they exhibited a significantly lower ligand exchange rate at room temperature. Partly due to the phosphine-phosphine oxide coupling, the spectrum of the phosphine oxide substituted complex appeared to be exceptional.

As far as the remaining ligands are concerned, the 2-carbomethoxyethyl derivative also exhibited a smaller ligand exchange than SEP (Example 74). The rest of the ligands were similar to SEP both with regard to equilibria and rates (Examples 73 and 75 to 77).

Other suitable substituted alkyl diaryl phosphines are reacted similarly with tris-(triphenyl phosphine) rhodium carbonyl hydride, tris-(triphenyl arsine) rhodium carbonyl hydride and the like to provide the corresponding tris-phosphine complexes. For example, starting with the substituted alkyl diphenyl phosphine ligands of Examples 33 to 47, the following miscellaneous substituted alkyl diphenyl phosphine complexes are formed:

| Example No. 5 | | |
|---|---|---|
| Complex | Ligand | Name of the Complex Formed |
| 78 | 33 | tris-(naphthyl ethyl diphenyl phosphine) rhodium carbonyl hydride |
| 79 | 34 | tris-(aminopropyl diphenyl phosphine) rhodium carbonyl hydride |
| 80 | 35 | tris-(morpholinopropyl diphenyl phosphine) rhodium carbonyl hydride |
| 81 | 36 | tris-(carbamylethyl diphenyl phosphine) rhodium carbonyl hydride |
| 82 | 37 | tris-(carbazylethyl diphenyl phosphine) rhodium carbonyl hydride |
| 83 | 38 | tris-(pyridylethyl diphenyl phosphine) rhodium carbonyl hydride |
| 84 | 39 | tris-(phthalimidoethyl diphenyl phosphine) rhodium carbonyl hydride |
| 85 | 40 | tris-(diethyoxyphosphonylethyl diphenyl phosphine) rhodium carbonyl hydride |
| 86 | 41 | tris-(ethoxypropyl diphenyl phosphine) rhodium carbonyl hydride |
| 87 | 42 | tris-(2-propoxyethyl diphenyl phosphine) rhodium carbonyl hydride |
| 88 | 43 | tris-(furylethyl diphenyl phosphine) rhodium carbonyl hydride |
| 89 | 44 | tris-(acetoxypropyl diphenyl phosphine) rhodium carbonyl hydride |
| 90 | 45 | tris-(benzoyloxyethyl diphenyl phosphine) rhodium carbonyl hydride |
| 91 | 46 | tris-(phenylthiopropyl diphenyl phosphine) rhodium carbonyl hydride |
| 92 | 47 | tris-[bis-(diphenylphosphinoethyl) sulfone] bis-(rhodium carbonyl hydride) |

Similar substituted alkyl diaryl phosphine complexes are prepared from substituted alkyl difluorophenyl phosphines, substituted alkyl ditolyl phosphines, and substituted alkyl phenyl naphthyl phosphines.

By selecting the appropriate substituent, the complex catalysts of the present invention can be fine tuned to provide optimum performance at the desired temperature. Also, substitution could be used as a means of adjusting the solubility character of the free and complexed alkyl diaryl phosphine ligands. For example, the hydrophilic-lipophilic character of the ligand could be appropriately changed by introducing either large hydrocarbon substituents (Example 3) or highly polar groups (Example 24). The acid-base character can be also changed. For example, a basic amino group could be introduced (Example 25). Such a group can be the essential factor in catalyst recovery. Other ligand substituents can increase the solubility of gaseous reactants such as CO in the liquid reaction medium. A multiplicity of non-chelating phosphine groups will drastically reduce ligand volatility.

In general, it should be pointed out that a correlation of the nmr and catalysis studies showed that those complexes which show lower ligand exchange rates at low temperatures have a higher activation energy as catalyst. That means that they required more thermal activation, i.e. higher temperatures, to become highly active catalysts. Less ligand exchange also meant a higher temperature for the irreversible thermal dissociation, i.e. decomposition of the catalyst complex.

Under the preferred process conditions for the present catalysts, the structure of the tris-(alkyl diphenyl phosphine) rhodium carbonyl hydrides as described by the nmr parameters could be formed in situ and did not undergo any irreversible change. For example, the tris-SEP complex was generated under routine hydroformylation conditions at 120° from dicarbonyl acetylacetonato rhodium and was employed for 1-butene hydroformylation. After the reaction was complete, the volatile components were removed by distillation and the residual liquid was studied by $^{31}P$ nrm. The typical parameters for tris-SEP rhodium carbonyl hyride and excess free SEP were found.

General Method of Hydroformylation

The hydroformylation of butene-1 to provide linear pentanal and branched 2-methyl butanal products was selected for comparative studies of the catalytic properties of certain of the alkyl diaryl phosphine complexes of the invention. The complexes studied were either isolated before use or generated in situ. In some cases, the desired complex was generated from the known tris-(triphenyl phosphine) rhodium carbonyl hydride by the addition of the appropriate ligand in varying amounts. According to another standard method, dicarbonyl acetylacetonato rhodium and the appropriate alkyl diaryl phosphine were used as catalyst precursors. In that case, the desired rhodium carbonyl hydride complex was generated by hydrogenation during the hydroformylation experiment. Tris-(triphenyl phosphine) rhodium carbonyl hydride in the presence of varying excesses of triphenyl phosphine was used as a known catalyst standard for comparison.

The experiments were carried out in a 300 ml stainless steel (S) and a 300 ml Hastelloy (H) autoclave, respectively. Both autoclaves were equipped with identical, highly effective, impeller type stirrers, operating at 750 rpm during the experimental runs. The other standard autoclave instrumentation was identical for both units. However, a slightly lower normal to iso aldehyde product ratio (n/i) was observed in unit H. In those casees where the type of autoclave was not specified, a stainless steel unit was used.

The standard batch hydroformylation procedure was the following: the appropriate amounts of rhodium complex were dissolved in 100 g of the proper mixture of a free phosphine and solvent. 2-propylheptyl valerate of 2-ethylhexyl acetate were used as standard solvents. They were indistinguishable. Most Often the amount of complex employed provided 100 ppm rhodium concentration. This meant 100 mg, i.e., about 0.1 mmole rhodium per 100 g. Accordingly, 100 mg per Kg, about 1 mmole per kg rhodium would be present in 1 kg starting mixture. The excess ligand added to the solvent was usually calculated to provide a ligand to rhodium ratio (L/Rh) of about 140.

The 100 g rhodium complex-ligand solution was placed into the autoclave which was then deaerated by repeated pressurization with nitrogen. The solution under atmospheric nitrogen pressure was then sealed and heated to the reaction temperature, usually 100° C.

When the solution reached 100° C., 20 g of liquid butene was pressured into the autoclave with a 1 to 4 carbon monoxide-hydrogen initial gas mixture. The butene was followed by the $CO/H_2$ mixture until a pressure of 350 psig was reached. At that point, the supply of 1:4 $CO/H_2$ was shut off and the autoclave was connected to a cylinder to about 1 liter volume containing a 1:1 $CO/H_2$ feed gas mixture at 1000 psig. The connection was made through a pressure regulating valve set to provide the 1:1 $CO/H_2$ gas to the autoclave to maintain a 350 psig pressure during the reaction. The exact $H_2/CO$ ratio of the feed gas was often varied to maintain the initial $H_2/CO$ ratio in the autoclave.

Figure 4:
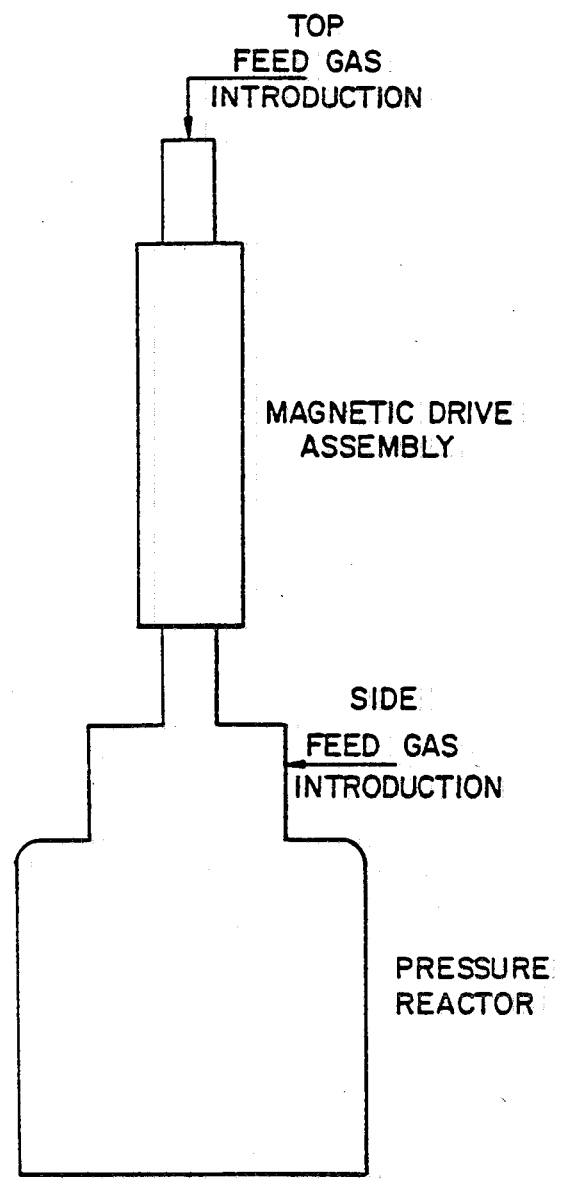
FIG. 4 is a schematic representation of an autoclave for hydroformylation.

In the standard tests, the autoclaves used were equipped with synthesis gas feed lines adjoining the autoclave above the Magnedrive stirrer assembly unit (FIG. 4). It is to be noted that this manner of introducing synthesis gas feed far from the upper level of the liquid reaction mixture resulted in an incomplete equilibration of the synthesis gas mixture between the gas and liquid phase. Particularly in those cases where the initial synthesis gas mixture (used to pressure up the reaction mixture) had an $H_2$ to CO ratio of 10 or higher, the CO component of the subsequent one to one feed gas was not effectively delivered from the top into the liquid reaction mixture due to mass transfer limitations. Therefore, the reaction mixture was often "starved" of CO during the early fast phase of the reaction. As a consequence, the $H_2/CO$ ratio in the liquid temporarily rose to very high values. This resulted in particularly high n- to i- aldehyde product ratios. Also, olefin hydrogenation and isomerization became important side reactions. This, of course, reduced the absolute accuracy of the data on catalyst selectivities. For comparison, the widely studied Tris-TPP rhodium carbonyl hydride catalyst system was used as a standard throughout the work.

Figure 12:
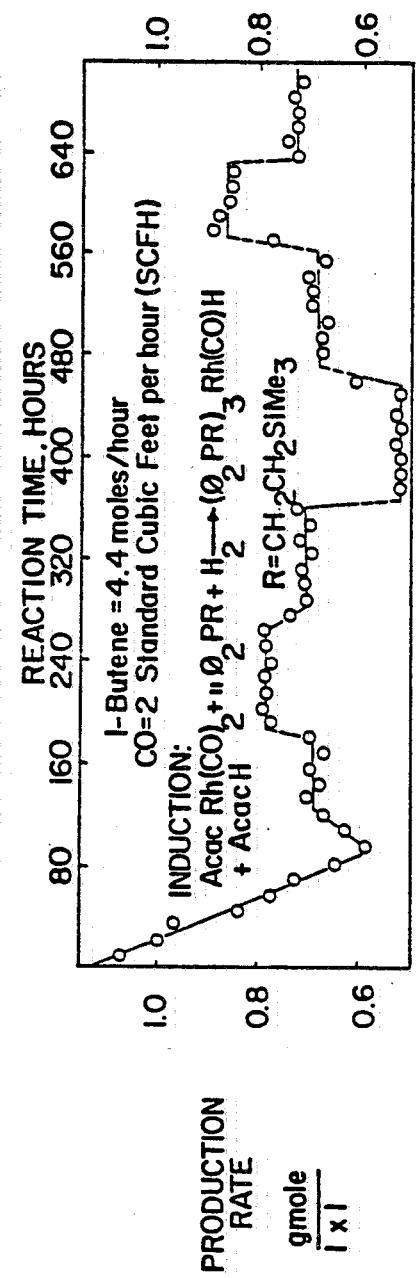
FIG. 12 is a graphical representation of aldehyde production rate during continuous butene hydroformylation.
Figure 12:
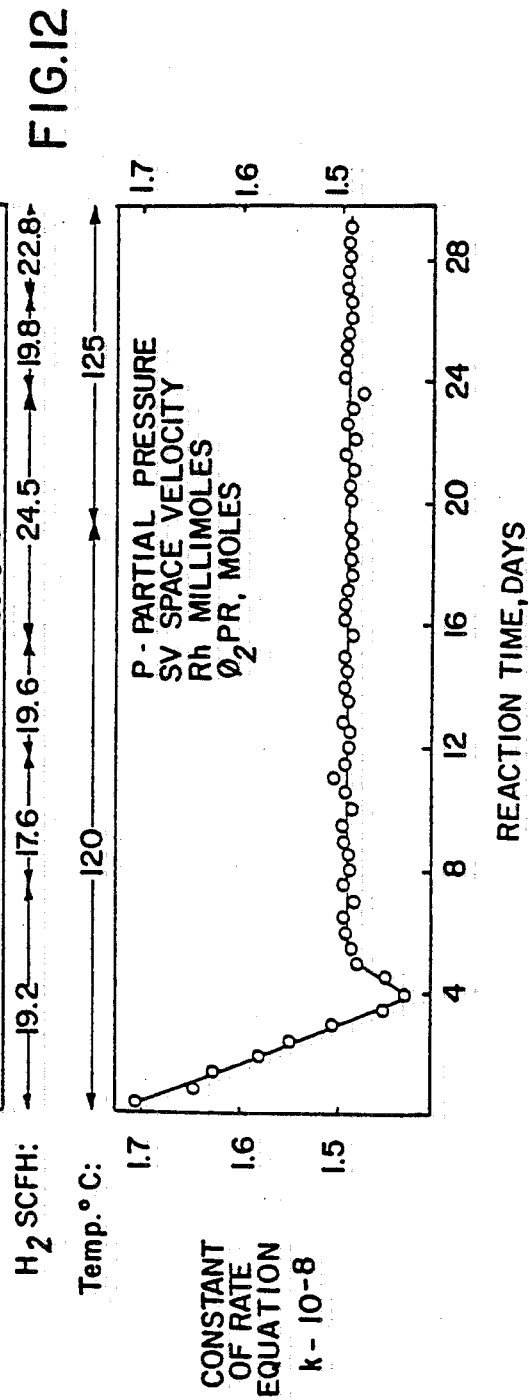

In those instances, where the effect of $H_2$ to CO ratios and the effect of CO partial pressure were specifically studied, the synthesis gas feed was introduced at the side of the autoclave, just above the liquid level. This method of operation largely avoided any temporary rise $H_2/CO$ ratios and drastically reduced hydrogenation and isomerization in cases where the initial $H_2/CO$ ratio was high. Special studies were also made in a continuous feed introduction and product flashoff operation. This allowed a continuos control of partial pressures and such provided the most accurate results (FIG. 12).

The progress of the hydroformylation was followed on the basis of the amount of 1:1 $CO/H_2$ consumed. The latter was calculated on the basis of the pressure drop in the 1 liter $CO/H_2$ cylinder. Reactant conversion calculated on the basis of CO consumption was plotted against the reaction time to determine the reaction rate. The reaction rate was expressed as the fraction of the theoretical $CO/H_2$ requirement consumed per minute (k min$^{-1}$). The reaction was discontinued when the reaction rate drastically dropped. Dependent on the side reaction, such as butene-1 hydrogenation and butene-1 to butene-2 isomerization, the stability of the catalyst complex in the mixture, such a rate drop occurred generally between 80–98% conversion. Accordingly, the reactions were usually discontinued in that conversion range. Most often the reactions were run up to 80% conversion.

When the reaction was to be discontinued, the $CO/H_2$ feed valve was shut and the autoclave was immediately cooled with cool water. In case of low conversions, ice bath was used. When cooling was complete, the synthesis gas was released slowly. The residual liquid was visually observed for catalyst decomposition. A dark orange to brown color of the originally yellow mixture indicated increasing degrees of catalyst decomposition. Severe catalyst decomposition usually resulted in the precipitation of dark solids.

Analyses of the residual liquid mixture were carried out using gas chromatography. The liquids were analyzed in a gc instrument using flame ionization detector. By this instrument, the $C_4$ hydrocarbons were detected. Due to the lower response of this detector to the aldehydes, the intensity of the hydrocarbon peaks was multiplied usually by 0.7 to obtain the necessary concentration correction. The individual, gaseous $C_4$ hydrocarbons were separated by another chromatograph. At first the gases were separated from the liquids and then the individual components of the gas were chromatographed and detected by a thermal conductivity detector.

1-Butene Hydroformylation Experiments (Examples 93–100)

In the following description of 1-butene hydroformylation catalysis by tris-(alkyl diaryl phosphine) rhodium carbonyl hydride based catalyst systems, at first their unique catalytic behavior will be exemplified by a detailed description of the tris-(trimethylsilylethyl diphenyl phosphine) rhodium carbonyl hydride, i.e. SEP complex, plus SEP system. For comparison, detailed data will be also provided on the know tris-(triphenyl phosphine) rhodium carbonyl hydride, i.e. TPP complex, plus TPP system. This will be followed by short descriptions of the catalytic behavior of various substituted and unsubstituted alkyl diphenyl phosphines. Finally, an example of a continuous hydroformylation process based on the SEP system will be described.

EXAMPLE 93

Tris-(Trimethylsilylethyl Diphenyl Phosphine) Rhodium Carbonyl Hydride as a Catalyst in the Presence of 140-Fold Ligand Excess at Different Temperatures The complex of Example 48 was studied at the 107 ppm rhodium level in the presence of 140-fold trimethylsilylethyl diphenyl phosphine (SEP) ligand as a butene hydroformylation catalyst using the general procedure. Comparative experiments were run using 107 ppm rhodium as a tris-(triphenyl phosphine) carbonyl hydride complex with 140-fold triphenyl phosphine (TPP). Reaction rates, n/i product ratios, conversions and by-products were determined at various temperatures. The results are shown by Table 7.

The data of the table show that both the SEP and the TPP based catalyst systems are highly active and produce a high ratio of n/i products at most temperatures. However, the temperature dependence of the two systems is very different.

TABLE 8

HYDROFORMYLATION AT DIFFERENT TEMPERATURES

Feed: Butene-1 and 1:4 $CO/H_2$ at 350 psi
Catalyst: $L_3Rh(CO)H$, Rh 107 ppm, Rh/L = 140
SEP Ligand: $(CH_3)_3SiCH_2CH_2PO_2$ TPP Ligand: $O_3P$

| | Variable Conditions of Catalysis | | Reaction Rates and Selectivities | | | | By-Product, Mole % in Product Mixture | | Details | |
|---|---|---|---|---|---|---|---|---|---|---|
| Seq. No. | Catalyst Ligand | Reaction Temp., °C. | Fraction of $CO/H_2$ Reacted k, min$^{-1}$ | Product n/i Ratio | Reaction Time Min. | Butene Conversion % | Butane | Butene-2 | Exact Rh Conc. ppm | Exp. Run No. |
| 1 | SEP | 100 | 0.03 | 6.1 | 35 | 86.9 | 2.0 | 3.8 | 106 | 104 |
| 2 | | 120 | 0.10 | 6.2 | 35 | 96.5 | 9.4 | 6.2 | 106 | 110 |

TABLE 8-continued

HYDROFORMYLATION AT DIFFERENT TEMPERATURES

Feed: Butene-1 and 1:4 $CO/H_2$ at 350 psi
Catalyst: $L_3Rh(CO)H$, Rh 107 ppm, Rh/L = 140
SEP Ligand: $(CH_3)_3SiCH_2CH_2PO_2$  TPP Ligand: $O_3P$

| | Variable Conditions of Catalysis | | Reaction Rates and Selectivities | | | | By-Product, Mole % in Product Mixture | | Details | |
|---|---|---|---|---|---|---|---|---|---|---|
| Seq. No. | Catalyst Ligand | Reaction Temp., °C. | Fraction of $CO/H_2$ Reacted k, min$^{-1}$ | Product n/i Ratio | Reaction Time Min. | Butene Conversion % | Butane | Butene-2 | Exact Rh Conc. ppm | Exp. Run No. |
| 3 | | 140 | 0.21 | 5.7 | 15 | 97.5 | 14.5 | 12.4 | 108 | 109 |
| 4 | | 145 | 0.27 | 5.0 | 15 | 95.2 | 11.9 | 12.1 | 109 | 115 |
| 5 | TTP | 100 | 0.21 | 7.5 | 35 | 98.9 | 10.7 | 12.1 | 107 | 100 |
| 6 | | 120 | 0.34 | 5.9 | 10 | 97.3 | 9.3 | 12.2 | 104 | 112 |
| 7 | | 140 | 0.38 | 3.4 | 10 | 98.2 | 11.2 | 21.9 | 105 | 113 |
| 8 | | 145 | 0.27 | 2.4 | 15 | 97.7 | 11.9 | 26.0 | 103 | 114 |

The novel SEP catalyst system exhibits an increasing activity with elevated temperatures. At 100° C. and 120° C. the n/i ratio of products is about the same and there is only a small n/i drop at 145° C. High butene conversion is observed at all temperatures. The only adverse effect of temperature increase is the increased hydrogenation and isomerization of the butene-1 reactant. The SEP system remains clear, bright yellow in appearance, even at 145° C.

Figure 5A:
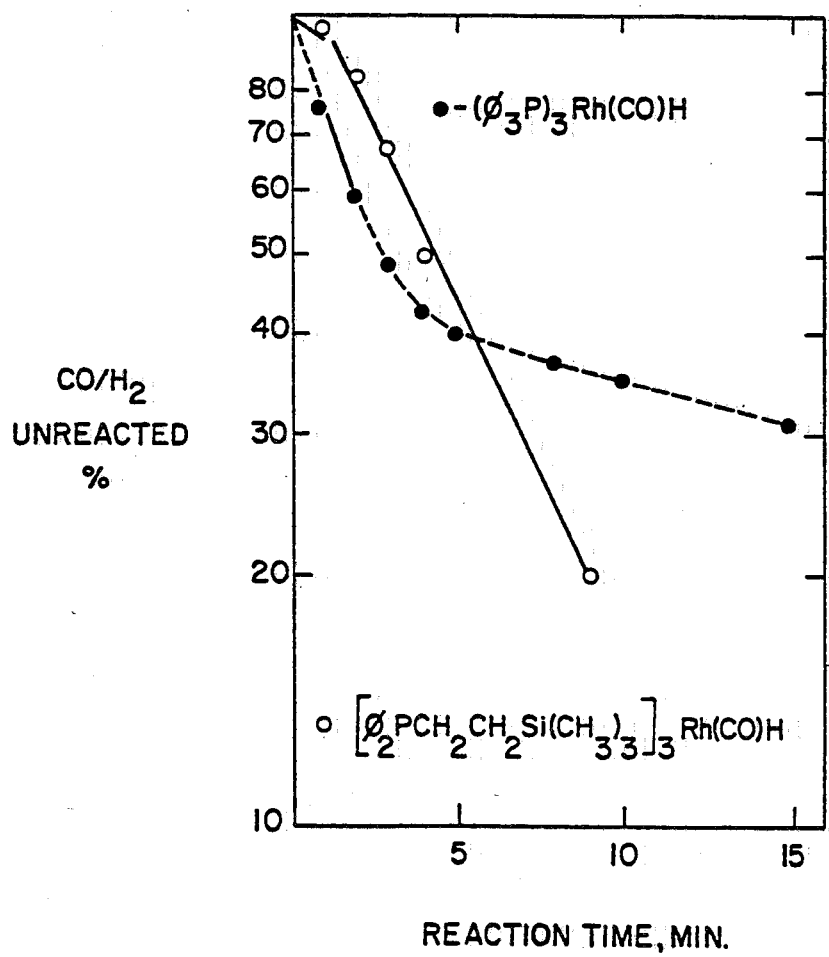
FIG. 5A is a graphical comparison of certain cataysts stabilities at high temperature hydroformylation of butene-1.
Figure 5B:
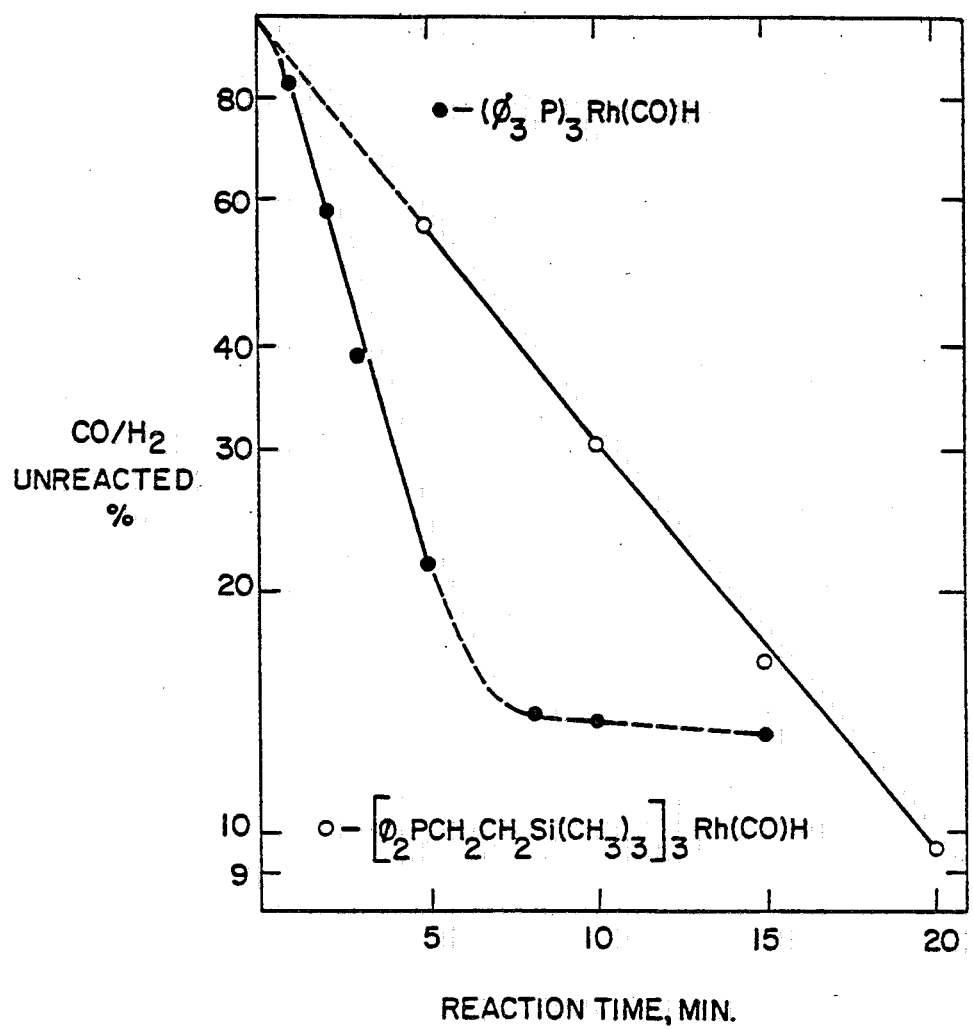
FIG. 5B is a graphical comparison of certain catalyst stabilities at low ligand/Rh ratio in Hydroformylation of butene-1.

The known TPP catalyst system exhibits the same increased activity at 120° C. and 140° C. However, the n/i ratios in this case are dramatically reduced with increasing temperatures. At 145° C., and n/i ratio products is significantly lower in the TPP than in the SEP system. At 145° C., the reaction rate of the TPP system also drops. Decomposition of this system at this temperature is indicated by darkening of the reaction mixture. The behavior of the SEP and TPP systems is compared by FIGS. 5A and 5B.

Figure 6:
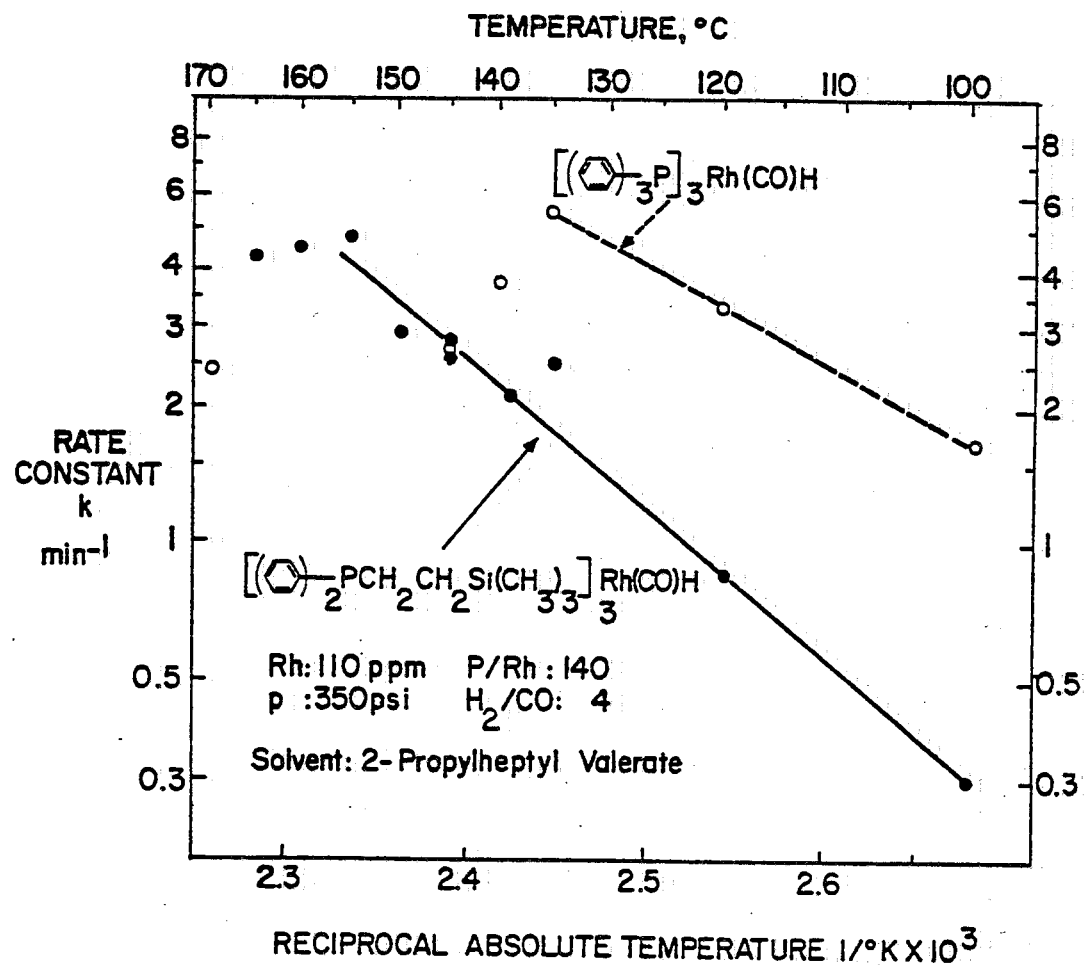
FIG. 6 is a graphical representation of butene hydroformylation rate versus temperature correlations in the presence of SEP and TPP based rhodium-phosphine complex catalysts.

The results of similar but more extensive studies are shown in FIGS. 6 to 9. FIG. 6 correlates the hydroformylation rate with the temperature. It shows that in the presence of the SEP complex catalyst, the rates of 1-butene hydroformylation were increasing with elevated temperatures up to 155° C. In the case of the TPP catalyst, increased rates were observed only to about 135° C. Beyond these temperatures, reduced hydroformylation rates were observed apparently due to catalyst decomposition.

Figure 7:
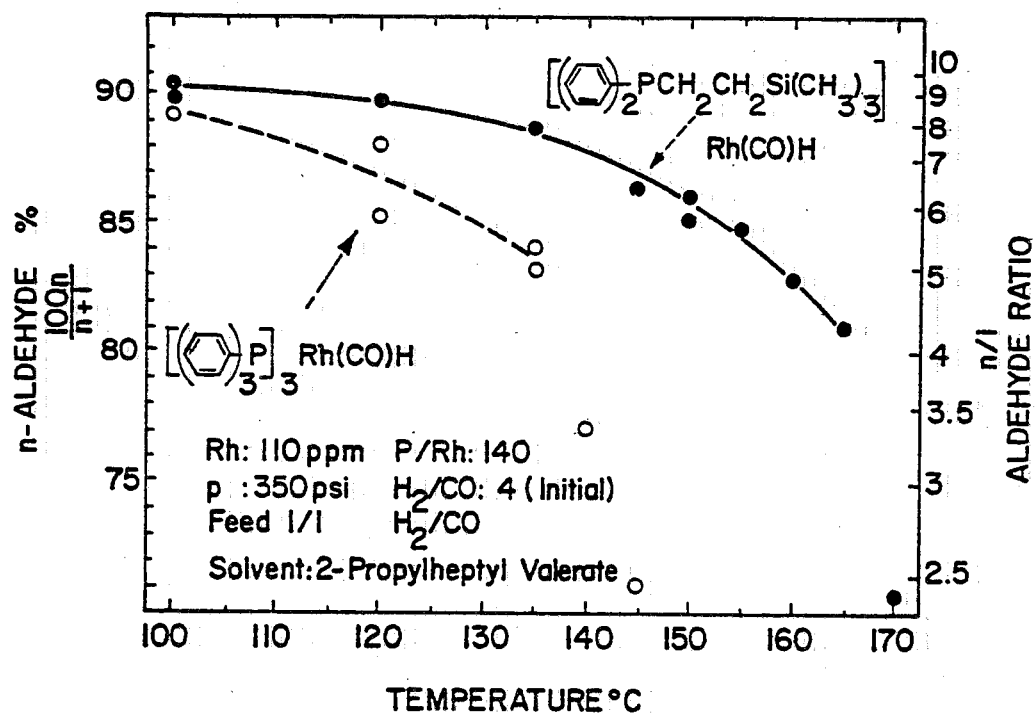
FIG. 7 is a graphical representation of 1-butene hydroformylation temperature versus n-valeraldehyde (n) to total valeraldehyde (n+i) ratio correlations in the presence of SEP and TPP based rhodium-phosphine complex catalysts.
Figure 8:
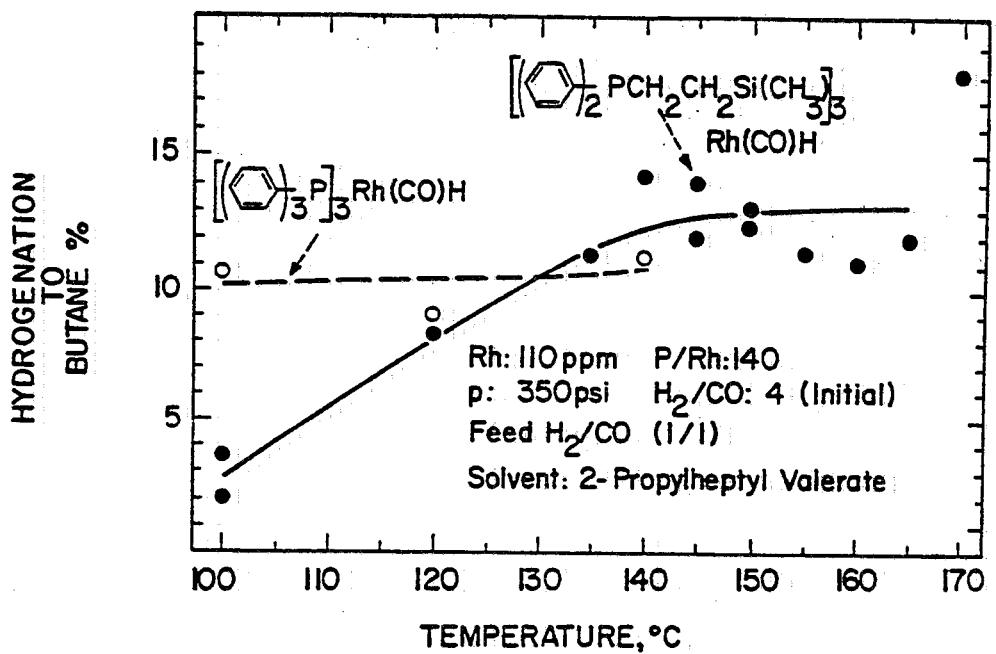
FIG. 8 is a graphical representation of 1-butene hydroformylation temperature versus butane by-product formation correlations in the presence of SEP and TPP based complex catalysts.

FIG. 7 correlates the hydroformylation temperature with the selectivity for producing the linear (n-) versus branched (i-) aldehyde. It is shown that the n/i ratios depend on the temperature in the case of both catalysts.

When hydroformylations are carried out above the stable temperature range of the catalysts, a drastic drop in the n/i ratios is observed. This drop occurs above 165° C. for the SEP catalyst and above 135° C. for the TPP catalyst. At the same hydroformylation temperature, the use of the SEP catalyst leads to somewhat higher n/i ratios. It appears that the SEP catalyst could be used at an about 20° C. higher hydroformylation temperature than the TPP catalyst and would still exhibit a selectivity equal to that of TPP at the lower temperature.

With regard to the undesired hydrogenation of the 1-butene feed to produce n-butane (FIG. 8), it is noted that, in the case of the SEP catalyst, the percentage of n-butane formed more than triples to about 11% when the reaction temperature is increased from 100° C. to 135° C. However, there is very little increase between 135° C. and 165° C. In contrast, limited data indicate that, in the case of the TPP catalyst, the level of hydrogenation stays around the 10% level between 100° C. and 140° C.

Figure 9:
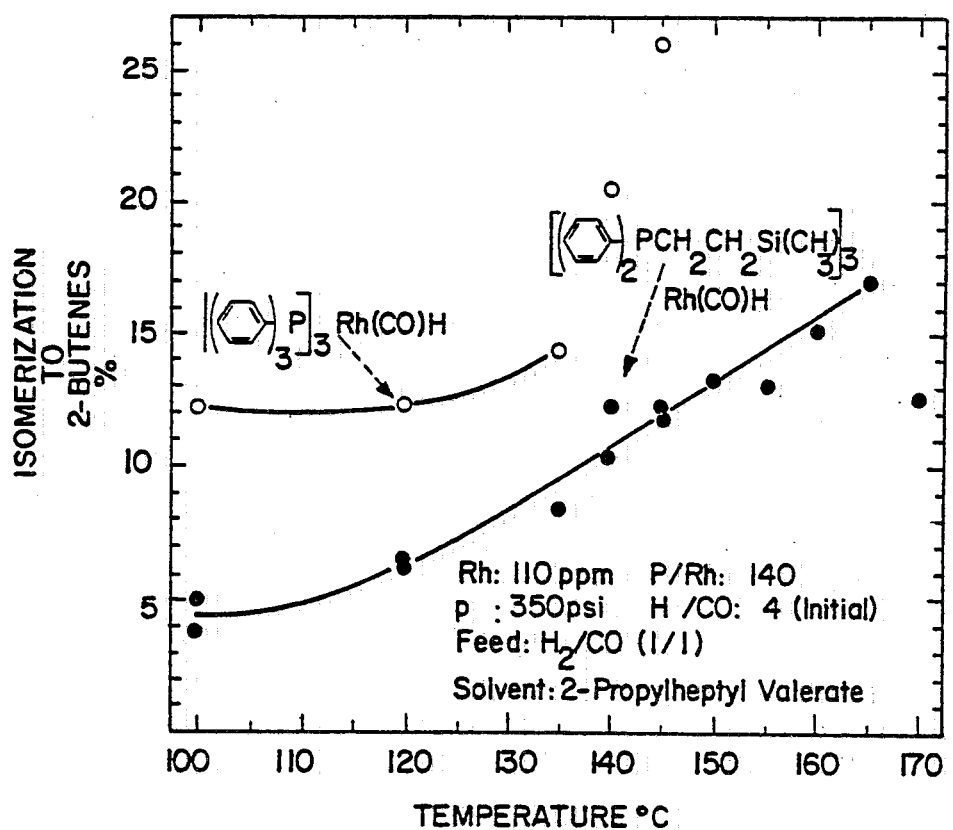
FIG. 9 is a graphical representation of 1-butene hydroformylation temperature versus 2-butenes by-product formation correlations in the presence of SEP and TPP complex catalysts.

The behavior of the SEP and TPP catalysts appears to be also different with respect to the isomerization of the 1-butene feed to cis- and trans-butene-2 by-products (FIG. 9). In general, less isomerization occurs when the SEP catalyst is used. However, the percentage of isomerized olefin is increased with temperature in the presence of both catalysts, up to 165° C. When the SEP catalyst becomes unstable at 170° C., less 2-butenes by-products are obtained apparently due to secondary reactions, i.e., hydrogenation and hydroformylation. In contrast, the thermal destabilization of the TTP catalyst in the 140°–145° range results in a large increase of the percentage of 2-butenes in the reaction mixture.

Example 94

Tris-(Trimethylsilylethyl Diphenyl Phosphine) Rhodium Carbonyl Hydride as a Catalyst at Different Levels of Excess Ligand Concentrations The complex catalyst of Example 48 was studied mainly at the 105 ppm rhodium level and at 100° C. reaction temperature to determine the effect of the excess trimethylsilylethyl diphenyl phosphine ligand (SEP). The SEP concentration used ranged from 5 to 149 mmole per liter. Some comparative experiments were also carried out using tris-(triphenyl phosphine) rhodium carbonyl hydride and varying excess concentrations of the corresponding triphenyl phosphine ligand (TTP). The results of these studies are shown in Table 8.

The data of Table X show that, in general, increasing concentrations of excess ligand result in decreased reaction rates but sharply increased selectivities, i.e., n/i ratios, in both the novel and the known catalyst systems. There is an apparent inhibition and stabilization of both systems at high ligand concentrations. However, the behavior of the two catalysts is significantly different at relatively low excess ligand concentrations.

TABLE 8

HYDROFORMYLATION AT DIFFERENT LEVELS OF EXCESS LIGAND CONCENTRATIONS

Feed: Butene-1 and 1:4 $CO/H_2$ at 350 psi
Catalyst: $L_3Rh(CO)H$
SEP Ligand: $(CH_3)_3SiCH_2CH_2PO_2$
TPP Ligand: $O_3P$

| | | Variable Conditions of Catalysis | | | | Reaction Rates and Selectivities | | | |
|---|---|---|---|---|---|---|---|---|---|
| Seq. No. | Catalyst Ligand | Reaction Temp. °C. | Auto-Clave | Excess Ligand Conc. mMole/lit. | Rhodium Conc. ppm | Ligand to Rh Ratio L/Rh | Fraction of $CO/H_2$ Reacted k min-1 | Product Linearity Ratio, n/i | Reaction Time min. | CO Conversion % |
| 1 | SEP | 100 | H | 5 | 105 | 5.2 | 0.24 | 3.5 | 20 | 88.7 |
| 2 | | | | 24 | 105 | 24.2 | 0.09 | 4.0 | 35 | 87.1 |
| 3 | | | S | 28 | 105 | 28 | 0.12 | 4.4 | 35 | 88.0 |
| 4 | | | | 56 | 217 | 28 | 0.12 | 5.4 | 30 | 94.2 |
| 5 | | | | 143 | 105 | 143 | 0.03 | 6.1 | 35 | 83.6 |
| 6 | | 120 | S | 29 | 105 | 29 | 0.30 | 4.5 | 15 | 93.0 |
| 7 | | | | 60 | 210 | 30 | 0.25 | 5.7 | 15 | 89.6 |
| 8 | | | | 149 | 105 | | 0.10 | 6.2 | 35 | 88.1 |
| 9 | TPP | 100 | H | 5 | 105 | 5 | 0.28 | 3.0 | 15 | 80.8 |
| 10 | | | | 142 | 102 | 142 | 0.17 | 3.8 | 35 | 96.5 |
| 11 | | | S | 27 | 105 | 27 | 0.31 | 4.7 | 15 | 86.6 |
| 12 | | | | 143 | 104 | 143 | 0.03 | 6.1 | 35 | 83.6 |

The novel SEP catalyst system leads to higher n/i product ratio than the TPP system at five mmole/l excess ligand concentration (Seq. No. 1 vs. Seq. No. 9). At the intermediate SEP concentration of 56 mmole, there is a good selectivity and sufficient reaction rate (Seq. No. 4). It is interesting to observe that the positive effect of increasing catalyst complex concentration on the reaction rate can be counter-balanced by the inhibiting effect of increased SEP concentration (compare Seq. Nos. 3 vs. 4 and 6 vs. 7). Clearly, the SEP concentration is more important than the SEP/Rh ratio. AT the high SEP level of 143, there is some further increase in the n/i ratio, but reaction rate is cut to about one fourth (compare Seq. Nos. 4 and 5). At this level, the rate can be increased while maintaining the high n/i ratio by increasing the reaction temperature (see Seq. No. 8 and the table of the previous example).

The effect of different ligand to rhodium ratios on the n/i ratios of butene hydroformylation at different temperatures was further examined. The results are summarized by FIG. 10.

The figure shows that as the SEP/Rh ratio changes from about 140 to about 1000, the n/i ratios at 80% conversion changes from about 2 to 7. The major change in the percentage of the n-aldehyde product occurs in the 140 to 500 L/Rh range. It was shown in additiional experiments that there was very little further selectivity increase when the SEP ligand was used as the solvent (i.e., in about 75% concentration).

The increased selectivity to linear aldehyde is a consequence of the increased catalyst stability in these experiments. The increased catalyst stability is also reflected in a decreasing darkening of the reaction mixture with increasing ligand concentration. Another sign of the increased stability is the better maintenance of the hydroformylation rate with increasing conversion. Finally, it was also noted that the increased ligand concentration resulted in a moderate suppression of the rate of hydrogenation. Nevertheless, hydrogenation remained significant enough to cause a decreasing $H_2/CO$ ratio during the reaction.

Figure 10:
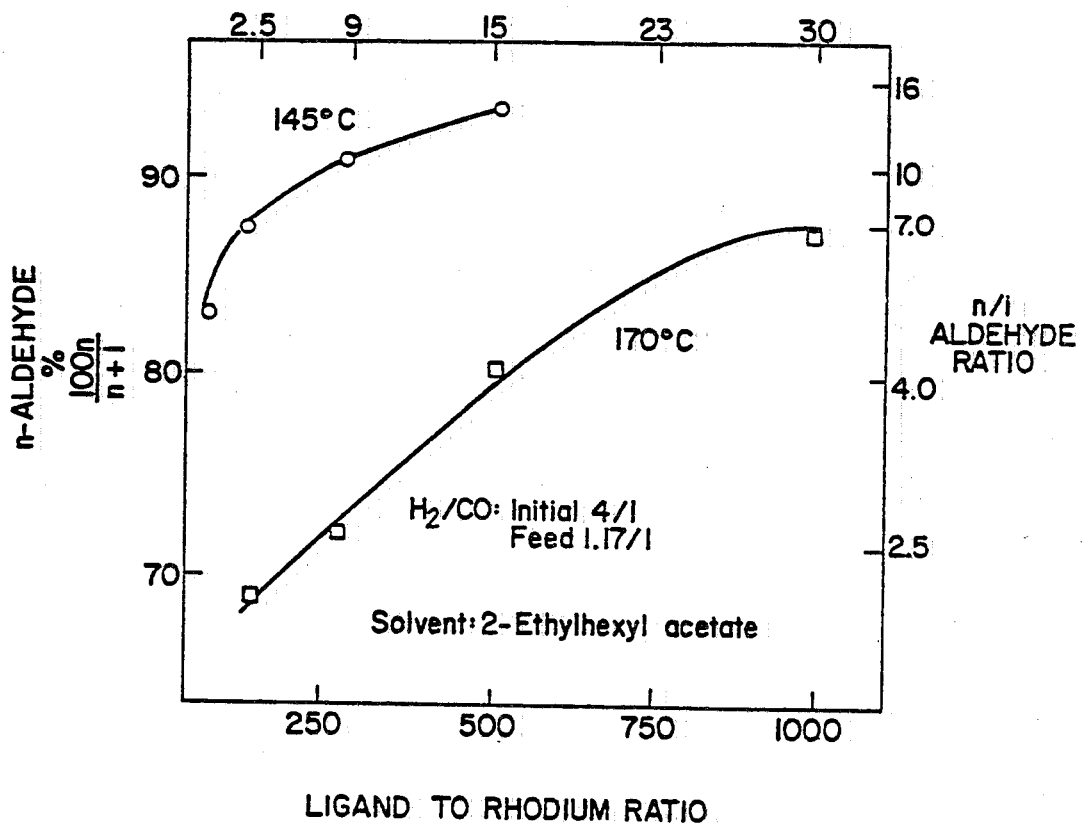
FIG. 10 is a graphical representation of the effect of SEP ligand to rhodium ratio on selectivity of butene hydroformulation at 145° and 170° C.

Similar studies of the effect of increased SEP/Rh ratio were carried out at 160°, 145° and 120° C. The data obtained at 145° are also shown in FIG. 10. The lower the reaction temperature, the less effect of increased L/Rh ratios was observed. At decreasing temperatures, most of the effects were observed in the range of increasingly low L/Rh ratios. Also, the main effect was on selectivity rather than on stability.

Example 95

Hydroformylation Selectivity of Tris-(Trimethylsilylethyl Diphenyl Phosphine) Rhodium Carbonyl Hydride Excess Ligand Catalyst System at Different Olefin Conversions, i.e. At Different Carbon Monoxide Concentrations Butene-1 was hydroformylated in the Hastalloy unit according to the general procedure. The catalyst and ligand concentrations were higher than usual and the reaction conditions milder as shown in Table 9. The reaction mixture was frequently sampled during the process and the samples were analyzed by gc to determine the relative selectivities to n- and i- aldehyde products and hydrocarbon by-products as a function of butene-1 conversion. The detailed data are given in Table 9.

The data of Table 9 indicate that the n- to i-ratio of aldehydes in the reaction is decreasing as the conversion increases. Up to about 60% butene conversion, the n/i ratio stays above 18.5, although it is steadily dropping (see Sample Nos. 1-2). In the 72–78% conversion range, the n/i ratio is about 14. Once butene-1 conversion reaches 90%, the n/i ratio of the product mixture is down to about 11.5.

TABLE 9

HYDROFORMYLATION SELECTIVITY AT DIFFERENT OLEFIN CONVERSION LEVELS

Feed: Butene-1 and 1:4 $CO/H_2$ at 130 psi at 110° C. under 130 psi
Catalyst: $L_3RH(CO)H$, Rh 212 ppm, L Excess 300 mMole, L/Rh 140
L: $OPCH_2CH_2Si(CH_3)_3$

| | Conversion Related Data | | | Aldehyde | Mole % Selectivity to Various Compounds | | | |
|---|---|---|---|---|---|---|---|---|
| Sample No. | Butene-1 Conversion % | Conversion % Based on $CO/H_2$ Consumed | Reaction Time, Min. | Product Linearity Ratio, n/i | Aldehyde Products n | Aldehyde Products i | Butane Hydrogenation Product | 2-Butene By-Products cis | 2-Butene By-Products trans |
| 1 | 26.4 | 21.9 | 10 | 26 | 68.4 | 2.7 | 11.9 | 9.7 | 7.3 |

TABLE 9-continued
HYDROFORMYLATION SELECTIVITY AT DIFFERENT OLEFIN CONVERSION LEVELS Feed: Butene-1 and 1:4 $CO/H_2$ at 130 psi at 110° C. under 130 psi
Catalyst: $L_3RH(CO)H$, Rh 212 ppm, L Excess 300 mMole, L/Rh 140
L: $OPCH_2CH_2Si(CH_3)_3$

| | Conversion Related Data | | Aldehyde | Mole % Selectivity to Various Compounds | | | |
|---|---|---|---|---|---|---|---|
| Sample No. | Butene-1 Conversion % | Conversion % Based on CO/H2 Consumed | Reaction Time, Min. | Product Linearity Ratio, n/i | Aldehyde Products n i | Butane Hydrogenation Product | 2-Butene By-Products cis trans |
| 2 | 46.9 | 36.0 | 15 | 25 | 77.9  3.1 | 7.4 | 6.7  4.9 |
| 3 | 61.6 | 50.0 | 20 | 18.5 | 79.7  4.3 | 6.1 | 5.8  4.2 |
| 4 | 72.0 | 61.4 | 25 | 13.9 | 80.2  5.8 | 5.2 | 5.2  3.7 |
| 5 | 78.0 | 69.4 | 30 | 14.0 | 79.6  5.7 | 5.4 | 5.4  3.9 |
| 6 | 90.0 | 79.9 | 40 | 11.6 | 82.1  7.1 | 3.9 | 4.0  2.9 |
| 7 | 90.5 | 87.9 | 60 | 11.3 | 81.9  7.2 | 4.0 | 4.0  3.0 |

It was also observed that during the conversion of about 25% of the butene, the total aldehydes to hydrocarbon by-products ratio was lower than at higher conversions (about 70/30 versus 90/10). It is believed that this is due to uncontrolled nonequilibrium conditions early during the reaction. Almost all the hydrogenation occurred during the first 10 minutes of the reaction. During the early, very fast part of the reaction, the liquid reaction medium became starved of CO. Due to the resulting low CO partial pressure, the n/i product ratio became very high. However, the amount of CO during some of this period was so insufficient that much hydrogenation and isomerization occurred. In a continuous process, where the low optimum concentration of CO could be more accurately maintained, high selectivity to aldehydes could be better achieved without producing significant amounts of by-products.

Example 96

Hydroformylation with the Tris-(Trimethylsilylethyl Diphenyl Phosphine) Rhodium Complex System In a series of experiments, tris-(triphenyl phosphine) rhodium carbonyl hydride was reacted with a varying excess concentration of the novel substituted diaryl alkyl phosphines. This resulted in the formation of the novel catalysts of the present invention which were studied for their catalytic properties in the usual manner in the Hastalloy unit (H).

Tris-(triphenyl phosphine) rhodium carbonyl hydride, 0.1 g (0.1 mmole), was mixed with 80 g of a mixture of 4 g (14 mole) of trimethylsilylethyl diphenyl phosphine and 76 g 2-propylheptyl valerate to provide an SEP catalyst system. For comparison, the same complex was also mixed with 80 g of a mixture of 3.7 g (14 mole) of triphenyl phosphine to provide a TPP catalyst system. This provided two systems having 105 ppm rhodium and a 140 fold ligand excess.

Butene hydroformylations were then carried out with both catalyst systems at 100° C. in the usual manner. The results indicated that the main catalytic species of the SEP system is a SEP complex. The reaction rate of the SEP system was about 1/6 of the TPP system (k min$^{-1}$ values of 0.02 and 0.12, respectively). The n/i product ratios were about the same (4.2).

Other SEP catalyst systems were made up the same way except for the different L/Rh ratios: 25 and 5. They were also employed successfully for butene hydroformylation.

Example 97

Hydroformylation with the Tris-(Trimethylsilylethyl Diphenyl Phosphine System at Different H2/CO Ratios For a further study of the effect of the $H_2/CO$ ratios on hydroformylation selectivity, the feed gas was provided through the side arm of the autoclave to provide conditions during the reaction which are closer to equilibrium. This type of operation was specific to this example.

The SEP complex catalyst was formed in situ during hydroformylation from acetylacetonato dicarbonyl rhodium. The $H_2/CO$ ratios of both the initial $H_2/CO$ gas and the final unreacted synthesis gas, in the head space of the autoclave, were analyzed. The $H_2CO$ ratio of the feed gas was adjusted to keep the initial and final $H_2/CO$ ratios the same as much as possible.

The results are shown by Table 10. The data show that as the $H_2/CO$ ratio was increased from 1 to 20 the ratio of n- to i- aldehydes was increased. It is also interesting to note that having the side arm feed resulted in much less 1-butene isomerization and hydrogenation than obtained previously with top feeding.

TABLE 10
1-BUTENE HYDROFORMYLATION WITH SYNTHESIS GAS OF VARYING H2/CO RATIO IN THE PRESENCE OF SEP COMPLEX AND TPP COMPLEX CATALYSTS

Total Pressure 350 psi (260 Atm.); Catalyst: $L_3Rh(CO)H$; L/Rh = 140, Rh = 110 ppm
Solvent: 2-Ethylhexyl Acetate

| Seq. No. | Ligand | Reaction Temp. °C. | H2/CO Ratio Initial | H2/CO Ratio Feed | H2/CO Ratio Final | CO Partial Pressure pCO, psi Initial | CO Partial Pressure pCO, psi Final | Fraction of H2/CO Reacted Rate Constant k, min$^{-1}$ | Fraction of H2/CO Reacted Conversion % | Reaction Time, Min. | Aldehyde Product Linearity Ratio n/i | Aldehyde Product Linearity 100 n % n + i | Selectivities to Various Compounds, % Aldehydes n | Selectivities to Various Compounds, % Aldehydes i | Selectivities to Various Compounds, % Butane | Selectivities to Various Compounds, % 2-Butene |
|---|---|---|---|---|---|---|---|---|---|---|---|---|---|---|---|---|
| 1 | SEP | 120 | 1.18 | 1.08 | 1.36 | 160 | 149 | 0.115 | 81 | 13 | 3.09 | 7.56 | 73.7 | 23.8 | 0.6 | 1.8 |
| 2 | SEP | 120 | 5.0 | 1.08 | 4.8 | 59 | 60 | 0.082 | 81 | 22 | 4.56 | 8.20 | 78.2 | 17.1 | 1.7 | 2.9 |
| 3 | SEP | 120 | 10.0 | 1.08 | 7.8 | 31 | 39 | 0.090 | 82 | 30 | 6.60 | 86.8 | 80.8 | 12.2 | 2.8 | 3.2 |
| 4 | SEP | 120 | 15.0 | 1.17 | 10.4 | 22 | 30 | 0.116 | 81 | 15 | 8.22 | 89.2 | 80.4 | 9.8 | 4.4 | 5.3 |
| 5 | TPP | 90 | 1.08 | 1.08 | 1.8 | 168 | 125 | 0.060 | 81 | 29 | 3.76 | 79.0 | 77.0 | 20.5 | 0.8 | 1.7 |
| 6 | TPP | 90 | 5.0 | 1.08 | 9.0 | 59 | 35 | 0.059 | 81 | 28 | 5.50 | 84.6 | 80.5 | 14.7 | 1.2 | 3.6 |
| 7 | TPP | 90 | 10.0 | 1.08 | 10.5 | 31 | 30 | 0.062 | 80 | 26 | 6.70 | 87.0 | 81.0 | 12.1 | 2.0 | 4.8 |

TABLE 10-continued

1-BUTENE HYDROFORMYLATION WITH SYNTHESIS GAS OF VARYING $H_2/CO$ RATIO IN THE PRESENCE OF SEP COMPLEX AND TPP COMPLEX CATALYSTS

Total Pressure 350 psi (260 Atm.); Catalyst: $L_3Rh(CO)H$; L/Rh = 140, Rh = 110 ppm
Solvent: 2-Ethylhexyl Acetate

| Seq. No. | Ligand | Reaction Temp. °C. | $H_2/CO$ Ratio Initial | Feed | Final | CO Partial Pressure pCO, psi Initial | Final | Fraction of $H_2/CO$ Reacted Rate Constant k, min$^{-1}$ | Conversion % | Reaction Time, Min. | Aldehyde Product Linearity Ratio n/i | 100 n % n + i | Selectivities to Various Compounds, % Aldehydes n | i | Butane | 2-Butene |
|---|---|---|---|---|---|---|---|---|---|---|---|---|---|---|---|---|
| 8 | TPP | 90 | 15 | 1.17 | 18 | 22 | 18 | 0.062 | 80 | 26 | 8.70 | 89.7 | 80.2 | 9.2 | 4.6 | 6.0 |

Comparative side arm feed experiments were also carried out using the known TPP catalyst system at the same concentration. At 120° C., significant side reaction continued to occur. Apparently, equilibrium conditions were not sufficiently approached. Consequently, further experiments were carried out at 90° C. where the reaction rate is sufficiently slow to avoid side reactions. The results are also shown in Table 10. They show that TPP at 90° C. exhibits a similar behavior to that of SEP at 120° C. The n/i ratios are slightly higher for TPP, apparently due to a higher average of $H_2/CO$ ratios.

Example 98

Figure 11:
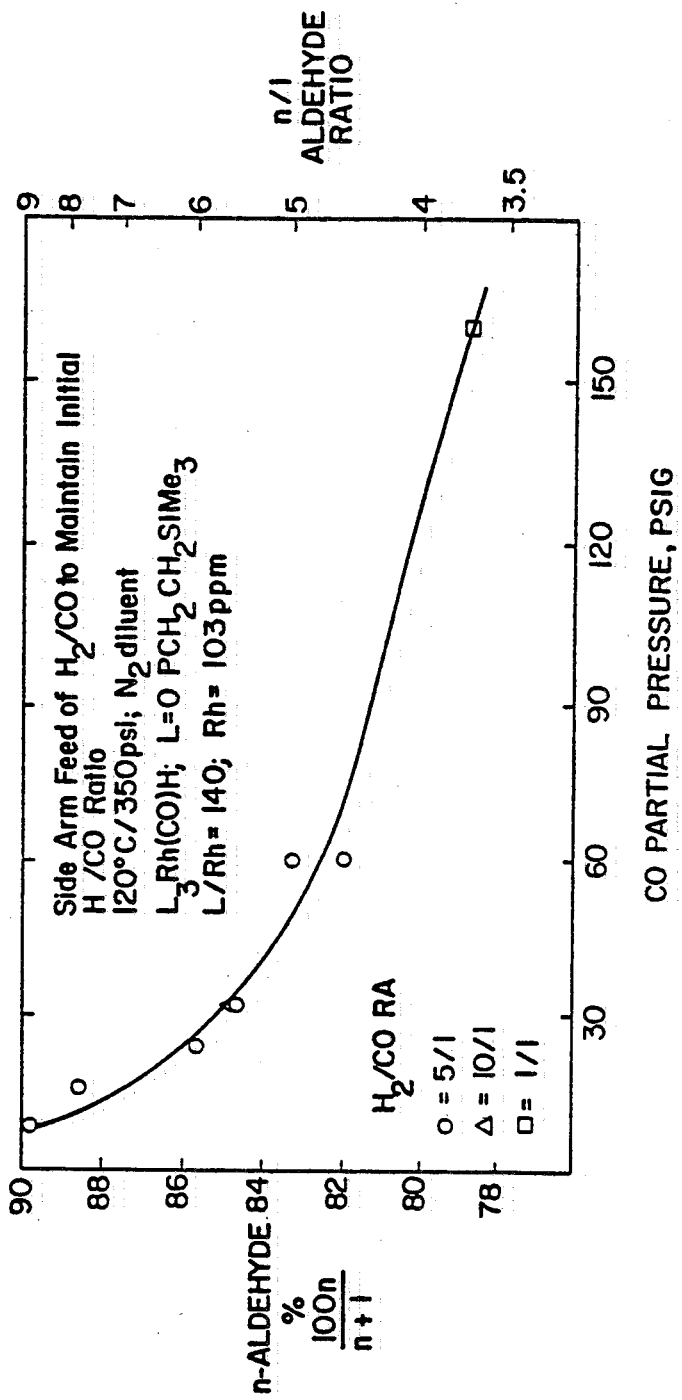
FIG. 11 is a graphic representation of the effect of carbon monoxide pressure on ratio of n-valeraldehyde (n) to total valeraldehyde (n+i) product of 1-butene hydroformylation.

Hydroformylation with the Tris-(Trimethylsilylethyl Diphenyl Phosphine Rhodium Complex System at Different CO Partial Pressures The results of the type of experiments described in Example 97 were plotted in FIG. 11 to show the dependence of n/i aldehyde product ratios on the CO partial pressures. In additional experiments the $H_2/CO$ ratios were kept constant with changing CO partial pressures by maintaining an appropriate fraction of the total 350 psi (26 Atm.) gas pressure by $N_2$ gas. There was relatively little change in reaction rates.

FIG. 10 shows that decreasing CO partial pressures result in higher n/i product ratios even though the $H_2/CO$ ratio is kept constant. The dependence of the n/i ratios is particularly strong in the low CO partial pressure range.

Example 99

Comparative Hydroformylation with Tris-(Trihydrocarbylsilylalkyl Diphenyl Phosphine) Carbonyl Hydride Based Catalyst Systems In a series of experiments, the results of which are shown in Table 11, various silyl substituted alkyl diphenyl phosphine complexes were tested as 1-butene hydroformylation catalysts under standard test conditions, using top synthesis gas feed.

TABLE 11

1-BUTENE HYDROFORMYLATION IN THE PRESENCE OF VARIOUS TRIS(SILYL SUBSTITUTED ALKYL DIPHENYL PHOSPHINE) RHODIUM CARBONYL HYDRIDE COMPLEX CATALYSTS

Catalyst: $L_3Rh(CO)H$, Rh = 107 ppm, L/Rh = 140
Pressure: 350 psi (26 Atm)
L = $Ph_2PR$; $R_1$ = $CH_2CH_2SiC_3H_7$; $R_2$ = $CH_2CH_2SiPh_3$; $R_3$ = $[Ph_2PCH_2CH_2]_2Si(CH_3)_2$;
$R_4$ = $CH_2CH_2CH_2Si(CH_3)_3$; $R_5$ = $CH_2Si(CH_3)_3$

| Seq. No.* | Ligand LR | Example No. of Complex | Reaction Temp. °C. | $H_2/CO$ Ratios Initial | Feed | Final | Rate Constant k, min$^{-1}$ | Conversion % | Reaction Time Min. | Ratio n/i | $\frac{100n}{n+i}$, % | Selectivity to Various Compounds, % Aldehyde Products, % n | i | Butane | 2-Butene |
|---|---|---|---|---|---|---|---|---|---|---|---|---|---|---|---|
| 1a | LR$_1$ | 49 | 120 | 5 | 1.08 | 3.6 | 0.072 | 80 | 30 | 8.90 | 89.9 | 63.4 | 7.1 | 20.2 | 9.3 |
| 1b | LR$_1$ | 49 | 145 | 5 | 1.27 | 3.8 | 0.274 | 80 | 8 | 9.62 | 90.6 | 61.1 | 6.4 | 18.4 | 14.3 |
| 2 | LR$_2$ | 50 | 145 | 5 | 1.27 | 7.1 | 0.132 | 80 | 30 | 7.59 | 88.4 | 73.6 | 9.7 | 8.3 | 8.3 |
| 3 | LR$_2$ | 51 | 145 | ~4 | ~1 | — | 0.157 | 80 | 12 | 7.6 | 88.4 | — | — | — | — |
| 4a | LR$_4$ | 52 | 120 | 5 | 1.03 | 3.7 | 0.069 | 81 | 34 | 8.34 | 89.3 | 69.9 | 8.4 | 13.2 | 8.5 |
| 4b | LR$_4$ | 52 | 145 | 4 | ~1 | 2.3 | 0.260 | 82 | 9 | 5.80 | 85.3 | 67.6 | 11.7 | 10.9 | |
| 5 | LR$_5$ | 53 | 100 | 5 | 1.05 | 5 | 0.056 | 78 | 60 | 6.24 | 86.2 | 54.3 | 8.1 | 31.8 | 5.9 |

*Experiments of Seq. No. 1a and 1b were carried out in 2-ethylhexyl acetate as a solvent. The rest were in 2-propylheptyl valerate.

The data indicate, that with the exception of the last catalyst, the complexes tested show the same type of catalyst behavior as the previously discussed SEP complex. The last complex tested, i.e., the one based on the trimethylsilylmethyl ligand, was unstable. It showed less selectivity than the others even at the relatively low hydroformylation temperature used in this case.

Example 100

Hydroformylation with Various Tris(Alkyl Diphenyl Phosphine) Rhodium Carbonyl Hydride Catalysts In a series of standard experiments, the results of which are shown in Table 12 various tris-(alkyl diphenyl phosphine) rhodium complexes was tested as 1-butene hydroformylation catalysts. It is emphasized that a 4 to 5 $H_2/CO$ ratio and a 140 L/Rh ratio was used in these tests, in contrast to published work with similar systems.

Overall, all of the n-alkyl diphenyl phosphine complexes exhibited similar catalytic behavior (Seq. Nos. 1-11). At sufficiently elevated temperatures, where they were active and stable, highly linear aldehyde products were selectively produced at a high rate. This is in contrast to the published low temperature results by Sanger and others which were referred to earlier.

It is noted that the ligand volatility in the ethyl-, propyl- and butyl- diphenyl phosphine complex systems was found to be too high for their application in a continuous product flashoff process. In contrast, the ligand of the novel tris-(hexyl diphenyl phosphine) rhodium complex showed no objectionable volatility (see Example 110). Other $C_6$ or higher alkyl substituents of appropriate structure can also provide the desired reduced volatility.

lyst selectivity (Seq. Nos. 10 and 11). This is again a consequence of the steric inhibition of tris-phosphine

TABLE 12

1-BUTENE HYDROFORMYLATION IN THE PRESENCE OF VARIOUS TRIS (ALKYL DIPHENYL PHOSPHINE) RHODIUM CARBONYL HYDRIDE CATALYSTS

Catalyst: $L_3Rh(CO)H$, L/Rh = 140; Rh = 140 ppm; Percursor Dicarbonyl Acetylacetonate Rhodium, Total Pressure 350 psi (~26 Atm)
L: $Ph_2PR$; $R_1 = CH_2CH_3$; $R_2 = (CH_2)_2CH_3$ $R_3 = (CH_2)_3CH_3$; $R_4 = CH(CH_3)C_2H_5$;
$R_5 = CH_2CH_2C(CH_3)_3$; $R_6 = CH_2C(CH_3)_3$.

| Seq.* No. | Ligand LR' | Reaction Temp. °C | H2/CO Ratio Initial | H2/CO Ratio Feed | H2/CO Ratio Final | Rate Constant k, min⁻¹ | Fraction of H2/CO Reacted Conversion % | Reaction Time Min. | Aldehyde Product Ratio n/i | Aldehyde Product Linearity $\frac{100n}{n+i}$, % | Aldehyde Products n | Aldehyde Products i | Butane | 2-Butenes |
|---|---|---|---|---|---|---|---|---|---|---|---|---|---|---|
| 1 | LR1 | 120 | 4.9 | 1.041 | 4.6 | 0.045 | 80 | 41 | 8.39 | 89.4 | 75.8 | 9.0 | 9.7 | 5.5 |
| 2 | | 145 | 4.9 | 1.041 | 2.8 | 0.113 | 80 | 19 | 6.38 | 86.5 | 66.0 | 10.4 | 12.3 | 11.3 |
| 3 | LR2 | 120 | 4.9 | 1.041 | 3.6 | 0.251 | 81 | 10 | 11.57 | 92.1 | 68.4 | 5.9 | 16.9 | 8.8 |
| 4 | | 145 | 4.9 | 1.041 | 2.6 | 0.326 | 81 | 6.5 | 5.92 | 85.6 | 63.9 | 10.8 | 12.9 | 12.4 |
| 5 | | 170 | 4.9 | 1.041 | 2.0 | 0.210 | 80 | 55 | 1.92 | 65.8 | 70.0 | 26.0 | 15.6 | 8.5 |
| 6 | LR3 | 145 | 4.9 | 1.174 | 3.8 | 0.337 | 80 | 6.0 | 7.15 | 87.7 | 62.4 | 8.7 | 15.5 | 13.4 |
| 7 | LR4 | 120 | | | | 0.244 | 89 | 15 | 3.14 | 75.86 | | | | |
| 8 | LR5 | 120 | 4 | | 2.7 | 0.114 | 80 | 15 | 7.57 | 88.3 | 74.3 | 9.8 | 8.6 | 7.4 |
| 9 | | 145 | 4 | | | 0.285 | 82 | 8 | 6.21 | 86.1 | 70.3 | 11.3 | 8.8 | 9.5 |
| 10 | LR6 | 120 | 4.9 | 1.083 | 3.0 | 0.224 | 81 | 14 | 4.82 | 82.8 | 59.2 | 12.3 | 16.7 | 11.8 |
| 11 | | 145 | 4.9 | 1.083 | 2.8 | 0.361 | 80 | 6.5 | 3.15 | 75.9 | 53.8 | 17.1 | 7.4 | 21.7 |

*The generally used solvent was 2-propylheptyl valerate. In Seq. No. 6 2-ethylhexyl acetate was used.

In the second group of test results shown in Table 12, the effect of alkyl substituents of different branching was investigated (Seq. Nos. 7-11). Compared to the n-butyl derivative, the secondary butyl derivative was found to be a much less selective catalyst for linear aldehyde production (Seq. No. 7). This is an apparent result of the steric inhibition of the desired tris-phosphine complex formation (see Example 56 for the nmr characteristics of the complex). It is also noted that the t-butyl diphenyl phosphine system showed no catalytic activity whatsoever under these condition. It is recalled that in that case no tris-phosphine was formed at all (see Example 57 for attempted complexing).

The last pair of ligands tested shows that minor structural differences can result in major differences in the selectivity of the catalyst system. The use of 3,3-dimethylbutyl diphenyl phosphine ligand, the carbon analog of SEP, resulted in the desired high n/i ratio of aldehydes (Seq. Nos. 8 and 9). This ligand does form tris-phosphine complex (see Example 59 for complex). In contrast, employing a neopentyl group having one less methylene group between the phosphorus and the sterically demanding t-butyl group led to much poorer catalyst formation (see Example 60).

Example 101

Hydroformylation with Chelating and Non-Chelating Alkylene Bis-(Diphenyl Phosphine) Rhodium Complex Catalysts In a series of experiments, the results of which are summarized in Table 13 alkylene bis(diphenyl phosphines) were tested as ligands for rhodium complex catalyzed hydroformylation under standard conditions.

The ligand to rhodium ratio was either 1.5 or about 70. Since these are bis-phosphine ligands, the above values correspond to a P/Rh ratio of 3 and 140, respectively.

The bis-phosphine ligands tested had an increasing number (n) of methylene, i.e., $CH_2$ groups, separating the two phosphorus atoms. This increase led to unexpected changes in catalysis.

In the case of the sterically crowded monomethylene (n=1) bis-phosphine, the catalyst system showed little activity and n/i selectivity at the L/Rh ratio of 1.5 and

TABLE 13

1-BUTENE HYDROFORMYLATION IN THE PRESENCE OF CHELATING AND NON-CHELATING ALKYLENE BIS-(DIPHENYL PHOSPHINE) RHODIUM COMPLEX CATALYSTS
Rh = 140 ppm; Catalyst Precusor: Dicarbonyl Acetyl Acetonato Rhodium, Total Pressure 350 psi (~26 Atm)

| Seq.* No. | $Ph_2P(CH_2)_nPPh_2$ Ligand n | Complex Exp. No. E- | Ratio L/Rh | Reaction Temp. °C | H2/CO Ratio Initial | H2/CO Ratio Feed | H2/CO Ratio Final | Rate Constant k, Min⁻¹ | Conversion, % | Reaction Time Min. | Aldehyde Product Linearity Ratio n/i | Aldehyde Product Linearity $\frac{100n}{n+i}$, % | Aldehydes n | Aldehydes i | Butane | 2-Butenes |
|---|---|---|---|---|---|---|---|---|---|---|---|---|---|---|---|---|
| 1 | 1 | 61 | 1.5 | 120 | 5 | 1.08 | 5.8 | 0.025 | 78 | 135 | 2.1 | 67.7 | 47.1 | 22.4 | 2.9 | 27.6 |
| 2 | 1 | | 71 | 120 | 4 | | | Nil | Nil | | | | | | | |
| 3 | 2 | 62 | 1.5 | 120 | 5 | 1.08 | 4.1 | 0.067 | 80 | 45 | 1.5 | 60.6 | 42.9 | 22.8 | 7.6 | 21.8 |
| 4 | 2 | | 69 | 145 | 4 | | | Nil | Nil | | | | | | | |
| 5 | 3 | 63 | 1.5 | 120 | 5 | 1.08 | 3.6 | 0.120 | 80 | 30 | 2.0 | 66.2 | 45.6 | 23.3 | 9.5 | 21.6 |
| 6 | 3 | | 73 | 120 | 5 | 1.08 | 5.9 | 0.030 | 80 | 65 | 1.3 | 56.5 | 52.1 | 40.2 | 4.5 | 3.2 |
| 7 | 4 | 64 | 69 | 145 | 4 | | | 0.190 | 81 | 11 | 3.3 | 76.5 | | | | |
| 8 | 6 | 66 | 1.5 | 120 | 5 | 1.08 | 3.5 | 0.139 | 81 | 15 | 4.1 | 80.4 | 63.3 | 15.5 | 9.7 | 11.5 |
| 9 | 6 | | 70 | 120 | 5 | 1.08 | 3.7 | 0.108 | 80 | 17 | 9.7 | 90.6 | 81.7 | 8.4 | 5.8 | 4.1 |
| 10 | 6 | | 70 | 145 | 4 | 1.17 | 3.3 | 0.332 | 81 | 6 | 8.0 | 88.9 | 64.4 | 8.1 | 13.9 | 13.6 |
| 11 | 6 | | 70 | 170 | 4 | 1.17 | 2.7 | 0.284 | 79 | 20 | 3.1 | 75.6 | 52.2 | 16.8 | 14.4 | 16.6 |
| 13 | 14 | 67 | 144 | 100 | 4 | | | 0.060 | 54 | | 3.8 | 79.2 | | | | |

*Experiments of Seq. No. 53-8 and 4 were carried out in 2-propylheptyl valerate, the rest in 2-ethylhexyl acetate.

no activity at L/Rh ratio of 71 (Seq. Nos. 1 and 2). The chelate forming dimethylene (n=2) bis-phosphine showed a similar behavior (Seq. Nos. 3 and 4).

The trimethylene (n=3) bis-phosphine ligand, which forms a different chelate (see Example 63), is more active that the previous ligands. It has significant activity when the L/Rh ratio is 1.5 (Seq. No. 5). However, as compared to the previous ligands, it has less activity and less selectivity when the L/Rh ratio is 73 (Seq. No. 6).

In contrast to the chelating bis-phosphines, the non-chelating polymethylene (n=4, 6, 14) bis-phosphines showed higher n/i product ratios at the higher L/Rh ratio (Seq. Nos. 7 to 13). The catalytic behavior of these bis-phosphine ligands, which form tris-phosphine complexes at high L/Rh ratios, is shown in detail in the case of the hexamethylene (n=6) compound. As can be seen at a 1.5 L/Rh ratio the hexamethylene bridged bis-phosphine ligand leads to an n/i aldehyde product ratio of 4.1. At a L/Rh ratio of 70, the n/i ratio is increased to 9.7 under otherwise identical conditions.

Example 102

Hydroformylation with Aryl, Amide and Amine Substituted Alkyl Diphenyl Rhodium Complex Catalysts In a series of standard 1-butene hydroformylation experiments, three substituted alkyl diphenyl phosphines representing aryl, amide and amine functionalities were studied as tris-phosphine rhodium complex forming ligands. The results are shown in Table 14. As shown therein, all three complexes were highly selective catalysts for linear aldehydes when stable. As the reaction temperature was increased beyond the stable range of the desired catalyst complexes, the selectivities, i.e. n/i aldehyde ratios, decreased.

As described, the tests show that the novel 2-phenylethyl-, 2-pyrrolidinonylethyl- and 2-diethylaminoethyl-diphenyl phosphine rhodium complexes previously described in Examples 68, 69 and 70 are selective catalysts in the hydroformylation of the present invention.

Example 103

Hydroformylation with Sulfone, Phosphine Oxide, Keto, Carboxylate, Hydroxy and Ether Substituted Alkyl Diphenyl Rhodium Complex Catalysts The series of standard butene-1 hydroformylation tests summarized in Table XVII, describe the catalytic behavior of further, variously substituted alkyl diphenyl phosphine rhodium complexes. As it was described in Examples 71 to 73 these complexes are all of the tris-phosphine type. The data of Table 15 show that they are all selective catalysts for forming highly linear aldehydes.

TABLE 14

BUTENE HYDROFORMYLATION IN THE PRESENCE OF ARYL, AMIDE AND AMINE SUBSTITUTED ALKYL DIPHENYL PHOSPHINE RHODIUM COMPLEX CATALYSTS

Catalyst: $L_3RH(CO)H$; L/Rh = 140 Rh = 110 ppm; Precursor: Dicarbonyl Acetylacetonato Rhodium;
Total Pressure 350 psi (~26 Atm); Solvent 2-Propylheptyl Valerate

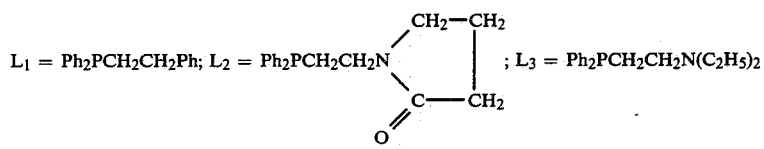

$L_1 = Ph_2PCH_2CH_2Ph$; $L_2 = Ph_2PCH_2CH_2N\langle$ (pyrrolidinone) ; $L_3 = Ph_2PCH_2CH_2N(C_2H_5)_2$

| Seq. No. | Ligand L | Example No. of Complex | Reaction Temp. °C. | H₂/CO Ratio Initial | H₂/CO Ratio Feed | H₂/CO Ratio Final | Rate Constant k,Min⁻¹ | Conversion, % | Reaction Time Min. | Ratio n/i | 100 n, n + i % | Selectivity to Various Compounds, % Aldehydes n | i | Butane | 2-Butenes |
|---|---|---|---|---|---|---|---|---|---|---|---|---|---|---|---|
| 1 | L₁ | 68 | 120 | 4.9 | 1.04 | 2.7 | 0.087 | 81 | 24 | 11.3 | 91.9 | 73.8 | 6.5 | 12.1 | 7.6 |
| 2 | | | 145 | 4.9 | 1.04 | 1.9 | 0.243 | 78 | 12 | 6.4 | 86.5 | 62.2 | 9.7 | 14.3 | 13.9 |
| 3 | | | 170 | 4.9 | 1.04 | 1.8 | 0.274 | 80 | 55 | 1.9 | 65.0 | 48.9 | 26.3 | 15.4 | 9.4 |
| 4 | L₂ | 69 | 100 | 4.9 | 1.04 | 10.2 | 0.011 | 80 | 205 | 12.9 | 92.8 | 81.1 | 6.3 | 6.4 | 6.2 |
| 5 | | | 110 | 4.9 | 1.04 | 4.2 | 0.045 | 81 | 41 | 12.6 | 92.6 | 77.0 | 6.1 | 9.5 | 7.4 |
| 6 | | | 120 | 4.9 | 1.04 | 3.7 | 0.094 | 81 | 21 | 12.5 | 92.5 | 74.6 | 6.0 | 11.0 | 8.4 |
| 7 | | | 130 | 4.0 | 1.04 | 3.1 | 0.109 | 80 | 19 | 10.4 | 91.2 | 70.1 | 6.8 | 12.4 | 10 |
| 8 | | | 140 | 4.9 | 1.04 | 3.0 | 0.125 | 80 | 20 | 7.6 | 88.4 | 65.3 | 8.6 | 13.6 | 12.5 |
| 9 | | | 145 | 4.9 | 1.04 | 2.5 | 0.185 | 80 | 18 | 6.2 | 86.1 | 63.0 | 10.1 | 12.8 | 14. |
| 10 | | | 155 | 4.9 | 1.04 | 2.4 | 0.201 | 80 | 40 | 3.5 | 77.8 | 58.2 | 16.6 | 13.2 | 12.0 |
| 11 | | | 170 | 4.9 | 1.04 | 2.0 | 0.156 | 77 | 75 | 2.0 | 66.7 | 49.1 | 24.5 | 16.4 | 6.2 |
| 12* | L₃ | 25 | 120 | 5.0 | 1.08 | 3.4 | 0.122 | 81 | 15 | 7.3 | 88.0 | 74.3 | 10.2 | 9.8 | 5.7 |

*Solvent 2-Ethylhexyl acetate

TABLE 15

1-BUTENE HYDROFORMYLATION IN THE PRESENCE OF SULFONE, PHOSPHINE OXIDE, KETO, ESTER, HYDROXY AND ETHER SUBSTITUTED ALKYL DIPHENYL PHOSPHINE CATALYSTS

Catalyst: $L_3Rh(CO)h$; L/Rh = 140; Rh = 110 ppm, Precursor: Dicarbonyl Acetylacetonato Rhodium;
Total Pressure 350 psi ($\sim$26 Atm)

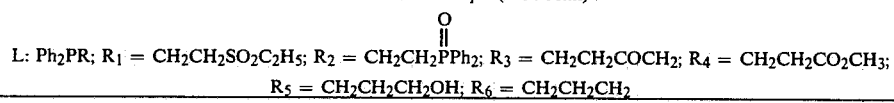

L: $Ph_2PR$; $R_1 = CH_2CH_2SO_2C_2H_5$; $R_2 = CH_2CH_2PPh_2$; $R_3 = CH_2CH_2COCH_2$; $R_4 = CH_2CH_2CO_2CH_3$;
$R_5 = CH_2CH_2CH_2OH$; $R_6 = CH_2CH_2CH_2$

| Seq.* No. | Ligand LR | Example No. of Complex | Reaction Temp. °C | H$_2$/CO Ratio Initial | Feed | Final | Rate Constant k, Min.$^{-1}$ | Conversion, % | Reaction Time Min. | Aldehyde Product Linearity Ratio n/i | 100n, n + i % | Selectivities to Various Compounds, % Aldehydes n | i | Butane | 2-Butenes |
|---|---|---|---|---|---|---|---|---|---|---|---|---|---|---|---|
| 1 | LR$_1$ | 71 | 100 | 5.0 | 1.08 | 4.6 | 0.016 | 80 | 115 | 12.5 | 92.6 | 85.2 | 6.8 | 2.5 | 5.5 |
| 2 | | | 120 | 5.0 | 1.08 | 4.2 | 0.048 | 80 | 37 | 14.6 | 93.6 | 80.6 | 5.5 | 6.0 | 7.8 |
| 3 | | | 145 | 5.0 | 1.27 | 6.9 | 0.160 | 77 | 10 | 11.8 | 92.2 | 77.0 | 6.5 | 6.2 | 10.2 |
| 4 | | | 170 | 5.0 | 1.27 | 3.0 | 0.119 | 80 | 50 | 2.4 | 70.1 | 47.0 | 20.0 | 18.2 | 14.8 |
| 5 | LR$_2$ | 72 | 145 | 4.0 | 1.04 | | 0.107 | 80 | 17 | 7.3 | 88.0 | — | — | — | — |
| 6 | LR$_3$ | 73 | 120 | 4.9 | 1.08 | 4.2 | 0.060 | 81 | 34 | 12.6 | 92.6 | 72.8 | 5.8 | 13.1 | 8.3 |
| 7 | | | 145 | 4.9 | 1.08 | 2.5 | 0.267 | 81 | 7.5 | 7.2 | 87.8 | 74.5 | 10.4 | 6.8 | 8.4 |
| 8 | | | 170 | 4.9 | 1.08 | 2.2 | 0.330 | 79 | 6.0 | 4.0 | 80.0 | 60.8 | 15.2 | 7.4 | 16.6 |
| 9 | LR$_4$ | 74 | 120 | 4.9 | 1.04 | 4.3 | 0.062 | 80 | 30 | 11.8 | 92.2 | 78.0 | 6.6 | 8.5 | 6.9 |
| 10 | | | 145 | 4.9 | 1.04 | 3.0 | 0.105 | 80 | 24 | 6.8 | 87.2 | 67.0 | 9.9 | 12.2 | 11.0 |
| 11 | LR$_5$ | 75 | 120 | 5.0 | 1.08 | 4.5 | 0.040 | 80 | 28 | 6.1 | 85.8 | 74.2 | 12.3 | 5.8 | 5.7 |
| 12 | (LR$_6$)$_2$O | 76 | 120 | 5.0 | 1.08 | 3.7 | 0.085 | 80 | 20 | 9.2 | 90.2 | 73.3 | 8.0 | 11.4 | 7.3 |

*Experiments of Seq. No. 1–4, 11 and 12 were carried out in 2-ethylhexyl acetate, the rest in 2-propylheptyl valerate.

With regard to the sulfone substituted ligand, 2-ethyl-sulfonylethyl diphenyl phosphine, it is noted that it gave a particularly selective catalyst complex. The activity of this complex rapidly increased in the 100° to 145° C. range. This behavior correlates with the formation of a highly stable complex having minimum ligand exchange at 35° (Example 71). The attractive catalytic properties of such a complex apparently depend on the specific manner of thermal activation plus stabilization in the present process.

Hydroformylation of Various Olefinic Compounds (Examples 104–106)

In the following, the hydroformylation of various olefinic compounds is described, mostly under standard conditions. As catalyst, tris-(trimethylsilylethyl diphenyl phosphine) rhodium carbonyl hydride was used throughout these experiments. At first, the hydroformylation of propylene will be described. Then a series of experiments on a variety of olefins including a non-hydrocarbon derivative will be discussed. Finally, it will be shown with isomeric pentenes, how the present process could be employed when starting with a mixture of olefins.

Example 104

Hydroformylation of Propylene

The complex of Example 48 was studied at the 458 ppm rhodium level, in the presence of a one hundred fold excess of trimethylsilylethyl diphenyl phosphine ligand, as a propylene hydroformylation catalyst. The reaction temperature was 100° C., the 1:4 CO/H$_2$ pressure was 400 psi. The general procedure previously employed for butene hydroformylation was used to carry out the reaction.

The reaction rate was found to be k=0.04 min$^{-1}$, expressed as the fraction reacted. In 60 minutes, 82% conversion was reached based on the CO/H$_2$ consumed. The ratio of n-butyraldehyde to methyl-propanal products was 5.0. The selectivity to these aldehydes was 87.5%. The selectivity to the by-product propane was only 2.5%.

Example 105

Hydroformylation of Miscellaneous Olefinic Compounds

In a series of experiments, the results of which are summarized in Table 16, a number of olefins were hydroformylated using the tris-SEP complex based catalyst system (Seq. Nos. 1–7).

Using a high L/Rh ratio, 1-pentene was selectively hydroformylated at 170° C. (Seq. No. 1). A lower L/Rh ratio was successfully used at 145° C. for the selective hydroformylation of 1-octene (Seq. No. 2).

A comparison of the n/i selectivities indicated that, in the absence of isomerization, 1-n-olefins of increasing carbon number react with increasing selectivity. Branching of terminal olefins further increased n/i selectivity. This is shown by the example of 3-methylbutene (Seq. No. 4). Internal olefins could also be hydroformylated as shown in the case of cis butene-2-hydroformylation (Seq. No. 5). It is important to note that isomerization to 1-butene also occurred as indicated by the formation of n-valeraldehyde.

A terminal olefin having a substituent on a vinylic carbon, such as 2-ethylhexene, showed an essentially specific terminal reaction to produce only the linear aldehyde derivative (Seq. No. 6).

TABLE 16
HYDROFORMYLATION OF VARIOUS OLEFINIC COMPOUNDS IN THE PRESENCE OF SEP - RHODIUM COMPLEX BASED CATALYST SYSTEMS

Catalyst: $L_3Rh(CO)H$; L = SEP = $Ph_2PCH_2CH_2Si(CH_3)_3$; Precursor: Dicarbonyl Acetylacetonato Rhodium;
Total Pressure 350 psi (26 Atm)
Solvent: 2-Ethylhexyl Acetate

| Seq. No. | Olefinic Reactant | Rh Conc., ppm | L/Rh | Reaction Temp. °C. | H$_2$/CO Ratio Initial | H$_2$/CO Ratio Feed | H$_2$/CO Ratio Final | Rate Constant k, min$^{-1}$ | Fraction of H$_2$/CO Reacted Conversion % | Reaction Time Min. | Aldehyde Product Linearity Ratio n/i | Aldehyde Product Linearity 100 n, % n + i | Selectivities to Various Compounds Aldehydes n | Selectivities to Various Compounds Aldehydes i | Bu- tane | 2-Bu- tenes |
|---|---|---|---|---|---|---|---|---|---|---|---|---|---|---|---|---|
| 1 | 1-Pentene | 105 | 510 | 170 | 5.0 | 117 | 3.0 | 0.193 | 80 | 12 | 7.5 | 88.2 | 53.3 | 7.1 | 19.3 | 20.2 |
| 2 | 1-Octene | 113 | 98 | 145 | 4.0 | 1.04 | | 0.257 | 80 | 8 | 6.8 | 87.2 | | | | |
| 3 | | | 141 | 165 | 4.0 | 1.04 | | 0.521 | 80 | 4 | 5.9 | 85.5 | | | | |
| 4 | 3-Methyl- butene | 110 | 140 | 145 | 5.0 | 1.27 | 6.6 | 0.274 | 81 | 10 | 23.9 | 96.0 | 70.8 | 3.0 | 25.2 | 0 |
| 5* | Cis-2- Butene | 447 | 256 | 170 | 5.0 | 1.27 | 3.6 | 0.018 | 80 | 150 | 1.0 | 49.5 | 38.7 | 41.4 | 6.1 | |
| 6 | 2-Ethyl- hexene | 553 | 28 | 120 | 1.08 | 1.08 | 1.45 | 0.007 | 40 | 135 | ∞ | 100 | 100 | Nil | Nil | Nil |
| 7** | Diallyl Ether | 112 | 140 | 120 | 5.0 | 1.08 | 31 | 0.434 | 80 | 5.5 | 3.6 | 78.3 | | | | |

*There was a 2.6% selectivity to amyl alcohols. Both mono and bis-hydroformylated products were formed.

Finally, an oxygenated diolefinic compound, diallyl ether, was also successfully hydroformylated without any apparent, major hydrogenation side reaction (Seq. No. 7). Both the mono- and bis- hydroformylated products could be selectively produced. At low conversions, the primary unsaturated aldehyde products predominated. At high conversions, a high yield of the dialdehyde products was obtained.

EXAMPLE 106
Hydroformylation of an Isomeric Mixture of Pentenes

The results of two exemplary hydroformylation experiments using a mixed pentenes feed are presented in Table 17 to show that all or certain components of olefin mixtures can be reacted.

In the experiments shown therein the tris-SEP rhodium complex was employed in the usual manner. However, no added solvent was employed.

The data show that the 1-n-olefin component (1-pentene) was the most reactive among the significant olefin components in both runs (Nos. 1 and 2). The minor branched olefin (3-methyl butene-1) was also highly reactive. High conversions of the internal olefin components (cis- and trans- pentene-2's) and the olefinically substituted terminal olefin (2-methylbutene) could also be realized under the more forcing conditions of run No. 2. It is noted that under the latter conditions some darkening of the reaction mixture occurred indicating some long term instability.

Example 107
Continuous Hydroformylation

The tris-(trimethylsilylethyl diphenyl phosphine) rhodium, carbonyl hydride catalyst system was extensively studied in a continuous hydroformylation unit.

TABLE 17
HYDROFORMYLATION OF MIXED PENTENES WITH TRIS-(TRIMETHYLSILYLETHYL DIPHENYL PHOSPHINE) RHODIUM COMPLEX CATALYST SYSTEM

Catalyst: $L^3Rh(CO)H$, L = SEP, L/Rh, 139; Precursor: Dicarbonyl Acetylacetonato Rhodium;
Olefin: 100 g Mixed Pentenes with Added Solvent

| Number | O: Feed | Reaction Conditions 1 | 2 |
|---|---|---|---|
| Temperature, °C. | | 120 | 120-145 |
| Time, Min. | | 300 | 360 |
| Olefin Conversion, % | | 30 | 55 |
| Rh Conc. ppm | | 109 | 293 |

| C$_5$ Hydrocarbons | Mole % | Mole % | Conv. % | Mole % | Conv. % |
|---|---|---|---|---|---|
| 3-Methylbutene | 0.31 | 0 | 100 | 0 | 100 |
| i-Pentane | 0.45 | 0.53 | — | 1.02 | — |
| l-Pentane | 8.04 | 0.89 | 89 | 0.71 | 91 |
| 2-Methylbutene | 24.61 | 19.13 | 22 | 7.14 | 71 |
| n-Pentene | 4.14 | 5.10 | — | 6.10 | — |
| t-2-Pentene | 28.97 | 19.95 | 31 | 5.63 | 81 |
| c-2-Pentene | 12.32 | 7.35 | 40 | 2.19 | 82 |
| 2-Methylbutene-2 | 21.04 | 22.22 | 0 | 22.46 | 0 |

| Aldehydes | None | Mole % | Mole % |
|---|---|---|---|
| 2-methylpentanal | — | 13.86 | 27.33 |
| 3-methylpentanal | — | 5.69 | 16.97 |
| 4-methylpentanal | — | — | — |
| n-hexanal | — | 5.27 | 10.46 |

The feed was butene-1 and the products were continuously removed together with the unreacted volatile components of the reaction mixture. The typical reaction temperature for the SEP based system was 120° C. Comparative runs were also carried out with a similar TPP based system at 100° C. Both systems could be successfully operated on the short run, although it appeared that the known degradation reactions and the stripping of the valeraldehyde trimer by-product at 100° C. could become a problem with TPP. The SEP system showed excellent long term stability and activity maintenance.

A representative 30 day continuous operation of the SEP catalyst system is illustrated in FIG. 12. With regard to the continuous operating conditions, it is noted that the total synthesis gas pressure was lower (125 psi, ~8.5 Atm) and the H$_2$/CO ratio higher (10/1) than in most of the batch studies. Also a higher concentration of rhodium (270 ppm) and a higher L/Rh ratio (210) were employed. Under these conditions a batch experiment produced results similar to those found in the continuous operation.

In the continuous hydroformylation the catalyst was generated from dicarbonyl acetylacetonato rhodium in situ. The precursor was a more active but much less selective hydroformylation catalyst than the desired final catalyst.

In a typical operation 1-butene was introduced into the reactor at a rate of 4.4 mole per hour. The rate of CO was typically 2 standard cubic feet per hour (SCFH). The hydrogen was introduced int he 15 to 25 SCFH range. By changing the hydrogen ratio the aldehyde production rate and other parameters could be appropriately and reversibly controlled.

During the reaction isomeric valeraldehyde trimers and some tetramers were formed. At an equilibrium concentration they were in the concentration range of from about 50 to 80% by wt.

After the reaction system came to equilibrium, the rate of hydrogen gel feed introduction was decreased from 19.2 to 17.6 SCFH (1 SCFH=28.3 dm³/hr) during the seventh day of the run. This resulted in an increased production rate. As expected, this process was fully reversible. Also, a decrease of the synthesis gas feed rate above the initial level, to 24.5 SCFH on the 15th day, resulted in the expected decreased production rate.

On the nineteenth day, the reaction temperature was raised to 125°. This resulted in an about 39% reaction rate increase as expected on the basis of an activation energy of 15.5 kcal. Subsequent changes of the space velocity of the synthesis gas feed at this higher temperature resulted in the expected reaction rate changes.

On the basis of the kinetic changes observed during the approximately 3 weeks of operation shown by the figure and on the basis of other continuous hydroformylations with the same catalyst system, a rate equation was developed. This rate equation did fit all the data. The rate constant remained unchanged after the startup equilibrium period for the 25 days shown. It is noted that the lack of change of the rate constant means that there is no loss of catalyst activity during this period. The only long term change in the catalyst system was some oxidation, probably by oxygen, of the phosphine ligand to the corresponding phosphine oxide. In the presence of excess phosphine, this oxidation had no adverse effect on the reaction rate. Combined gas chromatography and mass spectroscopy studies could not show any evidence of a ligand degradation similar to that reported to occur via o-phenylation in the TPP system.

Combined Hydroformylation-Aldolization

Examples (108–111)

Example 108

Combined Hydroformylation-Aldolization of 1-Butene at 120° C. in the Presence of tris-(Trimethylsilylethyl Diphenyl Phosphine) [SEP] Rhodium Carbonyl Hydride Complex

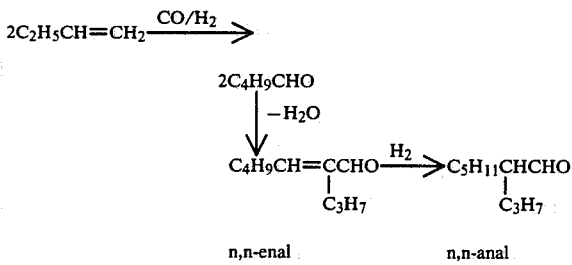

n,n-enal          n,n-anal

The combined hydroformylation, aldolization and hydrogenation of butene-1 was studied under typical conditions of the present hydroformylation process. The DTS rhodium complex was utilized as a typical substituted alkyl diaryl phosphine rhodium complex catalyst for hydroformylation and hydrogenation. Potassium hydroxide in methoxytriglycol was employed as an aldolization catalyst. The methoxytriglycol was also used as the solvent for the other components of the mixture. The catalyst system was employed at the 110 ppm rhodium concentration level. The ligand to rhodium ratio was 140. The 1-butene reactant was employed in a standard manner. The initial $H_2/CO$ mixture used to pressure the mixture to 350 psi (26 atm.) had a 5/1 mole ratio. The feed gas to maintain this pressure was a 1.5 to 1 mixture. The latter ratio was employed because it is theoretically needed to produce the n,n- and i/n-anals.

The reaction and product parameters of a group of experiments designed to observe the effect of varying concentrations of KOH are summarized in Table 18. The product parameters, i.e., selectivities to the various products were obtained by glc analyses. For the analyses of the $C_5$ and $C_{10}$ aldehydes, a special 2 m Carbowax column 10% CW on Chromosorb P diatomaceous earth was used. This was provided by Supelco, Inc., Supelco Park, PA. It provided good separation of the n,n-enal from the n,n-anal.

TABLE 18

COMBINED HYDROFORMYLATION-ALDOLIZATION OF 1-BUTENE AT 120° C. and 350 psi (2 atm.) in the Presence of SEP Rhodium Complex and Varying Amounts of KOH SEP = L = Ph₂CH₂CH₂Si(CH₃)₃; L/Rh = 140; Rh = 110

| Seq. No. | KOH % | H2/CO Ratio Initial | H2/CO Ratio Feed | H2/CO Ratio Final | Rate Constant k, min⁻¹ | Fraction of H2/CO Reacted Conversion % | Reaction Time Min. | Approx. Selectivities to Aldehydes Mole % C5's i | Approx. Selectivities to Aldehydes Mole % C5's n | n,n (i)- anal | n,n- enal | n/i Ratio | % n, 100 n / n+1 | Selectivity to n-Butane mole % |
|---|---|---|---|---|---|---|---|---|---|---|---|---|---|---|
| 1 | Nil | 5 | 1.08 | 2.7 | 0.056 | 80 | 50 | 9.2 | 90.8 | | | 9.9 | | 14.0 |
| 2 | Nil | 5 | 1.5 | 24.1 | 0.051 | 80 | 42 | 3.1 | 96.9 | | | 32.1 | 96.9 | 18.8 |
| 3 | Nil | 5 | 1.5 | 26.8 | 0.05 | 15 | 4 | 3.3 | 96.7 | | | 29.1 | 96.7 | |
| 2 | Nil | 5 | 1.50 | 21.3 | 0.042 | 15 | 6 | 6.7 | 93.3 | | | 13.8 | | |
| | | | | | | | 45 | 5.8 | 94.2 | | | 16.3 | | |
| | | | | | | | 60 | 5.5 | 94.5 | | | 17.2 | | |
| | | | | | | | 80 | 6.2 | 93.8 | | | 15.0 | 93.8 | 17.7 |
| 3 | 0.05 | 5 | 1.50 | 47 | 0.059 | 80 | 34 | 4.1 | 47.5 | 8.4 | 40.0 | 34.9 | 97.2 | 28.9 |
| 4 | 0.05 | 5 | 1.50 | 17.7 | 0.061 | 15 | 4 | 6.1 | 81.6 | 0.8 | 11.7 | 17.6 | 94.6 | |

TABLE 18-continued

COMBINED HYDROFORMYLATION-ALDOLIZATION OF 1-BUTENE AT 120° C. and 350 psi
(2 atm.) in the Presence of SEP Rhodium Complex and Varying Amounts of KOH SEP = L = $Ph_2CH_2CH_2Si(CH_3)_3$; L/Rh = 140; Rh = 110

| Seq. No. | KOH % | H2/CO Ratio | | | Rate Constant k, min$^{-1}$ | Fraction of H2/CO Reacted Conversion % | Reaction Time Min. | Approx. Selectivities to Aldehydes Mole % | | | | | n/i Ratio | % n, 100 n n + 1 | Selectivity to n-Butane mole % |
|---|---|---|---|---|---|---|---|---|---|---|---|---|---|---|---|
| | | Initial | Feed | Final | | | | C5's i | C5's n | n,n (i)- anal | n,n- enal | | | | |
| | | | | | | 30 | 18 | 5.5 | 76.8 | 1.0 | 16.7 | | 20.5 | 95.4 | |
| | | | | | | 45 | 11 | 5.4 | 72.9 | 1.5 | 20.2 | | 21.6 | 95.6 | |
| | | | | | | 60 | 16 | 5.2 | 67.3 | 2.7 | 24.7 | | 23.5 | 95.9 | |
| | | | | | | 80 | 30 | 5.9 | 51.5 | 7.8 | 34.8 | | 23.2 | 95.9 | 17.7 |
| 5 | 0.10 | 5 | 1.17 | 6.52 | 0.062 | 15 | 5 | 2.9 | 17.8 | 3.0 | 50.2 | | 42.9 | 94.3 | |
| | | | | | | 80 | 32 | 9.3 | 34.1 | 13.0 | 43.6 | | 15.8 | 77.1 | 15.0 |
| 6 | 0.10 | 5 | 1.50 | 5.0 | 0.048 | 80 | 42 | 3.4 | 27.1 | 18.3 | 51.2 | | 49.2 | 98.0 | 31.3 |
| 7 | 0.20 | 5 | 1.50 | 5.0 | 0.043 | 80 | 40 | 2.9 | 16.0 | 16.0 | 65.2 | | 60.5 | 98.4 | 28.8 |
| 8 | 0.20 | 5 | 1.50 | 13.6 | 0.049 | 15 | 3 | — | — | 10.8 | 89.2 | | — | | |
| | | | | | 0.028 | 30 | 5 | 3.7 | — | 11.5 | 84.9 | | 50.6 | 98.0 | |
| | | | | | | 45 | 12 | 3.0 | — | 12.0 | 85.0 | | 64.4 | 98.5 | |
| | | | | | | 60 | 16 | 3.3 | 7.5 | 13.6 | 75.8 | | 57.1 | 98.3 | |
| | | | | | | 80 | 32 | 3.6 | 17.7 | 18.6 | 60.1 | | 48.0 | 98.0 | |
| | | | | | | 92 | 62 | 4.9 | 14.1 | 34.5 | 46.5 | | 35.9 | 97.3 | 16.0 |

However, the separation of the n,n-enal from the i,n-enal was not good. The small quantities of the i,n-enal formed could not be determined. Therefore, the overall n,i-ratios in the reaction mixtures with KOH could not be exactly determined. The aldehyde selectivity to the main final $C_{10}$ aldehyde product, the n,n-enal, also includes minor quantities of the i,n-anal. However, this inclusion causes less than 10% change in the composition, since the minor i-$C_5$ aldehyde is crossaldolized at a very slow rate. The glc percentages are indicated on the basis of the peak intensities. No corrections were made for the possibly different glc response to $C_5$ and $C_{10}$ compounds.

In the first four experiments, the hydroformylation of butene was studied in methoxytriglycol but in the absence of KOH aldolization catalyst (Seq. Nos. 1 to 4) for comparison. All three experiments started with 5/1 $H_2CO$ gas. In the first experiment, the $H_2/CO$ ratio of the feed gas was close to one as usual. This experiment gave the usual high n/i ratio of $C_5$ aldehydes. This indicated that the solvent is an advantageous one, comparable to other polar oxygenated solvents (Seq. No. 1).

The rest of the experiments used the same initial $H_2/CO$ ratio of 5 but a different $H_2/CO$ feed, of 1.5. Also, the contents of the third and fourth reaction mixture were sampled for comparison with the experiments using added KOH. This and the other sampled runs provided less reliable absolute values than the uninterrupted experiments. However, sequences gave comparative relative numbers which showed the change of selectivity with increasing conversion.

The second experiment (Seq. No. 2) showed a much increased n/i ratio compared to the first. This was the consequence of the increasing $H_2/CO$ ratio, i.e., decreasing CO partial pressure during the reaction. Due to decreased availability of CO, this run also resulted in more hydrogenation of the 1-butene starting material and isomerized 2-butenes to n-butane.

The results of the first sampled experiment are somewhat similar. This experiment shows that as a consequence of increasing $H_2/CO$ ratio, the selectivity is much higher at 80% conversion. (Seq. No. 3).

The fourth experiment (Seq. No. 4) was sampled four times during the run. It showed that up to 60% conversion, the n/i ratio was moderately increasing as an apparent consequence of the increasing $H_2/CO$ ratio in the reaction mixture.

The second group of experiments (Seq. Nos. 5–10) was run using varying amounts of KOH, in the 0.05 to 0.2% range, under the same conditions. The data indicated that 0.2% KOH was sufficient for the rapid conversion of the primary n-$C_5$ aldehyde product (Seq. Nos. 7 and 8). The aldolization rate was much slower when 0.05% KOH was used (Seq. Nos. 5 and 6). The rate of the hydroformylation was estimated on the basis of the measured rate of synthesis gas consumption. Increasing $H_2/CO$ ratios generally resulted in increased n/i ratios and increased percentages of n-butane formation. Due to apparent CO starvation, the non-sampled mixtures gave rise to significantly higher $H_2/CO$ ratios than those frequently sampled during the run.

The hydrogenation of the unsaturated aldehyde to the saturated aldehyde was relatively low. At 45% synthesis gas conversion, the percentage n,n-anal formed was less than 10% of the n,n-enal present. At that conversion, the overall selectivity to the n,n-enal was in excess of 80%.

Example 109

Sequential Hydroformylation, Aldolization, Hydrogenation in Separate Steps

In a series of experiments, n-valeraldehyde was produced by the hydroformylation of 1-butane and separated from the i-isomer. A 20% methoxytriglycol solution of the n-valeraldehyde was then aldolized to provide the n,n-enal condensation product. It was observed that the aldolization was much slower in the absence of the hydroformylation catalyst system than in the presence of it in the previous example. After 30 minutes reaction time, only a 1.2% conversion was reached. After 14 hours, the aldehye conversion was 47.2%, i.e., the concentration of the n,n-enal in mole equivalents was 47.2%.

During the above experiment, and other experiments with KOH solutions in methoxytriglycol, yellow, then amber, then brown color formation was observed, indicating potential instability. The addition of 2% KOH to methoxytriglycol resulted in an amber color even at room temperature. Therefore, the amount of KOH in the hydroformylation experiments was minimized.

to the reaction mixture from the above aldolization experiment, the hydroformylation catalyst of the previous example was added. Then the mixture was pressured to 570 psi (~39 atm.) and heated as usual to 120° C. with a 20/1 mixture of H₂/CO. A high H₂/CO ratio was used increase the hydrogenation rate of the n,n-enal to the n,n-anal.

The hydrogenation of the n,n-enal to the n,n-anal was followed by glc. During the first 90 minutes, the percentage conversion increased as follows: 6 (5 min.); 13 (20 min.); 21 (40 min.); 28 (60 min.); and 39 (90 min.). Under these conditions, no further significant aldolization of the n-C₅ aldehyde occurred.

Example 110

Combined Hydroformylation-Aldolization of 1-Butene with Various Tris-(Alkyl Diphenyl Phosphine) Rhodium Carbonyl Hydride Complexes

The combined hydroformylation aldolization of 1-butene under the conditions of Example 108 was also studied witht he tris-(n-butyl diphenyl phosphine) and the tris-(n-hexyl diphenyl phosphone) complexes. The SEP complex was also used in this group of experiments under similar conditions but using a 1/1 rather than a 5/1 initial H₂/CO reactant ratio. The results are shown in Table 19.

Overall, the data of Table 19 show that different alkyl diphenyl phosphine complexes are similar catalysts for combined hydroformylation aldolization. The results also indicate that the provision of sufficient carbon monoxide for hydroformylation is a key factor in avoiding olefin hydrogenation.

The first two experiments (Seq. No.s 1 and 2) with the butyl diphenyl phosphine complex (A) show the effect of the KOH on the aldolization. The results are similar to those obtained in comparative experiments using the SEP complex in a previous example (See Table 19). The second pair of experiments (Seq. Nos. 3 and 4) shows the effect of starting witha synthesis gas having a low, i.e., 1.5, H₂CO ratio. Lower selectivities to the n-product are obtained but the reaction rates are increased and the by-product n-butane formation is drastically reduced. The two different catalyst ligands used in these experiments, i.e., n-hexyl diphenyl phosphine (B) and trimethylsilylethyl phosphine (C), led to similar results.

Example 111

Combined Hydrogenation-Aldolization of 1-Butene at 145° C. in the Presence of tris-SEP and tris-TPP Rhodium Carbonyl Hydride Complexes

The combined hydroformylation-aldolization of 1-butene was also studied under similar conditions at 145° C. At this temperature, the known tris-TPP complex is unstable under the reaction conditons. In contrast, the novel tris-SEP complex is stable. The experimental conditions and results are shown in Table 20.

As it is shown in this table, in the first pair of experiments (Seq. Nos. 1 and 2), both the triphenyl phosphine (TPP) complex and the trimethylsilylethyl diphenyl phosphine (SEP) complex were employed as hydroformylation catalysts in methoxytriglycol in the absence of KOH. A comparison of the results showed that the rate of the SEP complex catalyzed reaction was higher. Even more significantly, the selectivity of the SEP complex to produce aldehydes of high n/i ratios was much higher (Seq. No. 1). At 80% conversion, the SEP catalyzed reaction had a 7.6 n/i ratio. The comparable ratio for the TPP system was 3.1 (Seq. No. 2). Most revealingly, the TPP reaction gave an n/i ratio of 12.4 at 15% conversion. Apparently, during the further course of the experiment, the TPP catalyst system decomposed and led to species of much lower catalytic activity and selectivity.

In the second pair of experiments (Seq. Nos. 3 and 4), the same two catalyst systems were employed in the presence of KOH to effect hydroformylation and aldolization. KOH was found to be an effective aldolization catalyst. Both complexes were also effective in catalyzing the hydrogenation of the aldol condensation products. However, the difference between the activity and selectivity of the two catalysts remained. The SEP complex plus KOH system produced a 6.6 n/i ratio of aldehydes at 80% conversion (Seq. No. 3). The comparative n/i ratio for the TPP complex plus base was only 4.2 (Seq. No. 4).

TABLE 19

COMBINED HYDROFORMYLATION ALDOLIZATION OF 1-BUTENE AT 120° C. IN THE PRESENCE OF VARIOUS TRIS-(ALKYL DIPHENYL PHOSPHINE) RHODIUM CARBONYL HYDRIDE COMPLEXES
L = Ar₂PR; A: R = C₄H₉; B: R = C₆H₉; C: R = CH₂CH₂Si(CH₃)₃; L/Rh = 140; Rh = 110 ppm; Pressure = 350 psi (26 Atm)

| Seq. No. | Ligand Species | KOH % | H₂/CO Ratio Initial | H₂/CO Ratio Feed | H₂/CO Ratio Final | Rate Constant k, min⁻¹ | Conversion % | Reaction Time Min. | C5's i- | C5's n | C10's n,n(i) anal | C10's n,n-enal | n/i Ratio | % n $\frac{100\,n}{n+1}$ | Selectivity to n-Butane mole % |
|---|---|---|---|---|---|---|---|---|---|---|---|---|---|---|---|
| 1 | A | Nil | 5 | 1.5 | 20.1 | 0.058 | 15 | 4 | 4.9 | 95.1 | | | 19.6 | 95.1 | |
| | | | | | | | 80 | 34 | 4.4 | 95.6 | | | 21.9 | 95.6 | 13.0 |
| 2 | A | 0.1 | 5 | 1.5 | 21.0 | 0.043 | 15 | 5 | 10.7 | 16.8 | 7.3 | 65.2 | 15.1 | 93.8 | |
| | | | | | | | 80 | 42 | 6.7 | 24.5 | 21.9 | 46.9 | 24.1 | 96.0 | 13.7 |
| 3 | B | 0.1 | 1.5 | 1.5 | 11.6 | 0.151 | 15 | 2 | 18.5 | 75.2 | | 7.3 | 4.8 | 82.8 | |
| | | | | | | | 80 | 12 | 14.1 | 63.1 | 6.7 | 16.0 | 7.7 | 88.5 | 1.9 |
| 4 | C | 0.1 | 1.5 | 1.5 | 6.8 | 0.088 | 15 | 3 | 18.0 | 75.7 | | 6.3 | 4.9 | 83.1 | |
| | | | | | | | 80 | 20 | 16.0 | 73.6 | 0.9 | 9.5 | 5.9 | 88.5 | |
| | | | | | | | 109 | 120 | 19.0 | 12.8 | 34.4 | 33.8 | 7.5 | 88.2 | 2.1 |

TABLE 20

COMBINED HYDROFORMYLATION ALDOLIZATION OF 1-BUTENE AT 145° C. AND 350 psi (~26 atm.) IN THE PRESENCE OF TRIS-SEP AND TRIS-TPP RHODIUM CARBONYL HYDRIDE COMPLEXES
SEP = $Ph_2PCH_2CH_2CH_2Si(CH_3)_3$; TPP = $Ph_3P$; L/Rh = 140; Rh = 110 ppm

| Seq. No. | Ligand Species | KOH % | $H_2/CO$ Ratio Initial | $H_2/CO$ Ratio Feed | $H_2/CO$ Ratio Final | Fraction $H_2/CO$ Reacted Rate Contant k, min$^{-1}$ | Conversion % | Reaction Time Min. | C5's i- | C5's n | C10's n,n(i) anal | C10's n,n-enal | n/i Ratio | % n $\frac{100\,n}{n+1}$ | Selectivity to n-Butane mole % |
|---|---|---|---|---|---|---|---|---|---|---|---|---|---|---|---|
| 1 | SEP | Nil | 5 | 1.17 | 2.7 | 0.174 | 79 | 18 | 11.6 | 88.4 | | | 7.6 | 88.6 | 12.0 |
| 2 | TPP | Nil | 5 | 1.5 | 14.7 | 0.138 | 15 | 1 | 7.5 | 92.5 | | | 12.4 | 92.5 | |
|   |     |     |   |     |      |       | 80 | 90 | 24.6 | 75.4 | | | 3.1 | 75.4 | 15.4 |
| 3 | SEP | 0.2 | 5 | 1.5 | 4.6 | 0.07 | 80 | 42 | 15.2 | 21.1 | 44.4 | 19.4 | 6.7 | 87.0 | 19.4 |
| 4 | TPP | 0.1 | 5 | 1.5 | 6.4 | 0.121 | 15 | 1.5 | 8.6 | 38.4 | 3.0 | 50.0 | 16.8 | 94.4 | |
|   |     |     |   |     |      |       | 80 | 80 | 29.7 | 12.0 | 48.5 | 9.8 | 4.2 | 80.6 | 13.2 |

The above quantitative observations on the relative stability of the SEP and TPP based systems could be qualitatively predicted when observing the respective reaction mixtures after the reactions. The SEP systems without and with base were yellow and amber, respectively. The TPP systems with and without base became black.

INDUSTRIAL APPLICABILITY

The catalysts and processes of the invention are useful in producing aldehydes from olefins.

What is claimed is:

1. A nitrogen heterocycle substituted alkyl diaryl phosphine rhodium carbonyl hydride complex catalyst of the formula

wherein
Ar is an aryl group containing from 6 to 10 carbon atoms;
Q is a divalent organic radical selected from an alkylene radical and an alkylene radical the carbon chain of which is interrupted at least one ether oxygen or phenylene group wherein said alkylene radical contains from 1 to 30 carbon atoms;
R represents a divalent organic radical selected from the group consisting of

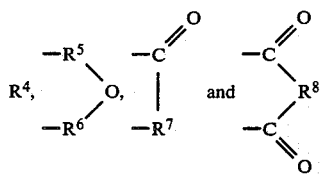

which together with the nitrogen atom forms a heterocyclic nitrogen-containing ring wherein $R^4$, $R^5$, $R^6$, $R^7$ and $R^8$ are hydrocarbyl radicals such that said heterocyclic ring contains from 5 to 6 atoms; and g is 2 or 3.

2. A catalyst complex of claim 1 wherein Ar is phenyl and Q is $(CH_2)_2$ or $(CH_2)_3$.

3. A catalyst complex according to claim 1 of the formula

wherein Ph is phenyl and m is 1 to 30.

4. A catalyst complex of the formula

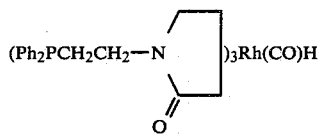

wherein Ph is phenyl.

5. A catalyst complex of the formula

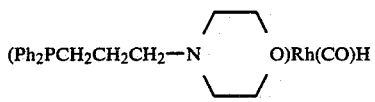

wherein Ph is phenyl.

6. A heterocycle-substituted alkyl diaryl phosphine rhodium carbonyl hydride complex catalyst of the formula

wherein
Ar is an aryl group containing from 6 to 10 carbon atoms;
Q is a divalent organic radical selected from an alkylene radical the carbon chain of which is interrupted with at least one ether oxygen or phenylene group, wherein said alkylene radical contains from 1 to 30 carbon atoms; and
E is a member selected from —N< and R is an organic radical which when bonded to —E⌒R forms a heterocyclic radical said heterocyclic radical being selected from the group consisting of

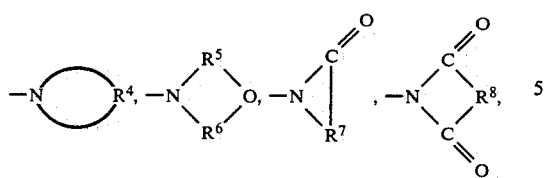

pyrryl, and furyl and wherein $R^4$, $R^5$, $R^6$, $R^7$ and $R^8$ are hydrocarbyl radicals such that said heterocyclic ring contains 5 to 6 atoms.

7. The complex catalyst of claim 6 wherein Ar is phenyl and Q is $(CH_2)_2$ or $(CH_2)_3$.

8. A heterocycle-substituted alkyl diaryl phosphine rhodium carbonyl hydride complex catalyst of the formula

wherein
Ar is an aryl group containing from 6 to 10 carbon atoms;
Q is a divalent organic radical selected from an alkylene radical the carbon chain of which is interrupted with at least one ether oxygen or phenylene group, wherein said alkylene radical contains from 1 to 30 carbon atoms; and
Y is a heterocyclic aryl group selected from the group consisting of pyrryl and furyl.

9. Tris(pyridylethyl diphenyl phosphine) rhodium carbonyl hydride.

10. Tris(furylethyl diphenyl phosphine) rhodium carbonyl hydride.

11. Tris(carbazylethyl diphenyl phosphine) rhodium carbonyl hydride.

* * * * *